US010660697B2

(12) United States Patent
Xiao et al.

(10) Patent No.: US 10,660,697 B2
(45) Date of Patent: *May 26, 2020

(54) HOLLOW BODY CAVITY ABLATION APPARATUS

(71) Applicant: CARDEA MEDSYSTEMS (TIANJIN) CO., LTD., Nankai District (CN)

(72) Inventors: Jia Hua Xiao, Santa Rosa, CA (US); Roger A. Stern, Cupertino, CA (US); Jerome Jackson, Los Altos, CA (US); Grant Michael Glaze, Sunnyvale, CA (US)

(73) Assignee: CARDEA MEDSYSTEMS (TIANJIN) CO., LTD., Nankai District, Tianjin (CN)

( * ) Notice: Subject to any disclaimer, the term of this patent is extended or adjusted under 35 U.S.C. 154(b) by 398 days.

This patent is subject to a terminal disclaimer.

(21) Appl. No.: 14/791,353

(22) Filed: Jul. 3, 2015

(65) Prior Publication Data

US 2015/0305805 A1 Oct. 29, 2015

Related U.S. Application Data

(63) Continuation-in-part of application No. 12/927,311, filed on Nov. 10, 2010, now Pat. No. 9,173,702, and
(Continued)

(51) Int. Cl.
*A61B 18/14* (2006.01)
*A61B 18/12* (2006.01)
*A61B 18/00* (2006.01)

(52) U.S. Cl.
CPC ...... *A61B 18/1482* (2013.01); *A61B 18/1206* (2013.01); *A61B 18/1485* (2013.01);
(Continued)

(58) Field of Classification Search
CPC ... A61B 18/14; A61B 18/148; A61B 18/1482; A61B 18/1485; A61B 2018/00214;
(Continued)

(56) References Cited

U.S. PATENT DOCUMENTS 3,924,628 A 12/1975 Droegemueller et al.
4,016,867 A 4/1977 King et al.
(Continued)

FOREIGN PATENT DOCUMENTS

CN 1290148 A 4/2001
CN 1308510 A 8/2001
(Continued)

OTHER PUBLICATIONS

Novasure: Instructions for Use and Controller Operator's Manual, 716011 Revision B; Cytyc Surgical Products, Year: 2004.
(Continued)

*Primary Examiner* — Jaymi E Della
(74) *Attorney, Agent, or Firm* — David Lewis; Jennifer A. Haynes; Bowen Liu

(57) ABSTRACT

An ablation apparatus places electrodes at the perimeter of a cavity. In an embodiment, the alternating electric field is used to expose the cavity to enough energy to ablate the cavity. In an embodiment, two modes are used to expose different regions of the cavity to different amounts of power so that the thermal effect is more uniform. In an embodiment, the electrodes have a relatively large surface area so as to avoid charring the cavity, but are shaped so as to fit within a body orifice.

28 Claims, 31 Drawing Sheets
(7 of 31 Drawing Sheet(s) Filed in Color)

Related U.S. Application Data a continuation-in-part of application No. 14/736,212, filed on Jun. 10, 2015, which is a continuation of application No. 12/927,311, filed on Nov. 10, 2010, now Pat. No. 9,173,702.

(60) Provisional application No. 61/259,973, filed on Nov. 10, 2009.

(52) U.S. Cl.
CPC . *A61B 18/1492* (2013.01); *A61B 2018/00011* (2013.01); *A61B 2018/0016* (2013.01); *A61B 2018/00083* (2013.01); *A61B 2018/00214* (2013.01); *A61B 2018/00482* (2013.01); *A61B 2018/00559* (2013.01); *A61B 2018/00577* (2013.01); *A61B 2018/00684* (2013.01); *A61B 2018/00916* (2013.01); *A61B 2018/00946* (2013.01); *A61B 2018/1407* (2013.01); *A61B 2018/1437* (2013.01); *A61B 2018/1465* (2013.01); *A61B 2018/1467* (2013.01); *A61B 2018/1475* (2013.01); *A61B 2218/007* (2013.01)

(58) Field of Classification Search
CPC ........... A61B 2018/00267; A61B 2018/00559; A61B 2018/00654; A61B 2018/1405; A61B 2018/1407; A61B 2018/144; A61B 2018/1465; A61B 18/1206; A61B 2018/1206; A61B 2018/00011; A61B 2218/007; A61B 2018/00684; A61B 2018/1437; A61B 2018/00482; A61B 2018/126; A61B 2018/124; A61B 2018/1246; A61B 2018/1475; A61B 2018/1492; A61B 2018/00494; A61B 2018/00488
See application file for complete search history.

(56) References Cited

U.S. PATENT DOCUMENTS

| | | |
|---|---|---|
| 4,121,572 A | 10/1978 | Krzeminski |
| 4,204,548 A | 5/1980 | Kurz |
| 4,685,474 A | 8/1987 | Kurz et al. |
| 4,764,845 A | 8/1988 | Artus |
| 4,873,986 A | 10/1989 | Wallace |
| 4,932,421 A | 6/1990 | Kaali et al. |
| 4,949,718 A | 8/1990 | Neuwirth et al. |
| 5,242,390 A | 9/1993 | Goldrath |
| 5,275,595 A | 1/1994 | Dobak, III |
| 5,277,201 A | 1/1994 | Stern |
| 5,313,943 A | 5/1994 | Houser et al. |
| 5,437,629 A | 8/1995 | Goldrath |
| 5,449,380 A | 9/1995 | Chin |
| 5,500,012 A | 3/1996 | Brucker et al. |
| 5,520,682 A | 5/1996 | Baust et al. |
| 5,540,658 A | 7/1996 | Evans et al. |
| 5,542,928 A | 8/1996 | Evans et al. |
| 5,558,672 A | 9/1996 | Edwards et al. |
| 5,575,788 A | 11/1996 | Baker et al. |
| 5,613,950 A | 3/1997 | Yoon |
| 5,647,868 A | 7/1997 | Chinn |
| 5,693,078 A | 12/1997 | Desai et al. |
| 5,702,438 A | 12/1997 | Avitall |
| 5,769,880 A | 6/1998 | Truckai et al. |
| 5,776,129 A | 7/1998 | Mersch |
| 5,782,899 A | 7/1998 | Imran |
| 5,800,493 A | 9/1998 | Stevens et al. |
| 5,848,969 A | 12/1998 | Panescu et al. |
| 5,868,735 A | 2/1999 | Lafontaine |
| 5,868,740 A | 2/1999 | LeVeen et al. |
| 5,891,134 A | 4/1999 | Goble et al. |
| 5,916,213 A | 6/1999 | Haissaguerre et al. |
| 5,954,714 A | 9/1999 | Saadat et al. |
| 6,009,877 A | 1/2000 | Edwards |
| 6,033,397 A | 3/2000 | Laufer et al. |
| 6,033,398 A | 3/2000 | Farley et al. |
| 6,068,629 A | 5/2000 | Haissaguerre et al. |
| 6,139,538 A | 10/2000 | Houghton et al. |
| 6,142,994 A * | 11/2000 | Swanson ............ A61B 18/1482 606/41 |
| 6,161,047 A | 12/2000 | King et al. |
| 6,197,022 B1 | 3/2001 | Baker |
| 6,270,495 B1 | 8/2001 | Palermo |
| 6,306,129 B1 | 10/2001 | Little et al. |
| 6,425,895 B1 | 7/2002 | Swanson et al. |
| 6,475,212 B2 | 11/2002 | Dobak, III et al. |
| 6,514,252 B2 | 2/2003 | Nezhat et al. |
| 6,547,784 B1 | 4/2003 | Thompson et al. |
| 6,620,161 B2 | 9/2003 | Schulze et al. |
| 6,813,520 B2 | 11/2004 | Sampson et al. |
| 6,929,642 B2 * | 8/2005 | Xiao .................. A61B 18/1485 128/898 |
| 6,960,203 B2 | 11/2005 | Xiao et al. |
| 7,074,217 B2 | 7/2006 | Strul et al. |
| 7,101,367 B2 | 9/2006 | Xiao et al. |
| 7,115,124 B1 | 10/2006 | Xiao |
| 7,481,808 B2 | 1/2009 | Koyfman et al. |
| 9,173,702 B2 | 11/2015 | Stern et al. |
| 2002/0022870 A1 | 2/2002 | Truckai et al. |
| 2002/0111615 A1 | 8/2002 | Cosman et al. |
| 2002/0120261 A1 | 8/2002 | Morris et al. |
| 2002/0151889 A1 | 10/2002 | Swanson et al. |
| 2003/0199817 A1 | 10/2003 | Thompson et al. |
| 2003/0212389 A1 | 11/2003 | Durgin et al. |
| 2004/0002698 A1 | 1/2004 | Hua Xiao et al. |
| 2004/0002702 A1 | 1/2004 | Xiao et al. |
| 2004/0002703 A1 | 1/2004 | Xiao et al. |
| 2004/0054366 A1 | 3/2004 | Davison et al. |
| 2005/0033285 A1 | 2/2005 | Swanson et al. |
| 2005/0267468 A1 * | 12/2005 | Truckai ............... A61B 18/1485 606/41 |
| 2006/0089636 A1 | 4/2006 | Christopherson et al. |
| 2007/0083193 A1 * | 4/2007 | Werneth ............... A61B 5/0422 606/41 |
| 2007/0083195 A1 | 4/2007 | Werneth et al. |
| 2007/0173806 A1 * | 7/2007 | Orszulak ................ A61B 18/12 606/34 |
| 2007/0270796 A2 * | 11/2007 | Girard ..................... A61B 18/14 606/45 |
| 2009/0054773 A1 | 2/2009 | Shizuka |
| 2009/0062787 A1 | 3/2009 | Schaer et al. |
| 2009/0062795 A1 | 3/2009 | Vakharia et al. |
| 2011/0112524 A1 | 5/2011 | Stern et al. |
| 2015/0272670 A1 | 10/2015 | Xiao et al. |

FOREIGN PATENT DOCUMENTS

| | | |
|---|---|---|
| CN | 100396251 C | 6/2008 |
| CN | 102256560 A | 11/2011 |
| CN | 102596082 B | 2/2015 |
| EP | 2498708 B1 | 1/2019 |
| WO | WO/1995/10326 A1 | 4/1995 |
| WO | WO/2011/059487 A2 | 5/2011 |

OTHER PUBLICATIONS

Picture of Novasure Unit, Unit with Disposable, and Novasure Disposable (from prior to Aug. 10, 2010).

Title: "Treatment of Menorrhagia by Radio Frequency Heating"; Prior, M. V., et al., vol. 7, No. 2, International Journal of Hyperthermia, Taylor & Francis Ltd.; Year: 1991, pp. 213-220.

Title: "Cryocoagulation of the Endometrium at the Uterine Cornua"; Droegemueller, William, et al., vol. 131, No. 1, American Journal of Obstetrics and Gynecology; The C. V. Mosby Co.; Year: May 1, 1978, pp. 1-9.

(56) References Cited

OTHER PUBLICATIONS

Title: "A Computer-Controlled, Continuously Circulating, Hot Irrigating System for Endometrial Ablation"; Baggish, Michael, et al., vol. 173, No. 6, American Journal of Obstetrics and Gynecology; The C. V. Mosby Co.; Year: Dec. 1995, pp. 1842-1848.

Title: "Preliminary Clinical Experience With a Thermal Balloon Endometrial Ablation Method to Treat Menorrhagia"; Singer, Albert, et al., vol. 83, No. 5, Part 1, The American College of Obstetricians and Gynecologists; Year: May 1994, pp. 732-734.

\* cited by examiner

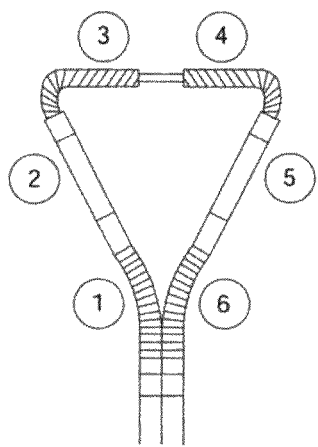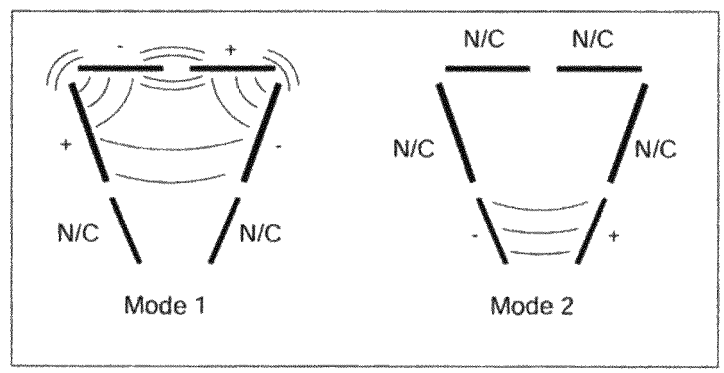
FIG. 1D

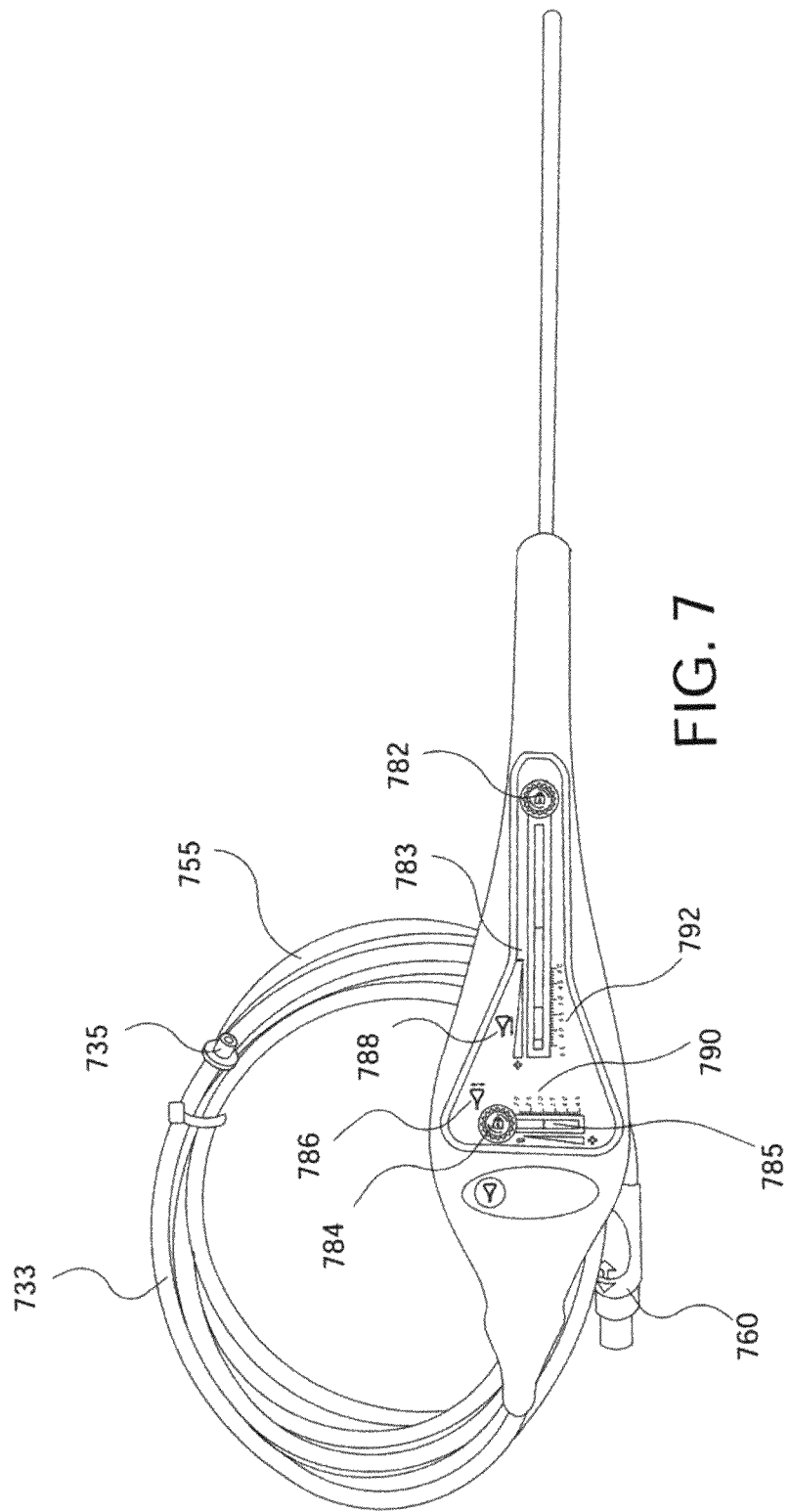

Cardea Aspiration Bottle

Table 2A FIG. 16

| Treatment # | Dimensions | | Phase | | | | Depth (mm) | | |
|---|---|---|---|---|---|---|---|---|---|
| | | | Mode 1 | | Mode 2 | | | | |
| | Width (cm) | Length (cm) | Power (W) | Time (s) | Power (W) | Time (s) | D1 - Proximal | D2 - Half D1/D3 | D3 - Center |
| 1 | 3.25 | 5.25 | 75 | 90 | 35 | 30 | 5 | 7 | 6 |
| 2 | 3.25 | 5.25 | 75 | 90 | 35 | 30 | 5 | 8 | 7 |
| 3 | 3.25 | 5.25 | 75 | 90 | 35 | 30 | 6 | 6 | 7 |
| 4 | 3.25 | 5.25 | 75 | 90 | 35 | 30 | 5 | 6 | 5 |
| 5 | 3.25 | 4 | 70 | 90 | 20 | 30 | 5 | 7 | 6 |
| 6 | 3.25 | 4 | 70 | 90 | 20 | 30 | 5 | 7 | 6 |
| 7 | 3.25 | 4 | 70 | 90 | 20 | 30 | 5 | 8 | 7 |
| 8 | 3.25 | 4 | 70 | 90 | 20 | 30 | 5 | 7 | 6 |
| 2 | 4.5 | 6.5 | 100 | 120 | 50 | 30 | 5 | 7 | 6 |
| 3 | 4.5 | 6.5 | 100 | 120 | 50 | 30 | 5 | 6 | 6 |
| 4 | 4.5 | 6.5 | 100 | 120 | 50 | 30 | 5 | 8 | 7 |
| 5 | 4.5 | 6.5 | 100 | 120 | 50 | 30 | 5 | 8 | 7 |
| 6 | 4.5 | 6.5 | 100 | 120 | 50 | 30 | 5 | 7 | 7 |
| 7 | 4.5 | 6.5 | 100 | 120 | 60 | 30 | 5 | 8 | 10 |
| 8 | 3.25 | 6.5 | 85 | 90 | 50 | 30 | 5 | 8 | 7 |
| 9 | 3.25 | 6.5 | 85 | 90 | 50 | 30 | 5 | 7 | 7 |
| 10 | 3.25 | 6.5 | 85 | 90 | 50 | 30 | 5 | 8 | 7 |
| 12 | 3.25 | 6.5 | 85 | 90 | 50 | 30 | 5 | 6 | 6 |
| 13 | 3.25 | 6.5 | 85 | 90 | 70 | 30 | 5 | 5 | 7 |
| 14 | 2 | 6.5 | 80 | 60 | 55 | 30 | 5 | 5 | 7 |
| 15 | 2 | 6.5 | 80 | 60 | 55 | 30 | 5 | 6 | 7 |
| 16 | 2 | 6.5 | 80 | 60 | 55 | 30 | 5 | 5 | 6 |
| 17 | 2 | 6.5 | 80 | 60 | 75 | 30 | 5 | 6 | 5 |
| 18 | 2 | 6.5 | 80 | 60 | 75 | 30 | 5 | 6 | 7 |
| 19 | 2 | 6.5 | 80 | 90 | 55 | 30 | 5 | 5 | 8 |
| 20 | 2 | 6.5 | 80 | 90 | 55 | 30 | 5 | 6 | 8 |

Table 2B FIG. 17

| Treatment # | Dimensions | | Phase | | | | Half D3/D5 - Distal | | Result |
|---|---|---|---|---|---|---|---|---|---|
| | Width (cm) | Length (cm) | Mode 1 | | Mode 2 | | | | |
| | | | Power (W) | Time (s) | Power (W) | Time (s) | | | |
| 1 | 3.25 | 5.25 | 75 | 90 | 35 | 30 | 6 | 5 | Good |
| 2 | 3.25 | 5.25 | 75 | 90 | 35 | 30 | 6 | 5 | Good |
| 3 | 3.25 | 5.25 | 75 | 90 | 35 | 30 | 7 | 5 | Good |
| 4 | 3.25 | 5.25 | 75 | 90 | 35 | 30 | 6 | 5 | Good |
| 5 | 3.25 | 4 | 70 | 90 | 20 | 30 | 6 | 5 | Good |
| 6 | 3.25 | 4 | 70 | 90 | 20 | 30 | 5 | 6 | Good |
| 7 | 3.25 | 4 | 70 | 90 | 20 | 30 | 6 | 5 | Good |
| 8 | 3.25 | 4 | 70 | 90 | 20 | 30 | 6 | 5 | Good |
| 2 | 4.5 | 6.5 | 100 | 120 | 50 | 30 | 7 | 5 | Good |
| 3 | 4.5 | 6.5 | 100 | 120 | 50 | 30 | 7 | 5 | Good |
| 4 | 4.5 | 6.5 | 100 | 120 | 50 | 30 | 8 | 7 | Good |
| 5 | 4.5 | 6.5 | 100 | 120 | 50 | 30 | 8 | 6 | Good |
| 6 | 4.5 | 6.5 | 100 | 120 | 50 | 30 | 7 | 6 | Good |
| 7 | 4.5 | 6.5 | 100 | 120 | 60 | 30 | 10 | 8 | Good |
| 8 | 3.25 | 6.5 | 85 | 90 | 50 | 30 | 7 | 5 | Good |
| 9 | 3.25 | 6.5 | 85 | 90 | 50 | 30 | 8 | 5 | Good |
| 10 | 3.25 | 6.5 | 85 | 90 | 50 | 30 | 7 | 5 | Good |
| 12 | 3.25 | 6.5 | 85 | 90 | 50 | 30 | 6 | 6 | Good |
| 13 | 3.25 | 6.5 | 85 | 90 | 70 | 30 | 7 | 6 | Good |
| 14 | 2 | 6.5 | 80 | 60 | 55 | 30 | 6 | 5 | Good |
| 15 | 2 | 6.5 | 80 | 60 | 55 | 30 | 6 | 5 | Good |
| 16 | 2 | 6.5 | 80 | 60 | 55 | 30 | 6 | 6 | Good |
| 17 | 2 | 6.5 | 80 | 60 | 75 | 30 | 5 | 5 | Good |
| 18 | 2 | 6.5 | 80 | 90 | 75 | 30 | 7 | 5 | Good |
| 19 | 2 | 6.5 | 80 | 90 | 55 | 30 | 7 | 6 | Good |
| 20 | 2 | 6.5 | 80 | 90 | 55 | 30 | 7 | 5 | Good |

Depth of Necrosis in Different Segments [mm] H&E / NBT

2100c

| Case # | Proximal segment | Upper segment | Middle point | Middle to cornea segment | Segments near cornea | Fundus |
|---|---|---|---|---|---|---|
| 1 | 5 / 7 | 6 / 8 | 9 / 9 | 8.5 / 6 | 6 / 5 | 9 / 6 |
| 2 | 6 / 6 | 4 / 7 | 5 / 5 | - / 5 | 8 / 7 | 5 / 6 |
| 3 | 6 / 7 | 10 / 9 | 6 / 9 | 6 / 7 | - / 5 | 7 / 7 |
| 4 | - / 5 | 6 / 7 | 7 / 7 | - / 6 | 5 / 5 | 4 / 4 |
| 5 | 7 / 7 | 7 / 8 | 6 / 10 | 5 / 9 | 7 / 8 | 7 / 6 |

FIG. 21C

HOLLOW BODY CAVITY ABLATION APPARATUS

CROSS-REFERENCE TO RELATED APPLICATIONS

This application is a continuation-in-part of U.S. patent application Ser. No. 14/736,212, entitled "Hollow Body Cavity Ablation Apparatus," filed Jun. 10, 2015, by Jia Hoa Xiao, et al., which is a continuation of U.S. patent application Ser. No. 12/927,311, now U.S. Pat. No. 9,173,702, entitled "Hollow Body Cavity Ablation Appratus," filed Nov. 10, 2010, by Jia Hua Xiao, et al., which in turn claims priority benefit of U.S. Provisional Patent Application No. 61/259,973, entitled "Hollow Body Cavity Ablation Apparatus," filed Nov. 10, 2009, by Roger Alan Stern, et al.; and this application is a continuation-in-part of U.S. patent application Ser. No. 12/927,311, now U.S. Pat. No 9,173,702, entitled "Hollow Body Cavity Ablation Apparatus," filed Nov. 10, 2010, by Jia Hua Xiao, et al.; which in turn claims priority to U.S. Provisional Patent Application No. 61/259,973 , entitled "Hollow Body Cavity Ablation Apparatus," filed Nov. 10, 2009, by Roger Alan Stern, et al. All of the above applications are incorporated herein by reference.

FIELD

This specification generally relates to embodiments of hollow body ablation devices and uses thereof.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Ablation of the interior lining of a body organ is a procedure that involves heating the organ lining to temperatures that destroys the cells of the lining and coagulates blood flow for hemostasis. Such a procedure may be performed as a treatment to one of many conditions, such as chronic bleeding of the endometrial layer of the uterus or abnormalities of the mucosal layer of the gallbladder. Existing methods for effecting ablation include circulation of a heated fluid inside the organ (either directly or inside a balloon) and laser treatment of the organ lining. New methods and devices may be desirable for effecting hollow body cavity ablation.

SUMMARY

Methods and devices are provided for effecting hollow body cavity ablation. The devices are adjustable to fit the perimeter of a variety of organ sizes and to fold into a small size for insertion into a small opening.

Any of the above embodiments may be used alone or together with one another in any combination. Inventions encompassed within this specification may also include embodiments that are only partially mentioned or alluded to or are not mentioned or alluded to at all in this brief summary or in the abstract.

BRIEF DESCRIPTION OF THE FIGURES

The patent or application file contains at ;east one drawing executed in color. Copies of this patent or patent application publication with color drawing(s) will be provided by the Office upon request and payment of the necessary fee.

In the following drawings like reference numbers are used to refer to like elements. Although the following figures depict various examples of the invention, the invention is not limited to the examples depicted in the figures.

FIG. 1D shows a drawing of an embodiment of electrode activation for an embodiment of a hollow body ablation device having 6 electrodes and two modes;

FIG. 3B is a partial cutaway view of an embodiment of a hollow body ablation device;

FIG. 7 shows a front elevation view of an embodiments of the outside of the handpiece on FIG. 6A, including length and width adjustments;

FIGS. 16 and 17 show Tables 2A and 2B, which show test results of the ablation;

FIG. 21C includes a table showing the depth of necrosis in different segments of the five uteri after treatment using the hollow body ablation device.

DETAILED DESCRIPTION

Figure 1A:
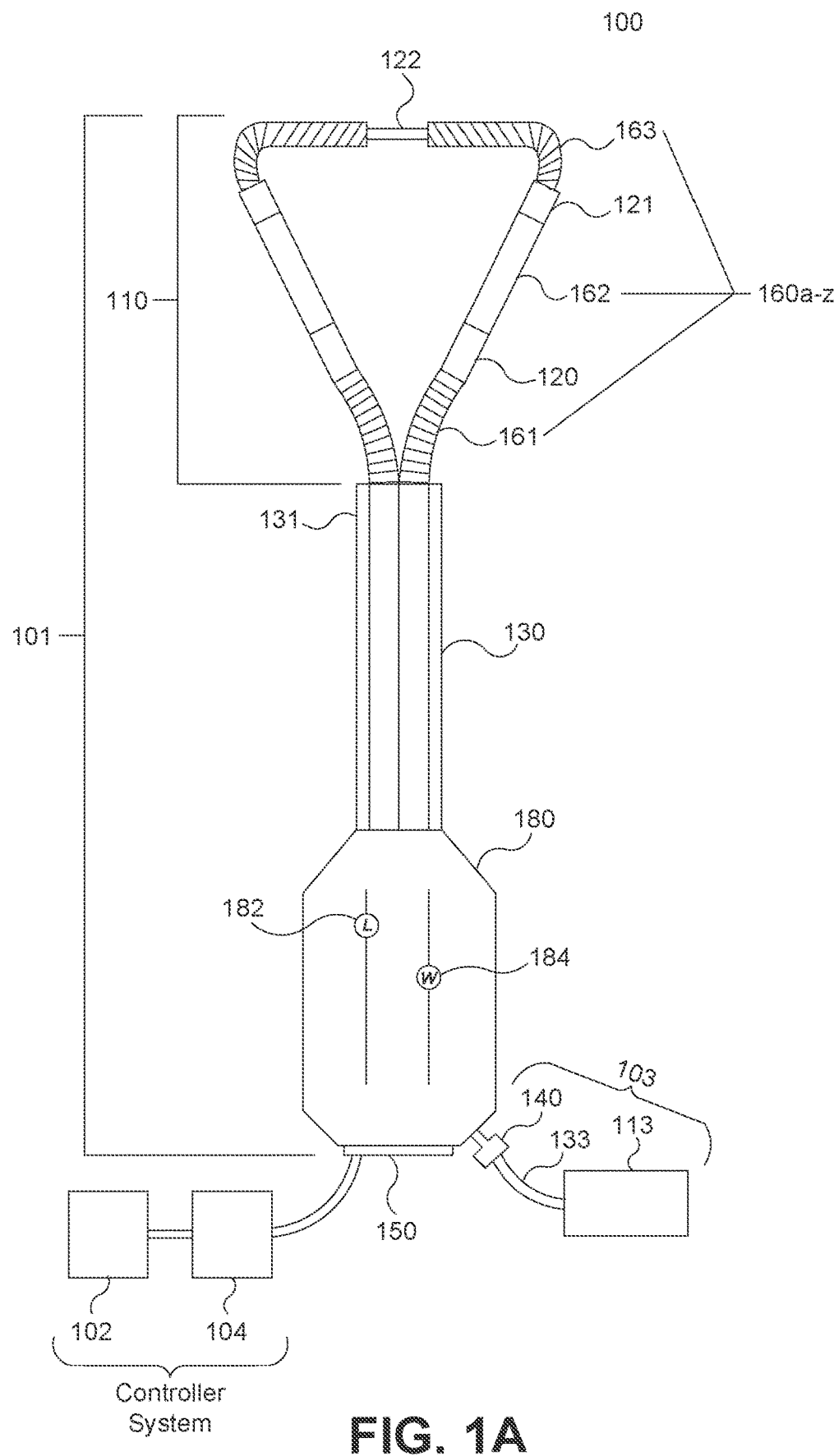
FIG. 1A shows a front elevation view of an embodiment of a hollow body ablation device attached to a controller system and a fluid removal device.

Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

In general, at the beginning of the discussion of each of FIGS. 1A-8 is a brief description of each element, which may have no more than the name of each of the elements in the one of FIGS. 1A-8 that is being discussed. After the brief description of each element, each element is further discussed in numerical order. In general, each of FIGS. 1-17 is discussed in numerical order and the elements within FIGS. 1-17 are also usually discussed in numerical order to facilitate easily locating the discussion of a particular element. Nonetheless, there is no one location where all of the information of any element of FIGS. 1A-17 is necessarily located. Unique information about any particular element or any other aspect of any of FIGS. 1A-17 may be found in, or implied by, any part of the specification.

In various places in discussing the drawings a range of letters, such as "a-z" are used to refer to individual elements of various series of elements that are the same. In each of these series, the ending letters are integer variables that can be any number. Unless indicated otherwise, the number of elements in each of these series is unrelated to the number of elements in others of these series. Specifically, even though one letter (e.g. "a") comes earlier in the alphabet than another letter (e.g., "e"), the order of these letters in the alphabet does not mean that the earlier letter represents a smaller number. The value of the earlier letter is unrelated to the later letter, and may represent a value that is greater the same or less than the later letter.

FIG. 1 shows an overhead view of an embodiment of a hollow body ablation apparatus used in methods of ablation of hollow body organs. The ablation apparatus 100 may include a handheld implement 101, a power supply 102, a controller system (a controller) 104, and an aspirator device 103. The handheld implement 101 may include a head 110, a reservoir 113, a connector 150, an aspiration port 140, a sheath 130, an aspiration tube 133, one or more insulators 120, 121, and 122, one or more electrodes 160, a handpiece 180, a length adjustment 182, and a width adjustment 184 for deploying the device. Ablation apparatus 100 may also include foot control 186. In other embodiments the ablation apparatus 100 and/or handheld implement 101 may not have all of the elements or features listed and/or may have other elements or features instead of or in addition to those listed.

In this application the term "perimeter" when used in reference to the uterus refers to outside of the ablation region or endometrium. The ablation apparatus 100 is an example of a system that can be used for ablation of the interior lining of a body organ that may be hollow. The ablation apparatus 100 may include electrodes that can be arranged in a pattern that makes contact with the surface area of the cavity of the hollow body organ in close proximity to the perimeter. Energizing the electrodes can result in a complete or partial ablation of the lining of the body cavity without the necessity of moving the electrodes, even though the electrodes only make contact with the surface area of the organ in proximity to the perimeter. The user of ablation apparatus 100 may be anyone who uses the ablation apparatus 100 during a hollow body ablation procedure. Users may include doctors, surgeons, nurses, veterinarians, and any support staff that might be helping with a procedure, for example. The procedure may be done in an operating room or as an outpatient procedure, for example.

The handheld implement 101 can be used for ablation of a hollow cavity with anterior and posterior surfaces while the anterior and posterior surfaces are either separated or contacting one another. The handheld implement 101 may include a head 110, which may have any shape, according to the cavity that is intended to be ablated, and/or can be adjusted to approximate the perimeter of a hollow body organ. The handheld implement 101 can have electrodes arranged in a pattern that allow for placement in the perimeter of the hollow body organ. The handheld implement 101 has controls (e.g., on the handheld implement 101) that allow the user to reduce the overall profile and size of the handheld implement 101 to allow for minimally invasive access, to be able to better conform to organs with distorted cavity shapes. The handheld implement 101 has the advantage that handheld implement 101 is able to collapse on itself to form a small tube that will fit into a small diameter aperture. In some embodiments, the aperture has a diameter between about 4 and about 7 mm, including but not limited to 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, and 6.9 mm. In the case where the diameter is between 4 and 7 mm, the handheld implement 101 can collapse upon itself until handheld implement 101 has a diameter of between about 4 or 5.5 and about 7 mm, including but not limited to 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, and 6.9 mm. In some embodiments, the diameter of the aperture is about 5.5 mm and the diameter of the handheld implement 101 when collapsed is less than 5.5 mm, which is smaller than the diameter of heads of prior art ablation devices.

The handheld implement 101 in the invention can have various geometric adjustments applied through operating controls on the handpiece 180 of the handheld implement 101 that change the size and/or shape of head.

The power supply 102 may include a transformer for converting the voltage and/or an alternating current source, such as a variable oscillator, which may generate Radio Frequency (RF) Alternating Current (AC). Alternatively, power supply 102 may include a generator. The power supply 102 controls the frequency of the alternating current that is output by power supply 102.

The aspiration device 103 includes an aspiration tube 133 and a reservoir 113 and may act to remove excess fluid, (i.e. liquid, vapor and gases), from the hollow body organ before, during and/or after the process of ablation (e.g., the procedure) (it is not necessary to remove all fluids from the cavity). The aspirator device 103 can use any method of fluid removal, including a pump, suction, and/or aspirator to remove the fluids.

The controller 104 may include an algorithm that allows for the control of the alternating current (AC). The power supply 102 may be a part of the controller 104 or separate from the controller 104. The controller 104 may be capable of applying different patterns of alternating the polarities of the different electrodes of ablation apparatus 100, changing electrode polarities in various combinations to effect bipolar ablation between selected electrodes or monopolar ablation to a neutral electrode. The frequency, voltage, and/or current may be adjusted to fit the cavity dimensions to limit the ablation effects to the desired tissue or tissue layers, and minimize collateral effects, and can be used to determine overall therapeutic energy doses, and/or determine other settings such as power, duration (the amount of time) of application of the electric field, etc. In at least one embodiment, the electrode bipolar coupling pairs establish electric fields, which cause electric currents to flow through the fluid in the uterine cavity. In addition to at least some resistive heating of the tissue, as a result of the electric currents passing through, the fluid in the uterine cavity is heated, which in turn heats the tissue. The fluid may be heated by one or more of several mechanisms. In at least one embodiment, heat from the resistively heated tissue is carried by the fluid to other tissues that are not heated to the same degree as a result of resistive heating. Additionally or alternatively, the fluid itself experiences some resistive heating. Additionally or alternatively, particles in the fluid having a charge induced by the electric field and/or that had a charge prior to application of the electric field tend to flow in a direction determined by the electric field causing mechanical motion, which may add additional heat. Additionally or alternatively, the presence of the electric field pulls the positive and negative charges further apart, creating a dipole moment. Particle with an induced dipole moment or that already had a dipole moment tend to align with the electric field. As the electric field alternates direction as a result of an AC electrical source, the dipole tend to flip direction to align with the electric field, which creates further mechanical motion, which may add additional heat. See FIG. 1D for a diagram of electrode bipolar coupling pairs and FIGS. 16 and 17 for the energy delivery algorithms that can be used.

The power supply 102 and controller 104 are capable of driving multiple electrodes in various bipolar pairs located in the handheld implement 101 and in proximity to the perimeter of the hollow organ, so as to automatically sequence through a desired set of bipolar or monopolar ablation polarities and/or algorithms. The controller 104 is discussed in more detail in conjunction with reference to FIG. 2.

In some embodiments, the head 110 is a generally triangular handheld implement 101 having an approximately isosceles triangular shape. The area distal to the handpiece 180 is the base. However, even when the head 110 is a parallelogram shape, the base can still be thought of as the side distal to the handpiece 180. If the head 110 has a more circular or oval shape, the base can be thought of as the area most distal to the handpiece 180. Upon full opening of the head 110, the base can be between about 2 and about 4.5 cm and the length upon full opening of the head 110 between about 4 and about 6.5 cm. Other embodiments of this device can have generally larger or smaller base width and length ranges, depending on the size of the organ being ablated. The term generally triangular, means that the handheld implement 101 can be any shape, such as a generally triangular shape (including a rounded triangle), a square, a parallelogram, a circle, ellipse, rhombus, spiral, etc. In at least one embodiment, in the case of the square, parallelogram, circle or ellipse, the "base" is the side most distal from the handpiece and the "sides" are the pieces on either side of the "base." The shape may depend in part on how far apart the sides are in the sheath 130 and/or handpiece 180. In some embodiments, the base is the most distal side from the handheld implement 101 and upon full opening of the handheld implement 101, the base can be between about 1.5 or 2 and about 5 cm, including but not limited to 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, and 4.9 cm. In some embodiments, the sides of the device are between about 3.5 and about 7 cm, including, but not limited to, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, and 6.9 cm.

The reservoir 113 may be a part of aspirator device 103, and may be any type of reservoir that may contain body fluids (i.e. liquids, vapors or gases) without spreading biohazards. In some embodiments. The pump, 214 in FIG. 2, can be any pump. In some embodiments, the pump is a mechanical pump, a finger pump, a syringe pump, vacuum canister, turbine pump, peristaltic pump or other method for creating a negative pressure. Alternatively, the system can be connected to wall vacuum that exists in the hospital or surgical suite.

In the embodiment shown in FIG. 1A, there are multiple insulators 120, 121, and 122 that function to keep the electrodes 160 from touching and possibly shorting out. The electrode shells may be continuous, or slotted on one or more sides or in a generally spiral pattern to facilitate bending and adaptation to the organ perimeter. The side insulators 120, 121 and 122 walls may be continuous, or slotted on one or more sides or in a generally spiral pattern to facilitate bending and adaptation to the organ perimeter. The electrode cross sections may be of any geometry, including circular, elliptical, rectangular, or nonsymmetric 'D' shaped which may be preferable for maximizing electrode surface area for contact with the organ wall for a device which must be introduced through a small diameter aperture. Similarly, the cross sections of the side insulators 120, 121, and 122 in FIG. 1A may be of any geometry, including circular, elliptical, rectangular, or non symmetric 'D' shaped. The insulator cross sections may match that of the electrodes so that if, for example the electrode cross sections are 'D' shaped and slotted, the insulators 120, 121 and 122 are D-shaped and function to separate the slotted D-tube electrodes 161 from the D-tube electrodes 162. The side insulators 120, 121, and 122 may also be hollow to allow push/pull wires and/or signal wires and conduits or tubes to be inserted through. The side insulators 120, 121, and 122 can be constructed of Polyether Ether Ketone (PEEK) or any other non-conductive insulator material. The melting temperature of side insulators 120, 121, and 122 should be high enough so as not to melt during ablation (e.g., it may be desirable that the melting temperature of the insulator be higher than 400 degrees Fahrenheit).

In the embodiment shown in FIG. 1A, there are corner insulators 121a-z that can be rigid D-shaped insulators and function to separate D-tube electrodes 162 from coil electrodes 163. The corner insulators 121a-z can be constructed of polyimide or any other non-conductive insulator.

In the embodiment shown in FIG. 1A, there is a distal insulator 122 that can be constructed of a strip of non-conductive material. The distal insulator 122 functions to separate the coil electrodes 163 and to give the electrodes 163 single plane flexibility. The distal insulator 122 can also be highly flexible to fold to allow the two base electrodes 163 to fold up themselves when the head 110 is collapsed and inserted into the sheath 130.

The handheld implement 101 can have various geometric adjustments applied through operating controls on the handpiece 180 of the handheld implement 101. The operating controls may allow for adjusting the electrodes 160 to fit the perimeter of organs of various sizes and shapes. For a triangular shaped hollow organ cavity such as the human female uterus, the adjustments can be configured to allow independent adjustment of the base and length of the triangle. For an elliptical shape, the adjustments could be major and minor elliptical dimensions. For cavities of other shapes, the appropriate dimensional adjustments can be implemented. The adjustments to fit the cavity dimensions can be used to determine overall therapeutic energy dose in Joules, or other settings such as power, time, etc.

The sheath 130 can be attached to the handpiece 180 and functions to shield the electrodes 160 while the handheld implement 101 is being inserted into an aperture of a hollow body organ (when the device is collapsed). The sheath 130 can shield at least the side electrodes (161, 162) or all electrodes 160 during insertion of the device through the organ aperture. The sheath 130 can be constructed to have an atraumatic tip. When collapsed, the head 110 can slide into the sheath 130. Alternatively, the user can slide head 110 out of the sheath 130 as much as desired during a procedure. The sheath 130 can be attached, via a rigid coupling, to length adjustment 182 (e.g., knob or attachment), such that moving the length adjustment moves the sheath in the same direction by the same amount as the movement of the length adjustment.

The tube 133 may be a part of aspiration device 103, and may carry fluids from the cavy to reservoir 113. In some embodiments, the tube 133 is attached to a small pump that allows for mechanically pumping the fluid into the tube 133 and collecting the fluid in the reservoir 113. The tube 133 can be constructed of any material that is rigid enough to form a tube and allows for sterilization. In some embodiments, the tube 133 is composed of plastic, rubber, or metal. The tube 133 can be inserted through the handheld implement 101 and sheath 130 to allow insertion through the organ aperture during the procedure. In an embodiment, tube 133 and reservoir 113 form a complete seal such that air cannot enter the reservoir 113 during the process of ablation.

The aspirator port 140 located on the handpiece 180 is connected to an aspirator device 103, via tube 113 (and aspiration device 103 may include a vacuum source used to evacuate the uterus from any body fluids created from the procedure, for example).

Optionally, connector 150 may be located on the handpiece 180 and functions to connect the electrodes 160 to the power supply 102, which supplies the RF Energy. The connector 150 may comprise at least one wire per electrode 160. The wires can connect from the electrodes 160, through the sheath 130 to the handpiece 180 and then out the connector 150 to the power supply 102. The connector 150 can be a plug-in having 6 or more tines. However, connector 150 is not necessary.

The electrodes 160 function to apply the RF power to the organ and/or lining of the organ. Each electrode 160 has its own lead (wire) that connects the electrode to the power supply 102. In general ablation apparatus 100 contains segmented electrodes 160 interspersed with insulators 120, 121, and 122. In some embodiments, the segmented electrodes 160 are configured on the head 110 in a shape that mimics the shape of the hollow body organ. In different embodiments, head 110 may have different shapes. The shape of the head 110 can include a generally triangular shaped, circular shaped, oval-shaped, and/or trapezoidal shape. By generally, this means that the shape can be somewhat rounded, meaning that the corners are not pointed, but are rounded. An example of a trapezoidal shape includes, for example, a square edge at the distal end from the handpiece 180 and a triangular edge at the proximal edge to the handpiece 180.

The electrodes 160 can be any type of electrodes known in the art, including slotted D-tube electrodes 161, D-tube electrodes 162, coil electrodes 163, braided metal tube electrodes, bead-chain electrodes, point electrodes, and metallic accordion electrodes (examples can be seen in the other embodiments herein).

In some embodiments, ablation apparatus 100 contains from about 3 to about 50 electrodes, including 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, and 49 electrodes 160. In the embodiments, shown in FIG. 1, there are six electrodes 160 located on the distal end (e.g., the base) of ablation apparatus 100.

The electrodes 160 can be configured along the perimeter of an opening formed by head 110 (e.g., the perimeter of a triangle for a head designed for ablating the uterus). In an alternative embodiment, there may also be electrodes throughout the middle (e.g., on a line bisecting the triangle and/or throughout ablation apparatus 100 on a fan-like arrangement) and/or on the base of ablation apparatus 100 (e.g., base of the triangle). However, by keeping the electrodes only on the perimeter of the opening (so as to be deployed on the perimeter of a body cavity), the diameter head 110 while folded and the diameter of sheath 130 can be kept smaller than when there are electrodes within the opening formed by the head, so that inserting the sheath into the cavity creates less discomfort to the patient and is less invasive. The electrodes 160 function to deliver the RF energy to the tissue. By maximizing the circumference and therefore the area of the electrodes, the charge on the electrodes is spread out over a larger area, and therefore less concentrated. The larger surface therefore makes it less likely that the electrodes will char the uterus or another hollow organ during ablation. In the case where the electrode dimensions are round and tubular, only the outermost semicircular surface of each round tubular electrode is in contact with the perimeter of the surface area of the hollow organ, with the innermost semicircular area not contributing to effective contact. In the case of the round a tubular, it is possible to remove the innermost semicircular region to form a tubular electrode with a "D" cross section. The "D" cross section allows for efficient packing of right and left halves of the head 110 (e.g., electrodes 160 when folded up prior to deployment, reducing the overall dimensions of the handheld implement 101 for either insertion through a natural orifice, or through an incision. This can be important when attempting to minimize handheld implement 101 cross-sectional area for minimal trauma to the patient or to reduce anesthesia requirements to control pain. The cross section of two circular electrodes within a tube of radius r can be calculated as follows. Each electrode has a radius or r/2, and each has a circumferences of $2(r/2)\pi=r\pi$. The surface area of each these electrodes is $Lr\pi$. If the same tube is filled with two D-shaped electrode, each D shaped electrode can have a circumference of $2r\pi/2+2r=r\pi+2r=r(\pi+2)$, and the surface area is $Lr(\pi+2)$. The ratio of the largest part of D-shaped electrodes to the largest pair of circular electrodes that fits into the same tube is $2Lr(\pi+2)/(2Lr\pi)=1+2/\pi=1.6366{\sim}1.64$. Thus, the D-shaped semicircular electrodes have about a 64% larger surface area than the circular electrodes. However, if the corners of the D are rounded, although the D-shaped electrodes will still have a larger surface area, the D-shaped electrodes will not have a 64% larger surface area. Since in particular, it is believed that the pain associated with requiring dilation of an elastic natural orifice, in particular the uterine cervix, is dependent on the diameter of the dilated orifice, the D-shaped electrodes cross-sectional geometry allows for a greater contact area with the hollow body organ tissue without the additional pain associated with the further dilation required by a folded device cross sectional area of two circular tubes. Thus, in some embodiments, the electrodes are D-tube electrodes (161, 162), which make it easier to configure the ablation apparatus 100 to close up into a compact structure and which reduces the density of the energy at the electrodes, thereby allowing the electrodes to deliver a large amount of energy to the uterus for ablation. Using the D-shaped electrode the cross sectional area of the sheath holding the head while the head is folded is minimized or at least reduced to be significantly less than would be required for electrodes having a circular cross section to achieve a similar quality of ablation (e.g., depth of ablation in the center other of the head without charring or otherwise over heating the perimeter). Other noncircular shapes that reduce the necessary diameter of the sheath that holds the head could be used.

The handheld implement 101 can collapse upon itself using any methods known in the art. The embodiment in FIG. 1A, shows a method that involves pulling the side of the electrode portion of the device of head 110 into a sheath 130, which folds insulator 122 and causes electrodes 162 to meet one another and electrodes 163 to meet one another and electrodes 161 to meet each other. In some embodiments, the handheld implement 101 may have push/pull wires attached to the inside of the distal portion of the slotted D-tube electrode 161 on the round side. Pushing on these wires would cause the D-tube electrodes 162 to bend outward, causing the overall width of the handheld implement 101 to increase. In some embodiments, an insulating layer is attached to the flat sides of the slotted D-tube electrodes 161 and/or D-tube electrodes 162 and/or coil electrodes 163 to keep the D-tube electrodes from shorting out when the handheld implement 101 is collapsed and/or from shorting in the region near the opening of the sheath while deployed.

In some embodiments, there are two coil electrodes 163 along the distal edge of the handheld implement 101 (distal from the handpiece 180). The two coil electrodes 163 allow for lateral expansion and refraction. Tubular electrodes along the side 160 can alternate with coil electrodes 163.

To increase the penetration of the radio frequency energy without causing charring of the tissue surface near the electrodes, it is also possible to cool the electrodes 160 by various means, including running flowing fluid through the ablation apparatus 100 or using gas expansion, phase change, or other means. However, tubes for bringing cooling fluids to the cavity tend to increase the diameter required for the sheath 130.

In the embodiments shown in FIG. 1A, there are two slotted D-tube electrodes 161 proximal to the sheath 130. The slotted D-tube electrode may be a stainless steel D-tube that has cuts in the round side of the "D" which allows the electrode to flex along the flat side of the "D". The slotted D-tube electrodes 161 can be oriented so the flat side of the "D" is pointing towards the middle of the handheld implement 101. In the embodiment shown in FIG. 1A, there are two D-tube electrodes 162 one on each side. The D-tube electrodes 162 are stainless steel D-tubes. The D-tube electrodes 162 can be oriented so the flat side of the "D" is pointing towards the middle of the handheld implement 101. The side D-tube electrodes 162 can be hollow to allow insertion of the electrodes 160 and/or insulators 120, 121, and 122 on the base to adjust the width on the base.

In the embodiment shown in FIG. 1A, there are two coil electrodes 163. The coil electrodes 163 can reside inside the D-Tube electrodes 162 and can be slid out via the width adjustment 184 on the handheld implement 101. The coil electrodes 163 can be D-shaped.

The handpiece 180 functions to allow the user to position the handheld implement 101 to change the shape of the handheld implement 101 and/or to collapse the head 110 (e.g., generally triangular electrode end) of the handheld implement 101. The power supply 102 and/or controller 104 can be connected to the electrodes 160 via a connector 150 on the handpiece 180. While folding, electrodes 163 slide into an opening at one end of insulators 121, and while unfolding, electrodes 163 slide out of an opening at one end of insulator 121. While folded electrodes 161 may be stored in the hollow space within insulators 120, insulators 121, and/or the electrode 162 between insulators 120 and 121. The hollow space within electrode 162 may be insulated so that head 110 is functional while electrodes 163 are partially within the hollow space within electrodes 162, and head 110 is not fully unfolded. Insulating the interior surface of the electrodes 162 allows electrodes 162 to not short with electrodes 163 when not fully unfolded and allows head 110 to adjust to cavities of different sizes, and still be operational.

The handpiece 180 may include a connector 150, an aspirator port 140, the length adjustment 182 and a width adjustment 184 for deploying the device. The length adjustment 182 is located on the handpiece 180 and can be knobs, sliders, etc. The length adjustment 182 functions to change the effective length of the deployed device to accommodate a variety of different sized organs. The length adjustment 182 changes the length of the sides of the generally triangular head of the head 110 and can pull the sheath back, exposing more and more of the device. The length adjustment 182 allows for pushing the sheath 130 completely or almost completely over head 110 to allow for insertion through a small aperture, such as by the use of pull wires, push wires, and/or a combination thereof.

The width adjustment 184 is located on the handpiece 180 and can be knobs, sliders, etc. The width adjustment 184 functions to change the maximum width of the deployed device to accommodate a variety of different sized organs. The width adjustment changes the size of the base of the generally triangular head of the device 110. In the embodiments shown in FIG. 1A, the width adjustment 184 can push out the coil electrodes 163, allowing the device to open up wider (e.g., the base to widen). The width adjustment and/or length adjustment can be attached to pull wires, push wires, and/or a combination of these that are attached to the head 110 at the sides, front or bottom to effect moving of the sides or base. The push and/or pull wires can be inserted through the side electrodes 160 and/or insulators 120, 121, and 122.

Although in the embodiment of FIG. 1A length adjustment 182 and width adjustment 184 are implemented by sliding two knobs within slots that are parallel to one another, in another embodiment (e.g., which will be discussed further below in conjunction with FIG. 7) the knobs may slide is slots that are perpendicular to one another.

Foot control 186 may be used for starting and/or stopping the ablation. By providing foot control 186, both of the user's hands are free for manipulating handheld implement 101 and/or controller system 104.

Figure 1B:
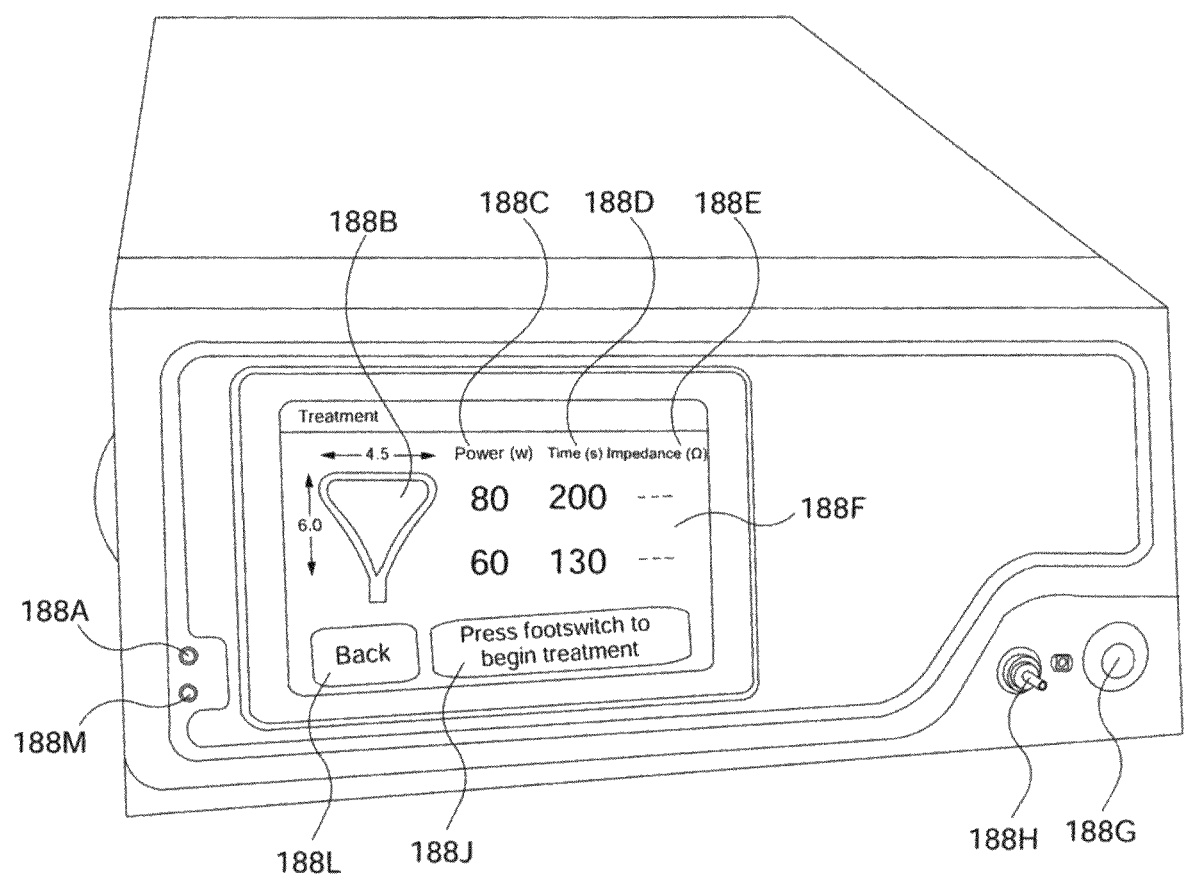
FIG. 1B shows a screen shot of one screen of a user interface of the controller system.

FIG. 1B shows controller system 104 and a page of the user interface associated with controller 104. Controller system 104 of FIG. 1B may include on-light 188a, head image 188b, power column 188c, time column 188d, impedance column 188e, screen 188f, voltage port 188g, aspiration port 188h, instruction box 188j, back button 188l, and warning light 188m. In other embodiments, controller system 104 may have other features in addition to and/or instead of those listed in FIG. 1B.

On-light 188a is a light that may turn on to indicate that controller system 104 is on and/or ablation is currently in progress. Head image 188b is an image of head 110, which indicates the current width and length settings that of controller system 104, which may be used for determining an appropriate power output and duration of ablation for modes 1 and 2. Changing the width and length settings of the head may change the power output and duration of ablation that is determined by controller system 104 to be appropriate. Power column 188c is optional and shows a column of numbers that indicate the power that will be applied during modes 1 and 2 of ablation if the current settings are used (modes 1 and 2 will be described below in conjunction with FIG. 1D). Time column 188d is optional and shows a column showing the duration of time that the power of the corresponding row in the power column may be applied during ablation. In an embodiment, there are two rows. One row (e.g., the top row) contains the power and time associated with mode 1, and the second row (e.g., the bottom row) contains the power and time associated with mode 2. Impedance column 188e is optional, and shows the impedance measured for the region in which the corresponding mode is being applied. In an embodiment, the impedance in the top row is the impedance measured for the region in which mode 1 is being applied, and the impedance in the bottom row is the impedance measured for the region in which mode 2 is being applied. The impedance measurement could be used as an indication as to whether or not controller system 104 is functioning properly. For example, if the impedance is significantly lower or higher than expected for the cavity of interest, it may be an indication that controller 104 is not functioning properly and/or that there is something unexpected present or missing from the cavity of interest. Screen 188f is the screen on controller 104 upon which output information is displayed. Voltage port 188g may be used for connecting handheld implement 101 to controller system 104. The voltage port 188g may deliver the appropriate voltage to the electrodes of head 110 to deliver a desired power for a desired period of time to cause an appropriate ablation of the walls of the cavity of interest. Aspirator port 188h may be used for connecting a tube via which fluids may be evacuated from the cavity of interest. In an embodiment, controller 104 includes a pump that may be used for removing fluids from the cavity of interest. In contrast to other devices, however, it is not necessary to create a vacuum in the cavity of interest to effectively ablate the cavity of interest. Instruction box 188j is optional, and may contain instructions to the user, such as how to start ablation, a parameter was not yet inputted, how to input settings, and/or other messages. Back button 188l may be used to return to a prior screen to enter settings, such as the width and length of the head while in the cavity of interest. Warning light 188m may be used to indicate a problem, such as a short circuit or that a parameter has not yet been entered.

Figure 1C:
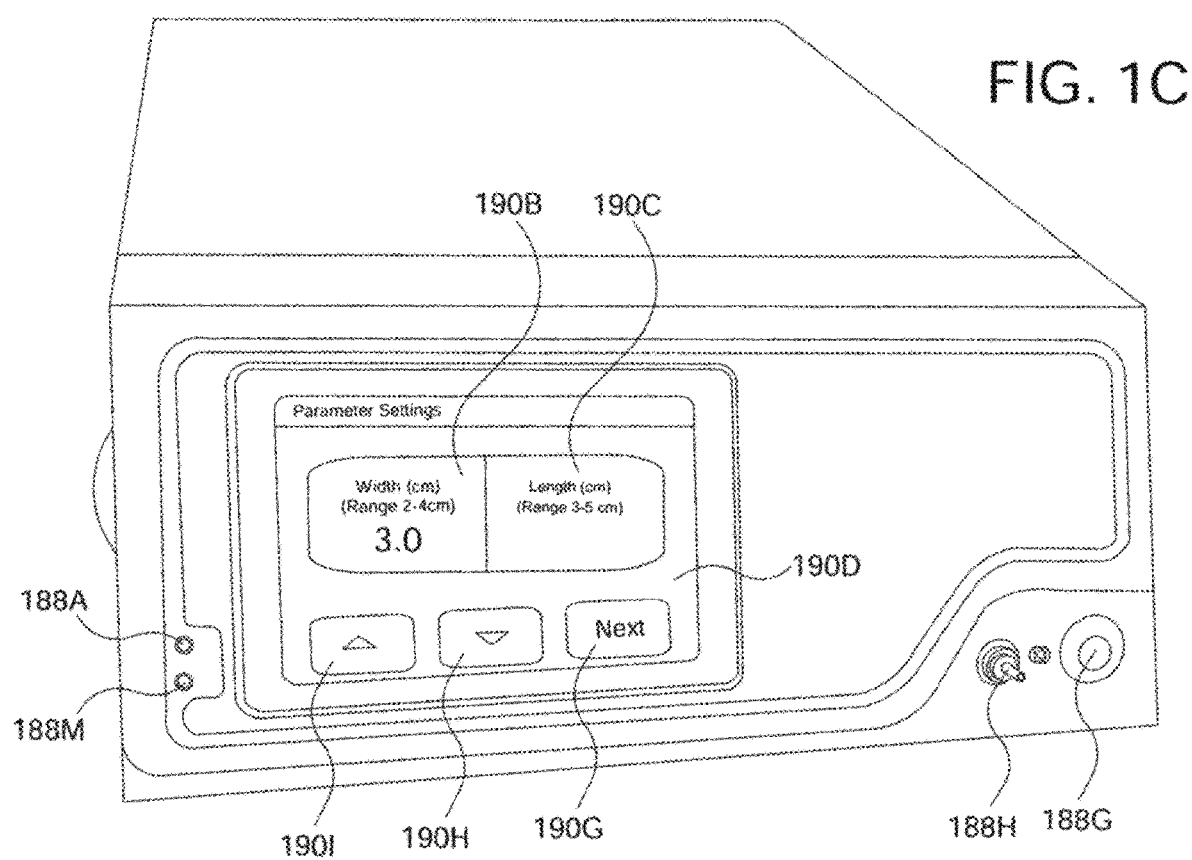
FIG. 1C shows a screen shot of another screen of a user interface of the controller system.

FIG. 1C shows a screen shot of another screen of a user interface of the controller system. FIG. 1C shows on-light 188a, voltage port 188g, aspirator port 188h, instruction box 188j, back button 188l, and warning light 188m, which were discussed above in conjunction with FIG. 1B. FIG. 1C also shows width setting 190B, length setting 190c, screen 190d, decrement button 190h, increment button 190i, and next button 190g. In other embodiments, controller system 104 may have other features in addition to and/or instead of those listed in FIG. 1C.

Width setting 190b may display the width input by the user. Length setting 190c may display the length input by the user. The width and length setting may be entered via a keypad, increment, and/or decrement buttons. Alternatively, the length and width settings may be entered via fields on the display of controller 104 and/or may be determined automatically based on by detecting the positions of the length adjustment 182 and width adjustment 184 (FIG. 1A). Screen 190d may be used for viewing and/or entering the width and length settings of controller 104. Decrement button 190h may be used for decrementing the length and or width setting of controller 104. Increment button 190i may be used for incrementing the length and/or width setting of controller 104. Controller 104 may have a touch screen, keypad, and/or tracking device via which one of the width setting 190b or the length setting may be selected. Upon activation (e.g., by touching the screen or entering input via a tracking device or keypad), decrement button 190h or increment button 190i may be used to decrement or increment, respectively, the current setting that is selected (width or length). Next button 190g may be used to go to the next page of the user interface of controller system 104.

FIG. 1D provides an example in an embodiment in which ablation apparatus has 6 electrodes. In FIG. 1D, the six electrodes are numbered 1-6. Electrodes 161 may be an embodiment of one of electrodes 1 and 6, electrodes 162 may be an embodiment of one of electrodes 2 and 5, and electrodes 163 may be an embodiment of one electrodes 3 and 4 (FIG. 1A). In mode 1, the top four electrodes are activated such that electrodes 3 and 5 have a negative charge while electrodes 2 and 4 have a positive charge, and electrodes 3 and 5 have a positive charge while electrodes 2 and 4 have a negative charge. As the AC current applied to electrodes 2-5 alternates, which pair of electrodes (the pair having electrodes 3 and 5 or the pair having electrode 2 and 4) is positive and which pair is negative alternates. In mode 2, one of electrodes 1 and 6 is positively charged and the other is negatively charged. An alternating voltage is applied to electrodes 1 and 6, such that which of electrodes 1 and 6 is positively charged and which is negatively charged alternates. In an embodiment, first mode 1 is applied to electrodes 2-5, using a particular voltage and duration of time of application, and then mode 2 is applied using a different voltage and for a different duration of time. The region enclosed within electrodes 2-5 is larger then the region between electrodes 1 and 6, and therefore (e.g., during mode 1) voltage is applied for a longer duration of time and/or the voltage applied is higher, when compared to the voltage applied to electrodes 1 and 6 (e.g., during mode 2). Applying more energy and power to electrodes 2-5 than to electrodes 1 and 6 facilitates ablating the cavity without charring or otherwise over ablating the region between electrodes 1 and 6. In an embodiment, the power applied during modes 1 and 2 and the duration of time that the power is applied during modes 1 and 2 is given in Table 1, below.

TABLE 1

Parameters for Power (watts) and Time (seconds)

| W(cm) × L(cm) | 4.0 | 4.5 | 5.0 | 5.5 | 6.0 | 6.5 |
|---|---|---|---|---|---|---|
| Mode 1 Power (W) | | | | | | |
| 2.0 | 58 | 59 | 61 | 63 | 64 | 66 |
| 2.5 | 58 | 59 | 61 | 63 | 65 | 67 |
| 3.0 | 58 | 59 | 61 | 63 | 66 | 69 |
| 3.5 | 60 | 62 | 63 | 66 | 69 | 72 |
| 4.0 | 65 | 67 | 68 | 71 | 74 | 77 |
| 4.5 | 70 | 71 | 73 | 75 | 78 | 82 |
| Mode 2 Power (W) | | | | | | |
| 2.0 | 18 | 23 | 28 | 32 | 37 | 42 |
| 2.5 | 18 | 23 | 28 | 32 | 37 | 42 |
| 3.0 | 18 | 23 | 28 | 32 | 37 | 42 |
| 3.5 | 20 | 24 | 28 | 33 | 37 | 42 |
| 4.0 | 23 | 27 | 30 | 34 | 38 | 42 |
| 4.5 | 26 | 29 | 32 | 35 | 39 | 42 |
| Mode 1 Time (sec) | | | | | | |
| 2.0 | 60 | 60 | 60 | 60 | 60 | 60 |
| 2.5 | 72 | 72 | 72 | 72 | 72 | 72 |
| 3.0 | 84 | 84 | 84 | 84 | 84 | 84 |
| 3.5 | 96 | 96 | 96 | 96 | 96 | 96 |
| 4.0 | 108 | 108 | 108 | 108 | 108 | 108 |
| 4.5 | 120 | 120 | 120 | 120 | 120 | 120 |
| Mode 2 Time (sec) | | | | | | |
| 2.0 | 30 | 30 | 30 | 30 | 30 | 30 |
| 2.5 | 30 | 30 | 30 | 30 | 30 | 30 |
| 3.0 | 30 | 30 | 30 | 30 | 30 | 30 |
| 3.5 | 30 | 30 | 30 | 30 | 30 | 30 |
| 4.0 | 30 | 30 | 30 | 30 | 30 | 30 |
| 4.5 | 30 | 30 | 30 | 30 | 30 | 30 |

In each of the four tables of table 1, the choice of the row is based on the width of the cavity, while the choice of the column is based on the length of the column. The units of widths and lengths are given in centimeters, time is in seconds, and the units of power are in Watts. So, for example, for a uterus that is 3 cm wide and 5.5 cm long, during mode 1, 63 Watts may be applied for 84 seconds, and during mode 2, 32 Watts may be applied for 30 seconds. Table 1 was determined experimentally by placing head 110 a small triangular cavity approximating the uterus between two pieces of meat, then treating meat with head 110, and finally measuring the depth of treating of the meat. The power applied may be determined by iteratively applying a voltage, measuring the current and determining the power for the product of P=IV (power=current times voltage). Depending on whether the power is too high or too low, the voltage is raised or lowered and then the current is measured again and the power is computed again to determine whether the output power is within a desired range. The process of adjusting the voltage, measuring the current and computing the power is repeated until the output power is correct (it may take only a few seconds). Optionally, once the current is measured during the initial iteration, the impedance may be calculated, and the calculated impedance may be used to predict the voltage that will give the desired power output. The optimum values for ablation in humans may be somewhat different than for the meat, but should be similar. In alternative embodiments, electrodes 1 and 6 may be replaced with multiple pairs of electrodes and electrodes 2-5 may be replaced with multiple pairs of electrodes. In alternative embodiments, the cavity may be divided into more than two regions, and there may be more than two modes applied.

Figure 2:
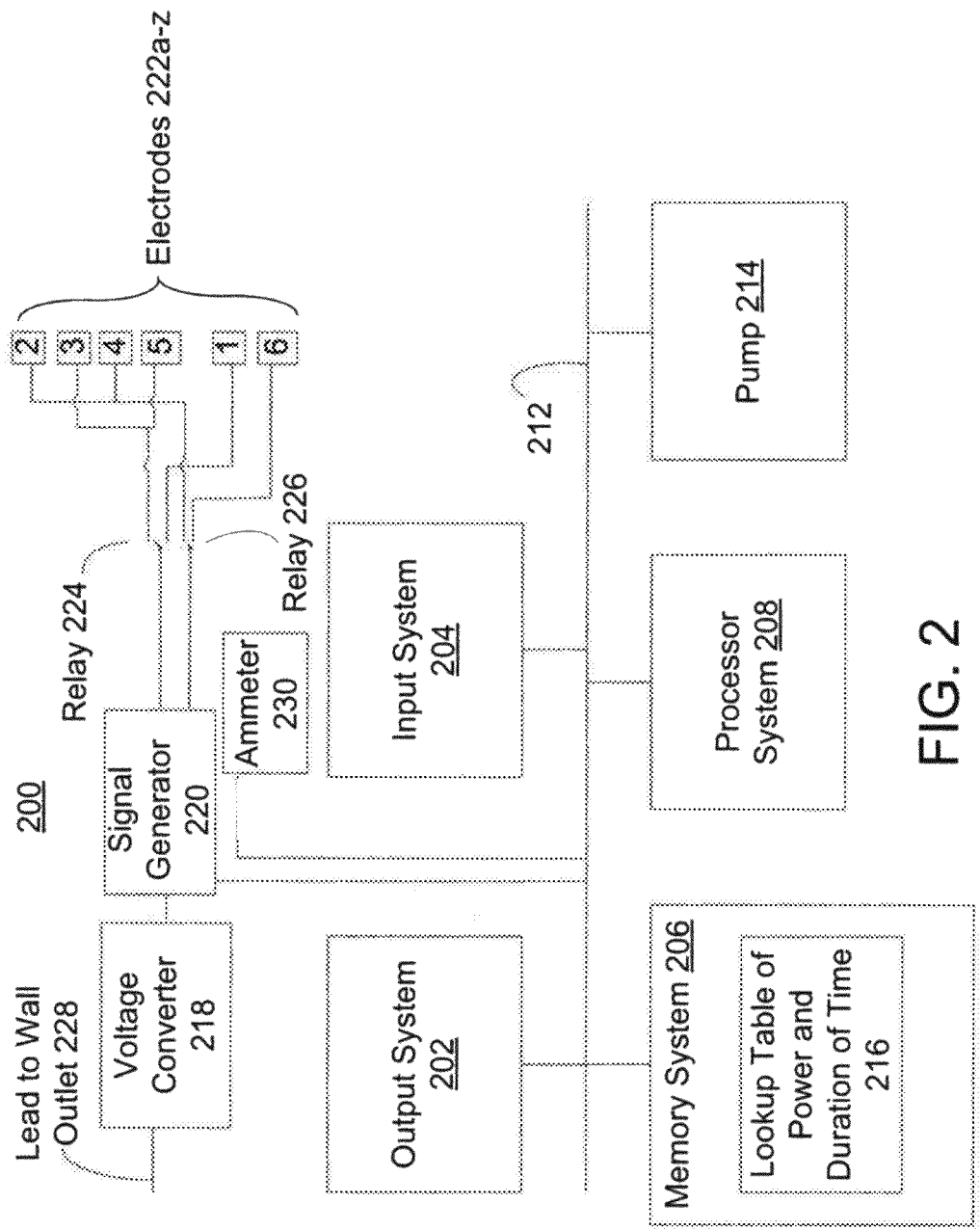
FIG. 2 shows an embodiment of a controller system for a hollow body ablation apparatus.

FIG. 2 shows a block diagram of a controller system 200 used in methods of ablating hollow body organs. The controller may include output system 202, input system 204, memory system 206, processor system 208, communications system 212, vacuum/pressure device 214, algorithm 213, lookup table 216, voltage converter 218, electrode 222 a-z, lead 228, signal generator 220, relay 224, relay 226, and ammeter 230. In other embodiments, the controller system used in methods of ablating hollow body organs 200 may include additional components and/or may not include all of the components listed above.

The controller system 200 is an example of a controller that may be used in the ablation apparatus 100 in combination with the power supply 102 to control the radio frequency (RF) amount and treatment length (see FIGS. 1A and 2). Controller system 200 may be an embodiment of controller 104 (FIG. 1A). In some embodiments, the controller controls the frequency of alternating current (AC) from the RF generator to each electrode 160 (FIG. 1A) in ablation apparatus 100. Alternatively, the controller 200 can control each set of electrodes 160 separately (e.g., the side electrodes and the distal electrodes). With reference to FIG. 1A, the electrodes 160 can be separately controlled through separate wires attached from the electrodes 160 to the power supply 102 and controller 104. In some embodiments, the controller includes an algorithm that allows for the control of the AC to each electrode 160. In some embodiments, the controller 200 makes it possible to utilize electrode polarities of various combinations to effect bipolar ablation between selected electrodes. In some embodiments, the controller 200 makes it possible to utilize electrode polarities of various combinations to effect monopolar ablation to a neutral electrode. The RF power source (FIG. 1A, 102) and controller 200 are capable of driving multiple electrodes in various bipolar pairs located along the handheld implement 101 and in proximity to the perimeter of the hollow organ, so as to automatically sequence through the desired set of bipolar or monopolar ablation polarities (e.g., an algorithm).

In some embodiments, the algorithm designed by the controller is an RF power of between about 30 watts and 90 watts, including but not limited to, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, and 89 watts. In some embodiments, the power is applied for a time of between about 10 seconds to about 200 seconds, including but not limited to, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, and 199 seconds. In some embodiments, the method includes more than one mode and/or algorithm. For example, the two modes may be different modes applied to different electrodes at different times. Examples of these modes are discussed above in conjunction with FIG. 1D. In some embodiments, the user can change the amount of time or power during the procedure based on how the mode and/or algorithm is working on the organ they are currently treating and/or based on the dimensions and/or other characteristics of the cavity being ablated. In some embodiments, the power and time parameters are used as shown in Table 1. The width and length are measured and based on the measurements the appropriate parameters used in each mode. In some embodiments, a frequency of between about 360 and 560 KHz is used, including but not limited to 370, 380, 390, 400, 410, 420, 430, 440, 450, 460, 470, 480, 490, 500, 510, 520, 530, 540, and 550 KHz. For example, in an embodiment, the frequency that is used is 460 Hz. In some embodiments, the current is between about 1.4 and 2.4 amps, including but not limited to, 1.5, 1.6, 1.7, 1.8, 1.9, 2.0, 2.1, 2.2, and 2.3 amps. In some embodiments, the current is between 1.5 and 2 amps.

In some embodiments, the voltage is adjusted and the current measured until the power (P=IV) is at the desired value. The current needs to be measured, because the resistance will vary depending on the individual, but for the uterus is of an order of magnitude of about 20 ohms. The width of the uterus is typically between about 2 and 4.5 cm while the length is between about 4 and about 6.5 cm. The endometrium is between about 5 and about 10 mm thick. Under the endometrium is the myometrium. In some embodiments, the ablation does not heat the myometrium.

Output system 202 may include any one of, some of, any combination of, or all of a monitor system, a handheld display system, a printer system, a speaker system, a connection or interface system to a sound system, an interface system to peripheral devices and/or a connection and/or interface system to a controller system, intranet, and/or internet, for example.

Input system 204 may include a key pad and/or touch screen for entering the dimensions of the cavity of interest (e.g., the uterus). Examples of the keypad and touch screen are discussed further in conjunction with FIGS. 1B and 1C. Alternatively, any one of, some of, any combination of, or all of a keyboard system, a mouse system, a track ball system, a track pad system, buttons on a handheld system, a scanner system, a microphone system (e.g., for a voice activated system), a connection to a sound system, and/or a connection and/or interface system to a controller system, connection to a an external storage device such as an EEPROM, SD, MMC, mini-disk or other storage media or medium located in the handpiece, intranet, and/or internet (e.g., IrDA, USB), for example. Input system 204 allows the user to interact with the controller and RF generator to choose an algorithm, power, and/or time for ablation (e.g., by entering the parameters of the cavity). Alternatively, the user may change or vary an algorithm, power and/or time.

Memory system 206 may include, for example, any one of, some of, any combination of, or all of a long term storage system, such as a hard drive; a short term storage system, such as random access memory; a removable storage system, such as a floppy drive or a removable drive; and/or flash memory. Memory system 206 may include one or more machine-readable mediums that may store a variety of different types of information. The term machine-readable medium is used to refer to any medium capable carrying information that is readable by a machine. One example of a machine-readable medium is a controller-readable medium. Memory system 206 may contain one or more saved algorithms that drive multiple electrodes in various bipolar pairs located along handheld implement 101 and in proximity to the perimeter of the hollow organ, so as to automatically sequence through a desired set of voltages applied to different electrodes of ablation apparatus 100. Memory 206 may store lookup tables, such as Table 1, for the determining the pattern, magnitude, and duration of time of the power applied to the cavity (by applying a voltage to electrodes of ablation apparatus 100). Examples of the algorithm and lookup table are discussed above in conjunction with FIG. 1D.

Processor system 208 may include any one of, some of, any combination of, or all of multiple parallel processors, a single processor, a system of processors having one or more central processors and/or one or more specialized processors dedicated to specific tasks. Processor system 208 may implement the algorithms based on the lookup table of Table 1 that are stored in memory 206 and input received from input system 204.

Communications system 212 communicatively links output system 202, input system 204, memory system 206, processor system 208, vacuum/pressure device 214, and/or signal generator 220 to each other. Communications system 212 may include any one of, some of, any combination of, or all of electrical cables, fiber optic cables, and/or means of sending signals through air or water (e.g. wireless communications), or the like. Some examples of means of sending signals through air and/or water include systems for transmitting electromagnetic waves such as infrared and/or radio waves and/or systems for sending sound waves.

Vacuum/pressure device 214 may be included within, attached to, or be an aspirator device (such as aspirator device 103, FIG. 1A). Vacuum/pressure device 214 may include a pump and may be controlled by processor system 208 and/or the keypad of input system 204 may link directly to vacuum/pressure device 214 for turning vacuum/pressure device 214 on and off.

Lookup Table 216 may include values for the settings of the amount of power and time to be used for a hollow body organ of a certain size, stored in memory system 206. Optionally lookup table 216 may include information about the pattern and/or modes in which the voltages are applied. Lookup Table 216 can allow for looking up the size of a hollow body organ by width and length. Table 1 may be an embodiment of lookup table 216. Alternatively, the Lookup Table, or parts thereof may be located in the Handpiece information storage means. In an embodiment, the catheter may include a chip that could configure the generator power delivery scheme by configuring controller 104 or by controller 104 reading the power settings from the chip on the catheter. Having the lookup table on the catheter or on handheld implement 101 allows more flexible energy delivery schemes since it's generally easier to update a disposable portion of hand unit 101 rather than updating controller 104. For example an EEPROM may store lookup table 216, and the EEPROM may be placed in the connector or the housing of handheld implement 101. The EEPROM only requires 3 wires, and three pins of the connector may be used for the EEPROM.

Voltage converter 218 can convert the voltage from the electrical outlet into the voltage needed for ablation of a hollow body organ of a certain size. Voltage converter 218 may include a transformer and/or power supply.

Signal generator 220 may produce a signal of a particular frequency that works with the algorithm needed for ablation of a hollow body organ. For example, signal generator 220 may decide on the frequency and the magnitude of the voltage based on input from processor system 208, that is sent to each electrode for an amount of time (the modes are discussed in conjunction with FIG. 1D, and the electrodes are discussed below in conjunction with electrodes 222*a-z*).

The electrodes 222*a-z* can function to transfer the signal to the part of the hollow body organ electrodes 222*a-z* are in proximity to. Electrodes 1-6 of FIG. 1D, 161, 162, 163, and/or 160, may be embodiments of Electrodes 222*a-z*. In some embodiments, the electrodes can function in pairs, triplets, quadruplets, quintuplets, or may all function together. In some embodiments, electrodes most distal to handpiece 180 function for a different time and for a different power than the electrodes proximal to handpiece 180 (FIG. 1A).

Relays 224 and 226 may function to relay the signal from the signal generator to one or more groups of electrodes that are included within electrodes 222*a-z*. A relay (e.g., 224 and/or 226) is an electrically operated switch. In an embodiment, relays 224 and/or 226 use an electromagnet to operate a switching mechanism mechanically, but other operating principles are also used. Relays 224 and 226 allow the signals from signal generator 220 to switch which group of electrodes signals are sent. For example, one relay (e.g., 224) may function to send signals to the two electrodes proximal to the handpiece, such as electrodes 1 and 6 during mode 2. The other relay (e.g., 226) may function to send signals to the four electrodes distal from the handpiece, such as electrodes 2-5, during mode 1. Relays 224 and 226 may be replaced with other types of electrical and/or electromechanical switches, such as transistors, threshold diodes, and/or other threshold devices. FIG. 2 provides an example of how the relays can function to send signals separately to different groups of electrodes.

Ammeter 230 measures the current, which is read by processor system 208. Processor system 208 computes the power output based on the voltage setting and the reading from ammeter 230, and adjusts the voltage until the power output is at the desired level as determined by lookup table 216.

Alternatives and Extensions

Figure 3A:
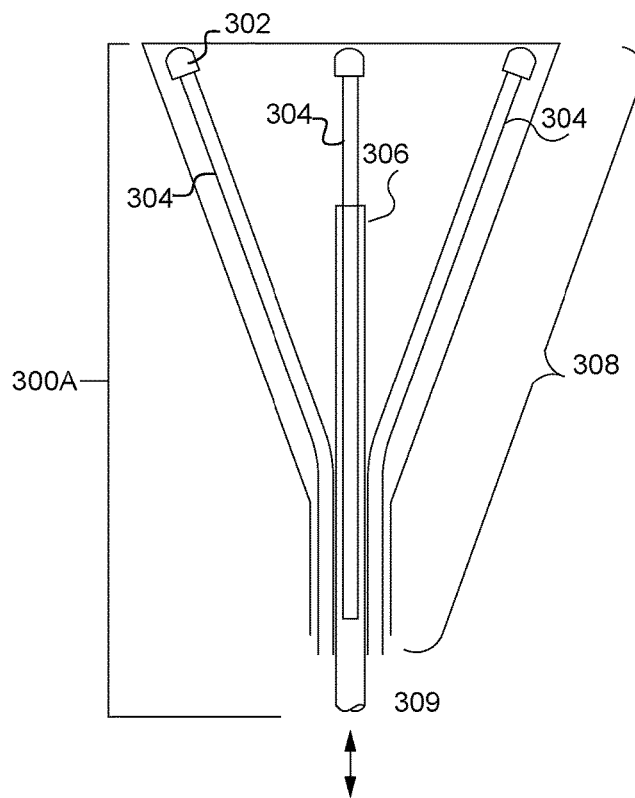
FIGS. 3A-C show front elevation views of three more embodiments of hollow body ablation devices.
Figures 3B, 3C:
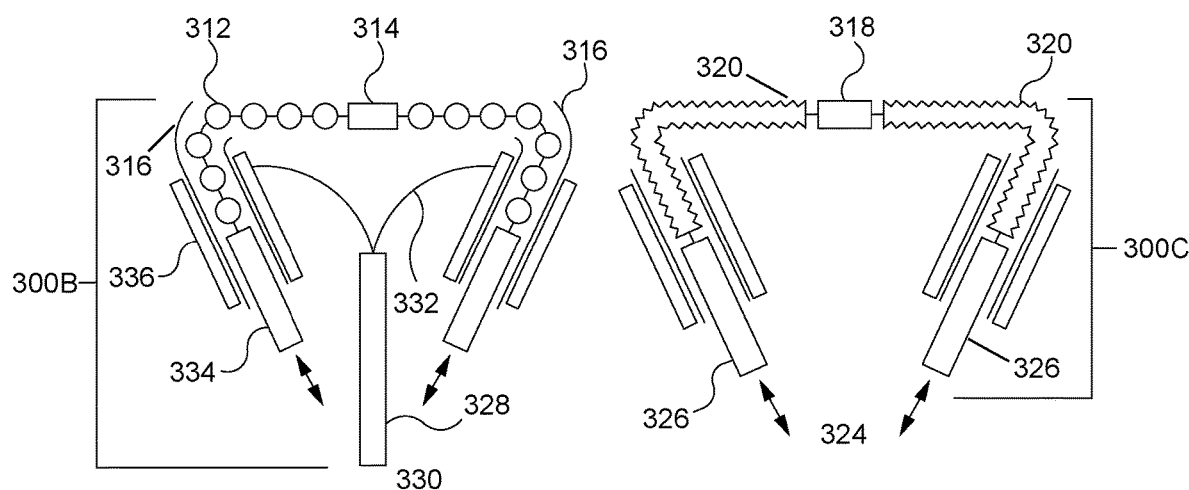
Figure 4:
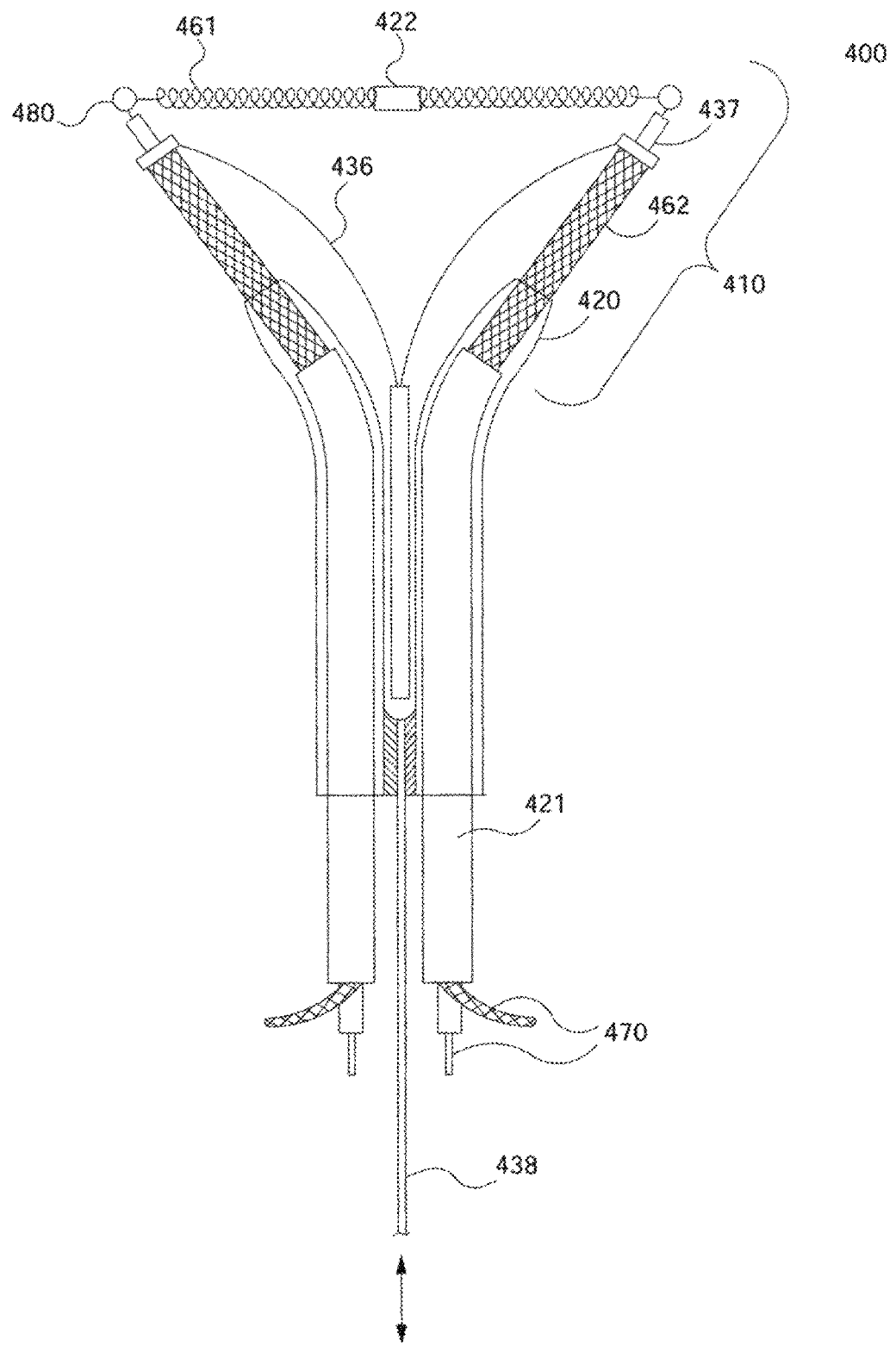
FIG. 4 shows a front elevation view of an embodiment of a hollow body ablation device using extension spring or coil electrodes and push wires.
Figure 5:
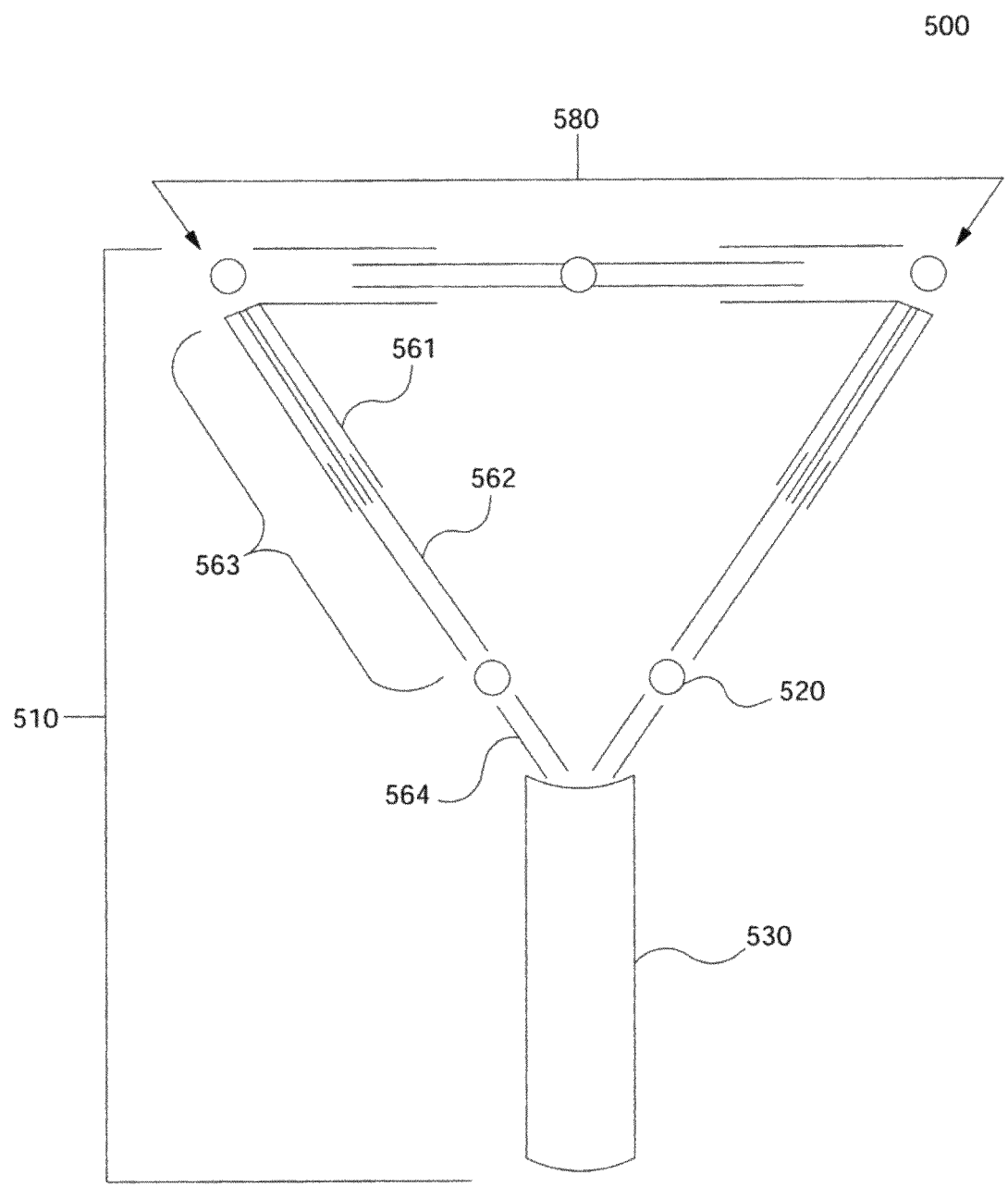
FIG. 5 shows a front elevation view of an embodiment of a hollow body ablation device using telescoping electrodes.

FIGS. 3-5 provide alternative embodiments of the hollow body handheld implement 101 of FIG. 1. In these embodiments, the design, organization, and number of the electrodes can vary. The design and movement of ablation apparatus 100 can also vary. Features of different embodiments can be interchanged with features of other embodiments.

FIGS. 3A-C show overhead views of three embodiments of ablation apparatus 100 used in hollow body ablation apparatuses for methods of ablation of hollow body organs. The figures show embodiments of the ablation apparatus 100 show the head without showing the handpiece associated with the head. In some embodiments, the handpiece could be constructed similarly to how handpiece 180 was described in FIG. 1A.

FIG. 3A shows a head 300A having three separate electrodes 304, the center electrode 304 including a sliding insulation sheath 306. The electrodes 304 also include atraumatic tips 302. Although not shown, the head 300A can also include a handpiece 309. In other embodiments the head 300A may not have all of the elements or features listed and/or may have other elements or features instead of or in addition to those listed.

In FIG. 3A, there are three electrodes 304 that can open up in the cavity of the hollow body organ. The three electrodes 304 can open up similar to a fan. Push or pull wires can be used to pull the outer electrodes toward the central electrode 304. The center electrode 304 includes a sliding insulation sheath 306 which can be pushed up when the head 300A is being collapsed. Alternatively, each of the outer two electrodes 304 can be a D-tube electrode having an insulated layer on the straight edge of the D-tube. The straight edge of the D-tube can be placed closest to the middle one of electrodes 304 on each outer electrode 304. In some embodiments, the sheath 306 can be moved up or down on the central electrode 304 using one or more control knobs on the handpiece 309.

The atraumatic tips 302 on the distal ends of the electrodes from the handpiece function to keep the electrodes 304 from touching the sides of the hollow body cavity aperture. Each electrode 304 can have an atraumatic tip 302 on the end of the electrode 304. In some embodiments, the center electrode 304 can be completely covered by the sheath 306 making it unnecessary for it to have an atraumatic tip 302.

The sheath 306 can act as a sliding insulator to keep the outer electrodes 304 from touching the inner electrode 304. The sheath 306 can be a layer of insulation on the central electrode 304 that can slide down the electrode 304, controlling the flow of energy in the hollow body cavity.

Before treatment, the sheath 306 can be positioned to completely or mostly cover the central electrode 304. Positioning sheath 306 to cover central electrode 306 causes the energy to transfer only at the distal portion of handheld implement 101. After that section of the hollow body organ is fully treated, the sheath 306 can be pulled back, exposing more of the electrode 304 and allowing the newly exposed electrode 304 to treat the tissue. Alternatively, the sheath 306 can be positioned to cover the center electrode 304 while handheld implement 101 is collapsed and inserted through the aperture of the hollow body organ and then the head 300A can be opened (e.g., the electrodes 304 separated) and the sheath 306 removed before the RF energy is applied.

FIG. 3B shows an embodiment of an ablation device 300B that uses sliding bead-chain electrodes 312. Using sliding bead-chain electrodes 312 is an alternate approach, for example, for an endometrial ablation device. The ablation device 300B includes side electrodes 336 (shown cutaway), insulator 314, insulator 316, bead-chain electrodes 312, a central push/pull wire 330, and two side push/pull wires 332. The ablation device 300B can also include a handpiece 309. In other embodiments, ablation apparatus 300B may not have all of the elements or features listed and/or may have other elements or features instead of or in addition to those listed.

The side electrodes 336 can be tubular and hollow in structure and can function to house the bead-chain electrodes 312. The bead-chain electrodes 312 can be a series of metallic beads separated by a thin wire, making the structure very flexible but with a fairly high surface area. The structure of the bead-chain electrodes 312 is similar to what is found on some necklaces and key chains.

The insulators 316 can reside inside the side electrodes 336 and function to insulate the side electrodes 336 from the bead-chain electrodes 312. The insulators 316 can also be attached at the distal end of the device between the two bead-chain electrodes 312.

The push/pull-wires 334 and 328 can be connected to the bead-chain electrodes 312 and allow the user to extend or retract the bead-chain electrodes 312 as needed. The push/pull-wires 334 can pull the sides together to collapse the top two electrodes 312 upon each other creating two straight parallel lines of electrodes 312. A central push/pull wire 332 can be implemented to widen the device 300B. In an embodiment, two sided push/pull wires 332 are made from a flexible resilient material that acts as a spring pushing the head open.

FIG. 3C shows an embodiment of an ablation head 300C that uses metallic accordion electrodes 320. Ablation head 300C is an alternate approach for an ablation device (e.g., an endometrial ablation device). Ablation head 300C can operate very similarly to the sliding bead-chain concept (see FIG. 3B) with the major exception being that, instead of a bead-chain for an electrode, this concept uses a metallic accordion-like structure as the electrode. The accordion structure 320 can be flexible and conductive and can bend as well as change length. Push/pull wires 326 can be used to push the accordion-like electrodes 360 together at the base and/or to push them apart.

FIG. 4 shows an overhead view of an embodiment of an ablation device 400 used in a hollow body ablation apparatus for methods of ablation of hollow body organs. The ablation device 400 uses a central sliding insulator 421 to insulate electrodes 462. The ablation device 400 can use extension spring electrodes 461 for width adjustment and outer pushwires 436 to extend the head 410 from a central push/pull wire 438 attached to a hypotube. The extension spring electrodes 461 and the outer push wires 436 allow for collapsing the head 410 of the device 400 and to change the shape or size of the head 410 of the device.

The ablation device 400 may include a handpiece (not shown), electrodes 460*a-z*, extension spring electrodes 461, braided metallic electrodes 462, insulators 420, fixed insulators 421, two outer push wires 436, braided tube rings 437, tip connections 480, electrical connections 470, and central push/pull wire 438, distal insulating gaps 422, sliding insulators 420, and fixed insulators 421. In other embodiments the hollow body ablation apparatus 400 may not have all of the elements or features listed and/or may have other elements or features instead of or in addition to those listed.

The purpose of the sliding insulator 420 is to direct the flow of energy in the hollow body organ. When the sliding insulator 420 exposes only the distal portion of the braided metal tube electrode 462, energy is only delivered to the distal portion of the organ. When the sliding insulator 420 is pulled back, energy is delivered the newly exposed regions until the full uterus is treated.

In FIG. 4, the braided metal tube electrodes 462 are similar to (or may be) coaxial cables and are positioned on the device 400 as side electrodes. Each braided metal tube electrode 462 can have a non-conductive core, in between the outside wires and the inside wires, that would allow braided metal tube electrode 462 to be flexible. The braided metal tube electrodes 462 can be flexible. The braided metal tube electrodes 462 may also contain a ring 437 to keep the braided tubing from unraveling. The braided metal tube electrodes 462 can be attached to the extension springs 461 via connections 480. The connections 480 can be insulators 420 or can be atraumatic materials.

The distal electrodes 461 are extension spring electrodes that may be located at the distal end of the head (on the base of the device 400). The distal electrodes 461 function to treat the distal region of the hollow body organ (e.g., the fundus region of the uterus). The distal electrodes 461 can stretch to accommodate a variety of widths (e.g., uteri widths). The distal electrodes 461 can include a connection 480 that functions to connect the distal electrodes 461 to the center conductive core of the braided metal tube electrodes 462 (e.g., coaxial cable).

The distal insulating gap 422 functions to insulate the extension spring electrodes 461 from each other. The distal insulating gap 422 becomes the tip of the device 400 upon collapsing. The distal insulating gap 422 can be silicone.

The outer push wires 436 allow for width adjustment by connecting to the distal corners of the device 400. The outer push wires 436 push on distal corners and widen the distal end of the device (the base). The outer push wires 436 can extend the extension springs to increase width of the distal end of the head 410. Activation of outer push wires 436 can be at the proximal end of the device (e.g., the handpiece 180).

The sliding insulator 420 functions to collapse the device 400 and/or to widen the device. The sliding insulator 420 slides on top of the braided metal tube electrodes 462 and directs the flow of energy in the hollow body organ (e.g., uterus). The sliding insulator 420 can be moved by connecting a central push/pull wire 438 to it which can be actuated at the proximal end of the device 400 (at the handpiece 180).

The handpiece 180 can be constructed similarly to any embodiment described herein, for example see FIG. 7 and/or FIG. 1A. The handpiece 180 can contain knobs to allow for sliding of the sliding insulator 420 to cover the braided metallic electrodes 462 and/or to collapse the device 400 for insertion into an aperture of a hollow body organ. The handpiece may also contain electrical connections 170 that connect the electrodes 462, 461 to the RF power source.

FIG. 5 shows an overhead view of an embodiment of an ablation device 500 used in a hollow body ablation apparatus for methods of ablation of hollow body organs. The ablation device 500 uses telescoping electrodes 563 to change the length and/or width and/or to collapse the device 500.

The ablation device 500 may include telescoping electrodes 563, a sheath 530, joints or electrically insulating couplings 580, a head 510, and a tubular electrode 564. In other embodiments the hollow body ablation apparatus 500 may not have all of the elements or features listed and/or may have other elements or features instead of or in addition to those listed.

The telescoping electrodes 563 may include two pieces 561 and 562. Piece 1 562 and Piece 2 561 can fit together as two sleeves, one sliding into the other sleeve. The dotted line on Piece 2 in FIG. 5 shows a wire for delivering electricity to the electrodes. Using piece 2 561, the length of the telescoping electrode 563 can be changed by moving Piece 1 562 up or down.

Piece 1 562 can be a straight line with an inner polymer tube and two outer hypo tubes glued to the inner polymer tube. The inner polymer tube can be between about 4.0 to 4.6 cm long, including but not limited to 4.1, 4.2, 4.3, 4.4, and 4.5 cm long. In other embodiments, the inner polymer tube is about 4.3 cm long. The two outer hypo tubes can be of a length equal to the length of the inner polymer tube minus a small notch. The length of the notch can be about 1 mm to 3 mm, including 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, and 2.9 mm. The small notch can be filled with glue. The length of the outer tubes can be from about 1 to about 2 cm and from about 2 to about 3 cm long with glue filling the middle notch. In some embodiments, the inner tube is approximately 4.3 cm, and the outer hypo tubes are 1.5 cm and 2.5 cm with glue filling the middle notch.

Piece 2 561 can be a longer piece that is generally with one inner tube, an outer tube that covers and is parallel to the inner tube. Piece 2 561 can include a central tube washer or disk with a narrow polymer tube glued in. The outer tube can be a larger diameter SS hypotubes, sized to fit over and "telescope" the smaller SS hypotubes (Piece 1) 562. When piece 2 561 is inserted over Piece 1 562, it can form a two-section adjustable length electrode (a telescoping electrode) 563.

The electrodes 563 can be configured on the head 510 such that the telescoping electrodes 563 are separated from each other by an electrically insulating coupling 520. Two telescoping electrodes 563 are positioned on the base (distal side) of the head 510 separated by a couplings 520a-z. One or two telescoping electrodes can also be placed on either side of the head 510. Alternatively, one telescoping electrode 563 can be placed on each side and one proximal electrode 564 can be placed separated by an electrically insulated coupling 520. The proximal electrode 564 can be 1.5 cm long. The telescoping electrode 563 can vary from about 2.5 cm to about 5 cm (depending on whether Piece 1 562 and Piece 2 561 are pulled apart or pushed together). In some embodiments, the telescoping electrodes on the base can vary from about 2 cm to about 4 cm, depending on whether Piece 1 562 and Piece 2 561 are pulled apart or pushed together.

Two of the adjustable telescoping electrodes 563 can form the sides of a triangular shaped electrode structure 510 (the head). The distal end of the triangle (which is the base of the triangle) can be similarly telescoped to have adjustable width. The sides can also include a tubular electrode 564 separated from the telescoping electrode 563 by an electrically insulted coupling 520. The device 500 can also include a sheath 530 that can be moved up and over the head 510 to collapse the head 510 for insertion into an aperture of a hollow body organ.

Further embodiments of ablation devices can include a collapsible flex circuit with a NiTi strip for support (a stronger wire). The NiTi shape memory alloy strip creates a loop shape to fit a uterus or other hollow body organ. NiTi strips are superelastic fine-grained Nickel-Titanium (NiTi) polycrystalline shape memory alloys.

Further embodiments of ablation devices include, for example, a self-expanding spring device with a 2-4.5 cm width when completely open and 4-6.5 cm length when completely open. The springs can be the electrodes or alternatively, the electrodes can be included as "islands" in the springs (e.g., electrodes can be woven into mesh as islands). Another alternative embodiment of an ablation device includes a metalized foam that acts like an accordion fan.

An Embodiment of the Handheld Implement

Figure 6A:
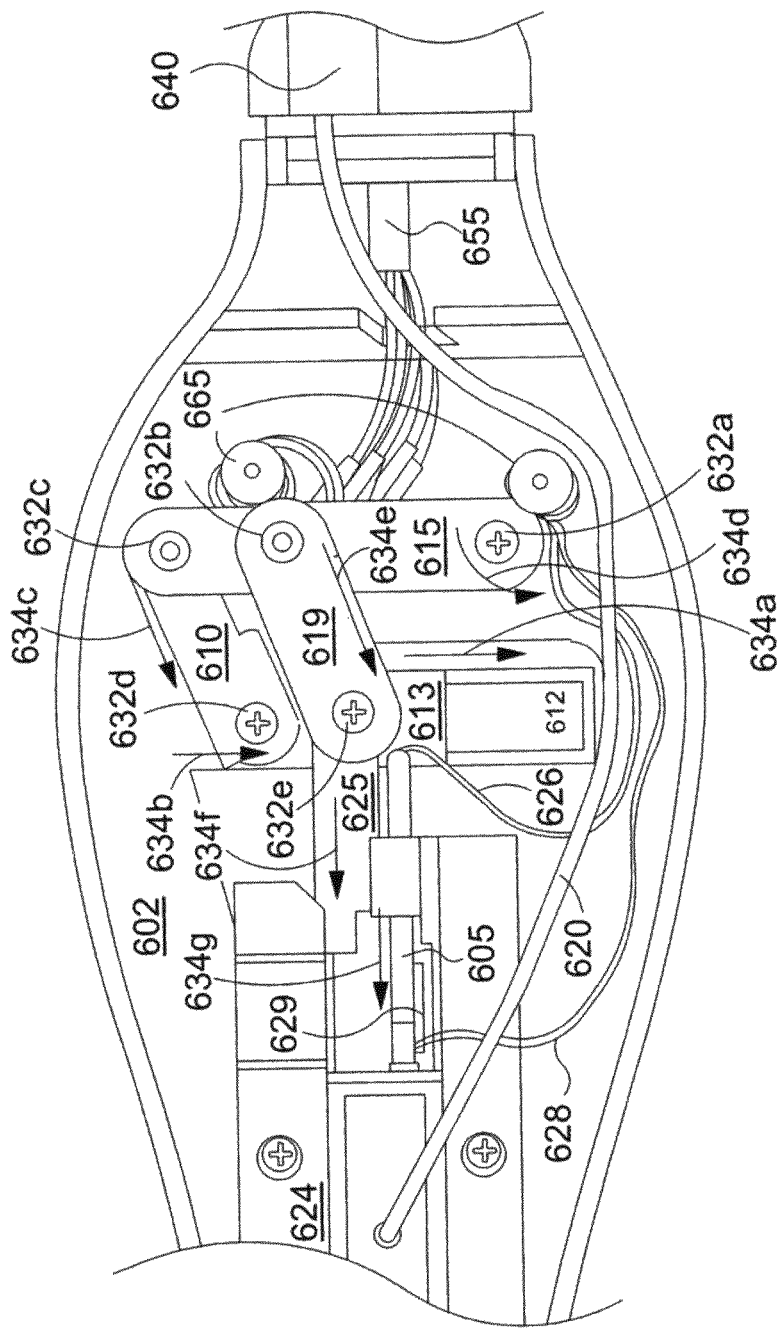
FIG. 6A shows a front elevation view of the inside of an embodiment of the handpiece.

FIG. 6A shows an overhead view of an embodiment of the inside of a handpiece 600 used in an embodiment of a hollow body ablation apparatus for methods of ablation of hollow body organs. The handpiece 600 includes a shell 602, a central tube 605, levers 610, 615, and 619, sliding member 613, width slot 612, aspirator tube 620, chamber 624, sliding piece 625, wires 626, wires 628, length slot 629, joints 632a-e, arrows 634a-g, a vacuum port 640, a sheath 655, and wire post 665. In other embodiments the handpiece 600 may not have all of the elements or features listed and/or may have other elements or features instead of or in addition to those listed.

In short, the length and width adjustments on the handpiece 600 use push/pull wires attached to levers, sliding members and/or the sheath that function to change the length and width of the ablation device and/or to insert it into the sheath. The push/pull wires are attached to the head of the device and are attached to levers and/or sliding members. Knobs on the handpiece are used to move the levers to effect changes in position and/or to collapse the head into the sheath.

Handpiece 600 is another embodiment that may be substituted for handpiece 180. The outer shell 602 of the handpiece can be in any shape known to the skilled artisan. In some embodiments it is in a shape that makes it more comfortable to the user to hold. In some embodiments, it is small enough that the user can hold it with one hand. The outer shell 602 can be made of a material that is sterilizable without changing its shape and/or properties.

The central tube 605 may be slidably attached to a chamber to which the sheath is connected. The central tube 605 may be attached within the sheath (not shown) to push/pull wires for movement of electrodes 3 and 4 (see FIG. 1D) in and out of the insulating tubes separating electrodes 3 and 4 from electrodes 2 and 5. Central tube 605 may be connected to a sliding piece mounted in channels outside of the walls of the chamber. Central tube 605 may slide inward and outward within a hole in one of the walls of the chamber as the sliding piece slides. Central tube 605 may be referred to as a push/pull tube, and central tube 605 is connected to push/pull wires. Pushing and pulling central tube 605 pushes and pulls, respectively, the push/pull wires pushing conductors 3 and 4 out or pulling conductors 3 and 4 in.

Lever 610, width slot 612, sliding member 613, lever 615, and lever 619 are used for changing the width of the head. The width adjustment can be effected by sliding one of the knobs on the outside of the handpiece 600 right or left on the handpiece within a slot 612. The knob is attached to the sliding member 613, which moves levers 610 and 619. The levers are attached to a push/pull wire. The central push/pull wire 438 has a fork or split where the central push/pull wire 438 divides into two outer push wires 436 that are attached to the head/electrodes (3 and 4, FIG. 1D). As the central push/pull wire 438 is pushed, electrodes 3 and 4 slide out of the insulating D-shaped tubes between conductors 2 and 3 and between conductors 4 and 5 (FIG. 1D). As the D-shaped coil electrodes 3 and 4 extend out of the insulator tubes, electrodes 3 and 4 push against one another (via the insulator separating electrodes 3 and 4), causing the head to widen into a triangular shape. Moving the knob in the opposite direction reverses the process bring electrodes 3 and 4 into the insulating tubes attached to electrodes 2 and 5, respectively. Movement of the knob pulls the distal electrodes (e.g., coil electrodes in FIG. 1A) into insulators and/or the sheath. The movement of the width adjustment can be at a right angle to the movement of the length adjustment so that it will be more clear to the user which knob to use for the width adjustment, which may decrease confusion about which knob causes which adjustment. However, in some embodiments, the width adjustment and length adjustment can move in the same direction (see, for example, the embodiment in FIG. 1A).

The length adjustment includes a length slot 629 a sliding member, and a sheath (not shown). The length adjustment can be effected by sliding a knob up or down a slot 629 on the handpiece 600. The knob may be coupled to the sheath with a rigid coupling, such that moving the knob slides the sheath the same distance and in the same direction as the knob. The slot 629 can be positioned on the handpiece parallel to the sheath and, thus, using the slot on the handheld implement 101, the movement of the knob can mimic the movement of the sheath up or down the handpiece. Thus, the knob is moved upward (distally) to lengthen and down (proximally) to shorten. Further, as the sheath moves up, the head can be collapsed to have the two sides of the base parallel to each other so that the majority of the head fits into the sheath. In this case, the knob is moved to the furthest distal position to collapse the head. Smaller movement of the knob results in smaller changes to the length of the head that is unsheathed.

Chamber 624 may be hermetically sealed. Central tube 605 may slide in an inward and outward direction within a hole in one of the walls of chamber 624, thereby changing the width of head 110, if head 110 is at least partially exposed or unsheathed. The sheath may be slidably attached to chamber 624 and may slide in and out of chamber 624 to expose or cover, respectively, portions of head 110, thereby changing the length of head 110 that is exposed.

Sliding piece 625 may be slidably mounted in channels along side chamber 624. Central tube 605 may be fixedly mounted to sliding piece 625, so that when sliding piece 625 slides, central tube 605 slides with sliding piece 625 in the same direction inward or outward with respect to a hole in a wall of chamber 624.

Wires 626 may attach to electrodes 3 and 4, and wires 628 may attach to electrodes 1, 2, 5, and 6 (see FIG. 1D and FIG. 2). Wires 626 may slide with central tube 605 as the width of head 110 is adjusted.

The wires 626 and 628 function to transmit electricity to the electrodes, which may have a frequency in the radio frequency range, for example. As such, the wires 626 and 628 are attached to the electrodes in the head of ablation apparatus 100, and wires 626 are inserted through the central tube 605 while wires 628 enter chamber 624 on the outer side central tube 605 to attach to electrodes 3 and 4 and electrodes 1, 2, 5 and 6, respectively. Wires 626 and 628 may also be attached through a connector to controller 104. In an embodiment, one set of electrodes (e.g., 1, 3, and 5 of FIG. 1D) is connected to the one polarity of the power source and another set of electrodes (e.g., 2, 4, and 6 of FIG. 1D) is connected to the other polarity of the power source, such that as the polarity of the power source alternates, the polarity of the electrodes alternate. In an alternative embodiment, there is one wire per electrode allowing for separate control of each electrode.

Slot 629 may hold the length adjustment knob, and the length adjustment knob may be rigidly connected to the sheath (e.g., via a plastic connector piece). As the length adjustment knob slides up and down slot 629, the sheath may slide up and down covering or exposing, respectively portions of head 110, thereby adjusting the length of the head 110 that is used for ablation according to the dimensions of the cavity. In some embodiments, as the sheath is moved up and over the head of the device, the width adjustment operates to push the sides together and to push the two sides of the distal end together to create a tubular head that can fit into the sheath (e.g., sheath 130 or 530).

Joints 632a-e allow levers 610, 615, and 619 and sliding member 613 to move. In an embodiment, joints 632a-e may be pivots, which may be held in place by screws. Joint 632a attaches lever 615 to shell 602 so that lever 615 rotates about joint 632a. Joint 632b attaches lever 615 to lever 619 so that lever 619 may rotate about joint 632b as lever 610 moves (the movement of lever 615 causes lever 619 to move). Joint 632c attaches lever 610 to lever 615 so that lever 610 and 615 rotate with respect to joint 632c as lever 610 moves (which causes lever 615 to move). Joint 632d connects lever 610 and sliding member 613 so that as sliding member 613 slides, lever 610 rotates about joint 632d. Joint 632e connects lever 619 to sliding piece 625, so that as lever 619 moves (and rotates with respect to joint 632e), sliding piece 625 slides pushing central tub 605. Joint 632e is not connected to sliding member 613.

Arrows 634a-g are direction arrows showing the direction of movement of levers 610, 615, and 619, sliding piece 625, and central tube 605 as sliding member 613 slides in the direction of arrow 634a. Specifically, as sliding member 613 slides in the direction of arrow 634a, one end of lever 610 is pulled, via joint 632, in the direction of arrow 634b (which is the same direction as arrow 634a). As a result, the other end of lever 610 is pulled in the direction of arrow 634c. The movement of lever 610, via joint 632c, pulls on one end of lever 615, which causes lever 615 to rotate about joint 632a (which is at the other end of lever 615) in the direction of arrow 634d. The rotation of lever 615 causes lever 615 to push, via joint 632b, on one end of lever 619 in the direct of arrow 634e. The pushing on lever 615 causes the other end of lever 615 to push, via joint 632e, on sliding piece 625. As a result of the pushing on sliding piece 625, sliding piece 625 moves in the direction of arrow 634f, which causes central tube 605 to move in the direction of arrow 634g (which is the same direction as arrow 634f). Moving sliding member 613 (via moving the width adjustment knob) in the opposite direction of arrow 634a causes movement of levers 610, 615, and 619, sliding piece 625, and central tube 605 to move in the opposite direction as arrows 634b-g, in a similar manner as described above (except pushes are replaced with pulls and pulls are replaced with pushes).

The vacuum port 640 allows for the attachment of a vacuum tube to remove fluid (i.e. liquids, vapors and gases) from the hollow body organ before during and after the procedure. The tube can be placed from the vacuum port 640 through the handpiece to effect fluid removal in the hollow body organ.

The sheath 655 functions to connect the wires 626 and 628 to the controller system. In some embodiments, the wires 626 and 628 are bundled into an electrical wire to produce the sheath 655. The sheath 655 may allow for reversible attachment to the controller system to allow for separation of the device from the controller (e.g., via an electrical plug-in).

The wire post 665 functions to immovably attach the wires 626 and 628 from the sheath 655 to insertion through the housing 607.

Figure 6B:
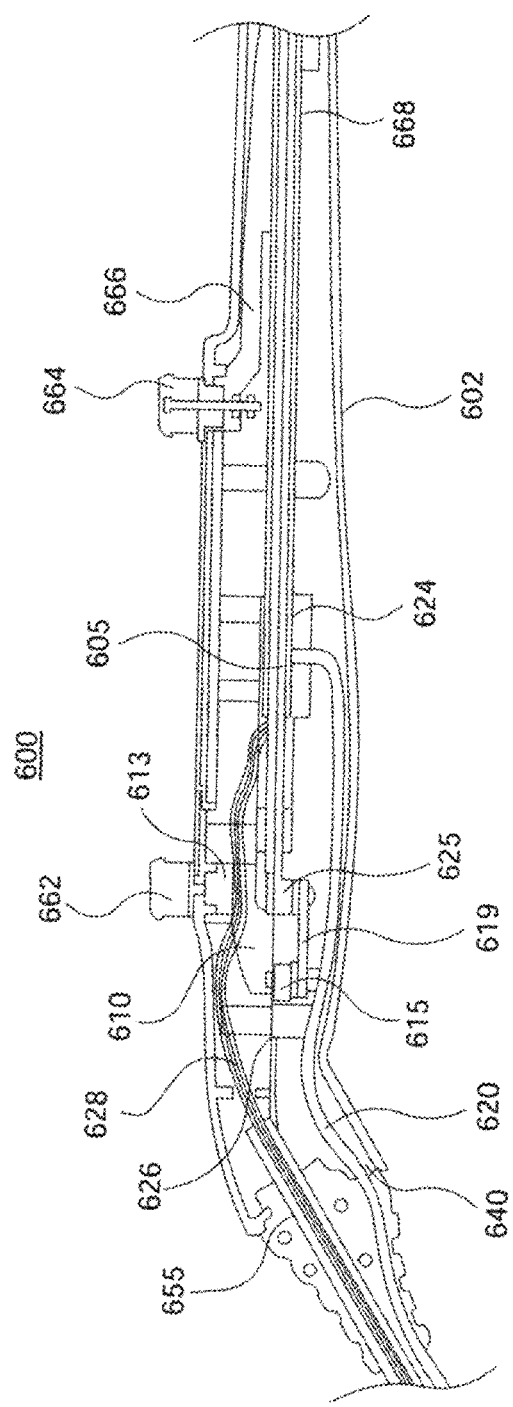
FIG. 6B shows a cross sectional view of an embodiment of the inside of handpiece FIG. 6A.

FIG. 6B shows a cross sectional view of an embodiment of the inside of handpiece 600. The handpiece 600 includes a shell 602, a central tube 605, levers 610, 615, and 619, sliding member 613, an aspirator tube 620, chamber 624, sliding piece 625, wires 626, wires 628, a vacuum port 640, and a sheath 655, and lead-wire post 665, which were discussed above in conjunction of FIG. 6A. Handpiece 600 may also include width knob 662, length knob 664, rigid coupling 666, and sheath 668. In other embodiments the handpiece 600 may not have all of the elements or features listed and/or may have other elements or features instead of or in addition to those listed.

Width knob 662 is rigidly fixed to sliding member 613. Thus when the user slides width knob 662, sliding member 613 slides in the same direction, and levers 610, 615, and 619, sliding member 613 translate the sliding motion of width knob 662 into the sliding motion of central tube 605. Length knob 664 is used for sheathing and unsheathing head 110. Rigid coupling 666 is rigidly attached to length knob 664 and to the sheath so that moving length knob 664 moves rigid coupling 666, which in turn moves the sheath. Sheath 668 is rigidly attached to rigid coupling 666 so that when length knob 662 moves, sheath 668 moves in the same direction sheathing or unsheathing head 110.

Figure 6C:
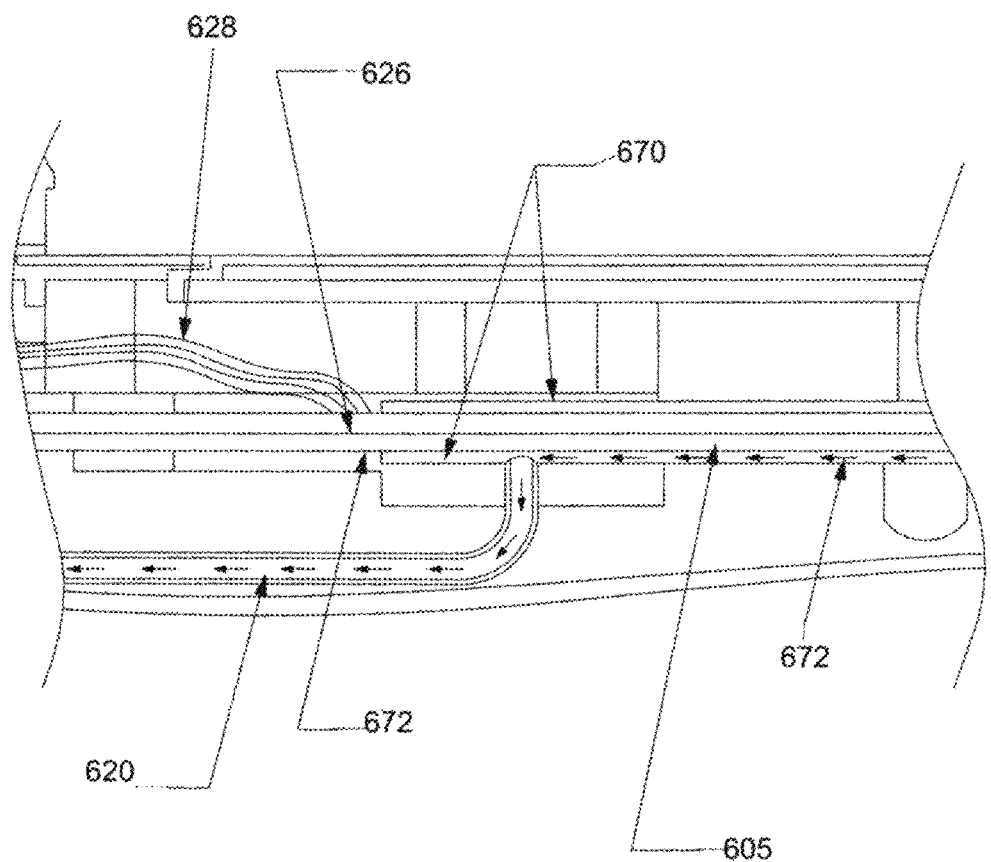
FIG. 6C shows a blowup of a portion of FIG. 6B.

FIG. 6C shows a blowup of a portion of FIG. 6B. FIG. 6C shows central tube 605, aspirator tube 620, wires 626, wires 628, epoxy 670 and close fitting tubing for sealing 672.

FIG. 7 shows an overhead view of an embodiment of the outside of a handpiece 700 used in an embodiment of a hollow body ablation apparatus for methods of ablation of hollow body organs. The handpiece 700 includes an aspirator tube 733, a fluid removal connector 735, an electrical cord 755, an electrical plug in 760, a length adjustment knob 782, a length adjustment groove 783, a width adjustment knob 784, a width adjustment groove 785, width icon 786, length icon 788, width scale 790, and length scale 792. In other embodiments the handpiece 700 may not have all of the elements or features listed and/or may have other elements or features instead of or in addition to those listed.

Handpiece 700 may include a shell constructed of a material that allows for sterilization. The shell functions to enclose the various parts of the hollow body ablation device, including but not limited to, the levers and central push/pull wire necessary to allow change in shape of the device, an aspirator tube, wires for attachment to the electrodes to allow RF energy, and a sheath to allow for covering the head of the ablation device during insertion into the hollow body organ. Shell 602 (FIG. 6A) may be sued as the shell of handpiece 700.

Handpiece 700 may be connected to a controller system (similar to controller system 104), which may include an algorithm that allows for the control of the alternating current (AC) and can be capable of applying different patterns of alternating the polarities of the different electrodes of an ablation apparatus. The frequency, voltage, and/or current may be adjusted to fit the cavity dimensions, and can be used to determine overall therapeutic energy doses, and/or determine other settings such as power, duration (the amount of time) of application of the electric field, etc. The controller is discussed in more detail in conjunction with reference to FIG. 2.

The aspirator tube 733 functions to remove fluid and/or gases from the hollow body organ before, during and after the ablation procedures. The aspirator tube 733 can be inserted through the shell 702 of the handpiece 700 and can be snaked up through an attachment tube 710.

The fluid removal connector 735, functions to attach the aspirator tube 733 to the reservoir and/or pump.

The electrical cord 755, allows for attachment to the controller system 704. The electrical cord 755 and is attached via wires to each electrode on the head of the hollow body ablation device. The wires can be inserted through the connector tube 710 to the electrodes. The wires can be connected via the electrical cord to the controller 704.

The electrical plug in 760, allows attachment of the wires within the electrical cord 755 to the controller system 704. The wires can each be separately controlled by allowing for separate pins within the plug. Thus, in some embodiments there are the same number of pins in the plug as there are electrodes.

The length adjustment knob 782 may be an embodiment of length knob 664, is attached to the sheath and functions to move the sheath up and over the head and/or to pull the two sides of the head together to form a tube for insertion through an opening into a hollow body organ. The length adjustment knob 782 can be rotated to lock the knob in place.

The length adjustment groove 783, allows slideable movement of the knob 782 to choose the amount of lengthening or shortening. When the length adjustment is at the proximal end, the head is completely collapsed and the sheath partially or completely covers the head of the device.

The width adjustment knob 784 may be an embodiment of width knob 662, and is attached to levers within the handpiece that effect movement of central push/pull wire attached to the head to pull each side of the head into or out of the sheath. Alternatively, the width adjustment knob 748 can move the distal electrodes into or out of an insulated tube next to the electrodes on the side of the head. The width adjustment knob 784 can be rotated to lock the knob in place.

The width adjustment groove 785 may be an embodiment of slot 612 and may allow slideable movement of the adjustment knob right and left to increase or decrease the width, particularly the width of the distal end of the head.

As shown in FIG. 7, information can be provided on the outside of the handpiece to help the user use the device. The user can be provided with values to show the amount of widening or lengthening of the head. Other information can include symbols (e.g., + or −) indicating widening or shortening. Further symbols such as carrots can be used to indicate widening and/or shortening. Arrows can be included to indicate the direction of movement of knobs and/or sliding.

Specifically, in an embodiment, width icon 786 indicates to the user that width knob 784 adjusts the width of the head. In an embodiment length icon includes an image of the head with arrows indicating the direction of expansion and contraction, which is along the width of the head at the top of the head. In other embodiments, another icon may be used. Length icon 788 indicates to the user that length knob 782 adjusts the length of the head. In an embodiment the length icon includes an image of the head with arrows indicating the direction of expansion and contraction, which is along the length of the head at the side of the head. In other embodiments, another icon may be used. Width scale 790 indicates the width of the head. Once the user places the head into the cavity and adjusts the head an appropriate amount by sliding width knob 784 the position of the knob on width scale 790 indicates how wide the head has been opened. The reading on width scale 790 of where width knob 786 is located may be entered into the controller, for determining the voltage setting for the ablation. Length scale 792 indicates the length of the head. Once the user places the head into the cavity and adjusts the head an appropriate amount by sliding length knob 782, the position of the length knob 782 on length scale 792 indicates how long the head has been opened. The reading on length scale 792 of where length knob 784 is located may be entered into the controller, for determining the voltage setting for the ablation. Once the width and length settings are entered based on the locations of length knob 782 and width knob 784, the controller automatically determines an appropriate power output for modes 1 and 2 at with to ablate the cavity of interest.

Figure 8A:
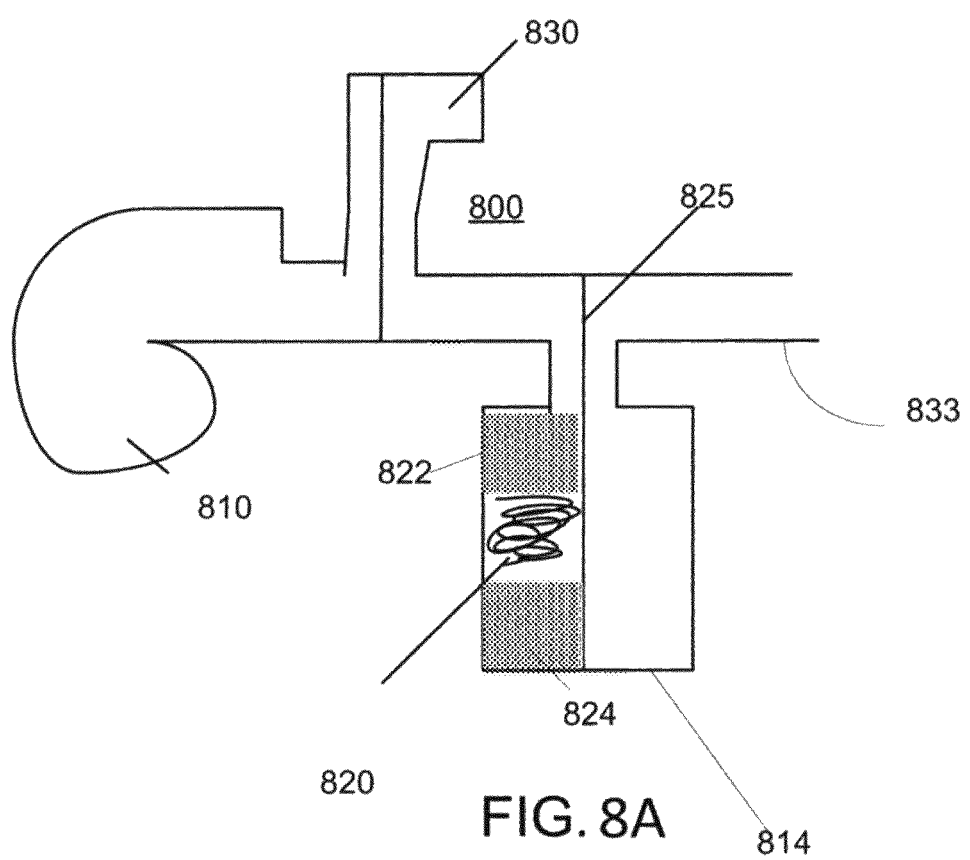
FIG. 8A shows an embodiment of a fluid removal device.

FIG. 8A shows a drawing of an embodiment of the fluid removal system 800 used in an embodiment of a hollow body ablation apparatus for methods of ablation of hollow body organs. The fluid removal system 800 includes a pump 810, a reservoir 814, an activated carbon filter 820, filter media 822, filter media 824, a secondary filter 830, and aspirator tube 833. In other embodiments the fluid removal apparatus 800 may not have all of the elements or features listed and/or may have other elements or features instead of or in addition to those listed.

The pump 810 can be any appropriate pump known in the art that is capable of pulling fluid and/or gases from the hollow body organ and into a reservoir during a procedure. The pump 810 can be attached to a reservoir and separated from the reservoir by filters to ensure that none of the fluid and/or gases end up in the pump and/or that non-sterile air does not come in contact with the hollow body organ. In some embodiments the pump and/or reservoir includes a sterile seal.

The reservoir 814 can be any type of reservoir 814 that can be attached to a pump 810 to allow removal of fluids and/or gases from a hollow body organ into a holding area. In some embodiments, the reservoir is composed of a material that allows for sterilization. In some embodiments, the reservoir includes an activated carbon filter 820 and/or fluid separator 823. In an embodiment, a first layer of filter media 822 is followed by the layer of activated carbon 820, followed by a second layer of filter media 824.

The reservoir 814 can include an activated carbon filter 820 that functions to remove particulates before they come in contact with the pump. "Activated Carbon," also called activated charcoal or activated coal is a form of carbon that has been processed to make it extremely porous and thus to have a very large surface area available for adsorption. The activated carbon filter can be separated from the reservoir by a fluid separator. The reservoir 814 can also include one or more layers of filter media meant to trap large molecules of fluid or vapor, prior to adsorption by the activated carbon material.

The fluid separator 823 can be any type of porous membrane, sieve or screen that allows for the passage of air or gases but does not allow for the passage of fluid or vapor.

The secondary filter 830 can be any type of filter that allows for the passage of air or gases but does not allow for the passage of fluid, vapor or small particles into the pump. The aspirator tube 833 can allow for the passage of fluids and/or gases through a tube to a reservoir. The aspirator tube 833 can be attached to a hollow body ablation device and can be inserted into a hollow body organ during an ablation procedure. The aspirator tube 833 can act to remove fluid and/or gases from the organ during the procedure.

Figure 8B:
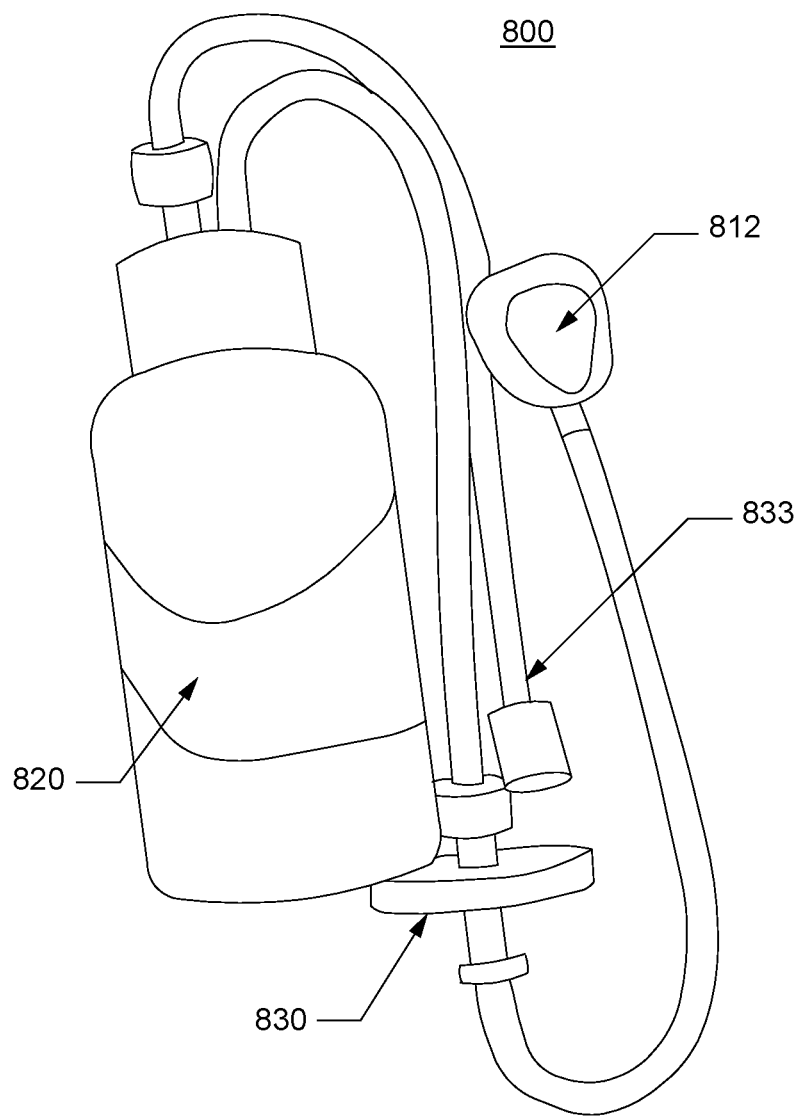
FIG. 8B shows another view of the fluid removal device.

FIG. 8B shows another view of the fluid removal device. FIG. 8B shows the activated carbon filter 820, the secondary filter 830, aspirator tube 833, (a patient contact device is located at the end of aspirator tube 833), and a connector 812. The connector 812 connects to pump 810.

Methods of Hollow Body Organ Ablation

Figure 9:
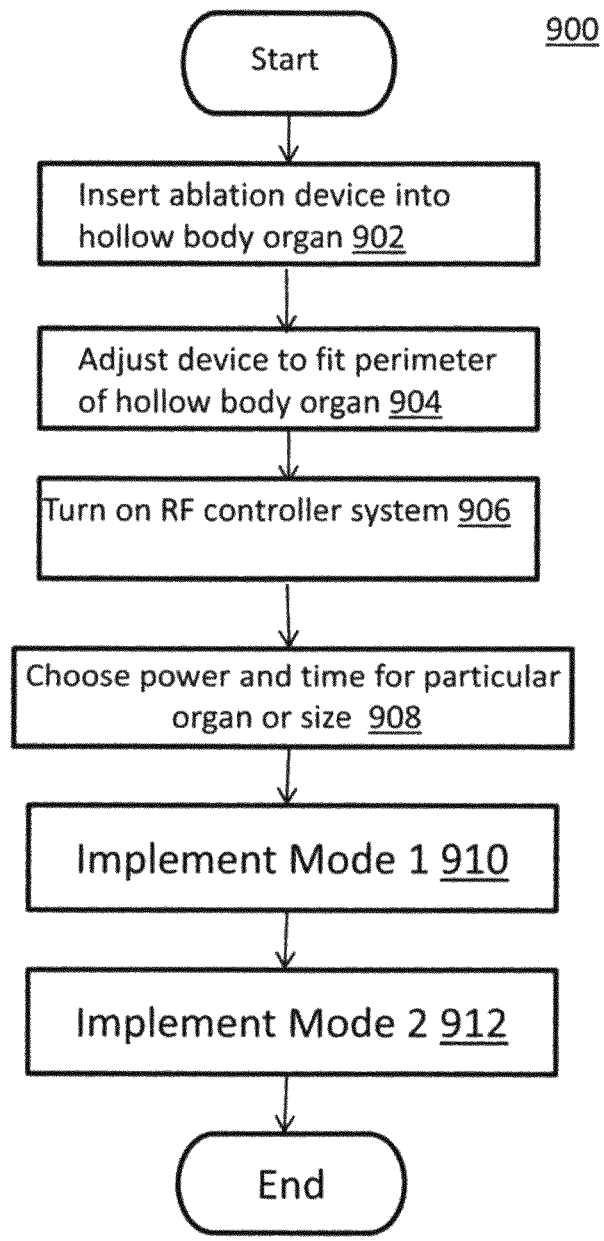
FIG. 9 shows a flowchart of a method of using an embodiment of a hollow body ablation device.

FIG. 9 shows a flow chart of an embodiment of method 900 in which a hollow body ablation apparatus (see 100 in FIG. 1A, for example) is used in a method of hollow body organ ablation.

Advantages of methods of using embodiments of the ablation devices include the ability to reduce the overall profile and size of the device to allow for minimally invasive access, to be able to better conform to organs with distorted cavity shapes, and to reduce the overall cost of manufacturing such devices. Ablation is defined as removal or excision. Ablation of the interior lining of a body organ is a procedure which involves heating the organ lining to temperatures which destroy the cells of the lining or coagulate tissue proteins for hemostasis.

Embodiments of ablation apparatus 100 may be used in cases where the hollow body cavity is more of a potential space (e.g., it is a hollow body cavity that might normally collapse down upon itself unless held open by some means). A good example of such a hollow body cavity would be the female human uterus. The uterine cavity is normally a small triangular shaped cavity with an entrance at the cervix. The cavity is basically flat, like an envelope, and is open only when filled with some material or possibly pressurized. Since the cavity is essentially flat, the anterior and posterior inner surfaces may or may not be in either partial or direct contact with each other, and a well defined perimeter exists. Whether the anterior and posterior surfaces are in contact with each other or not, the ablation is still effective and complete.

The methods involve inserting an ablation apparatus into a hollow body organ thru an aperture and ablating the interior lining of the organ.

In step 902 an ablation device such as those described in FIGS. 1-6 is inserted into a hollow body organ. The methods can be used for any hollow body organ, including but not limited to, a uterus, and a gall bladder. The device is inserted in the collapsed position to allow insertion through a small aperture into the organ. The efficient packing of right and left halves of the head of the hollow body ablation device when collapsed (folded up) prior to deployment, reduces the overall dimensions of the device for either insertion through a natural orifice, or through an incision. Reducing the size during deployment can be important for minimizing trauma to the patient or to reduce anesthesia requirements to control pain during insertion.

In step 904, the device is adjusted to fit the perimeter of the organ. A perimeter can be thought of as the length of the outline of a shape. For example, the size of a uterus can vary from patient to patient, but has an approximately triangular shape. Thus, the device can be adjusted to change the size of the triangular area to fit the shape and/or size of a particular uterus.

In step 906 the power controller is turned on, and the dimension of the region being ablated is input into the controller (the controller may be turned on earlier, but the power applied, algorithm chosen is based on the dimensions and/or characteristics of the cavity). In step 908 an algorithm, the amount of power, and duration of time that is power is applied, is automatically chosen for a particular organ, based on the organ, size, for example, based on a lookup table (e.g., according to lookup table 216). In some embodiments, the algorithm decides the type and amount of alternating current (AC) applied to the electrodes. The algorithm may include a determination of the frequency. In some embodiments, the amount and power are applied differently to different pairs of electrodes. Examples of some algorithms that can be used can be found in the description of FIG. 1D. In some embodiments steps 906 and 908 occur simultaneously. In some embodiments, the treatment algorithm may be read from a lookup table stored in a storage means within the ablation device, for example within an EEPROM, compact disk, microprocessor ROM, flash disk or other type of storage media or medium.

In some embodiments, in step 910, mode 1 is implemented (see FIG. 1D for a description of mode 1). A first amount of power is applied for a given period of time to a first region of the organ. The power may be applied by automatically applying a voltage, automatically measuring the current, and then automatically adjusting the voltage until the power output is at the desired level. In an embodiment, the process of finding the power level may be iterative.

In step 912, mode 2 is implemented (see FIG. 1D for a description of mode 2). A second amount of power that is different (e.g. lower) than the amount of power applied in step 910 is applied for a second period of time (e.g., a shorter period of time) to a second region of the organ (e.g., a region having a smaller distance between the walls at the perimeter of the organ. As in step 912, the power may be applied by automatically applying a voltage, automatically measuring the current, and then automatically adjusting the voltage until the power output is at the desired level. During steps 910 and 912, the amount of power used for the method can be from about 20 to about 100 W, including about 30, 40, 50, 60, 70, 80, and 90 watts. In some embodiments, the amount of power is between about 40 and about 50 W. The power can be left on for a time of between about 50 and about 300 seconds, including but not limited to, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 and all integers in between, depending on the organ an the dimensions of the organ. In some embodiments the power is left on for a time of between about 100 and about 150 seconds, depending on the organ the dimensions of the organ.

In an embodiment, each of the steps of method 900 is a distinct step. In another embodiment, although depicted as distinct steps in FIG. 9, step 902-912 may not be distinct steps. In other embodiments, method 900 may not have all of the above steps and/or may have other steps in addition to or instead of those listed above. The steps of method 900 may be performed in another order. Subsets of the steps listed above as part of method 900 may be used to form their own method.

Methods of Making Hollow Body Organ Ablation Devices

Figure 10:
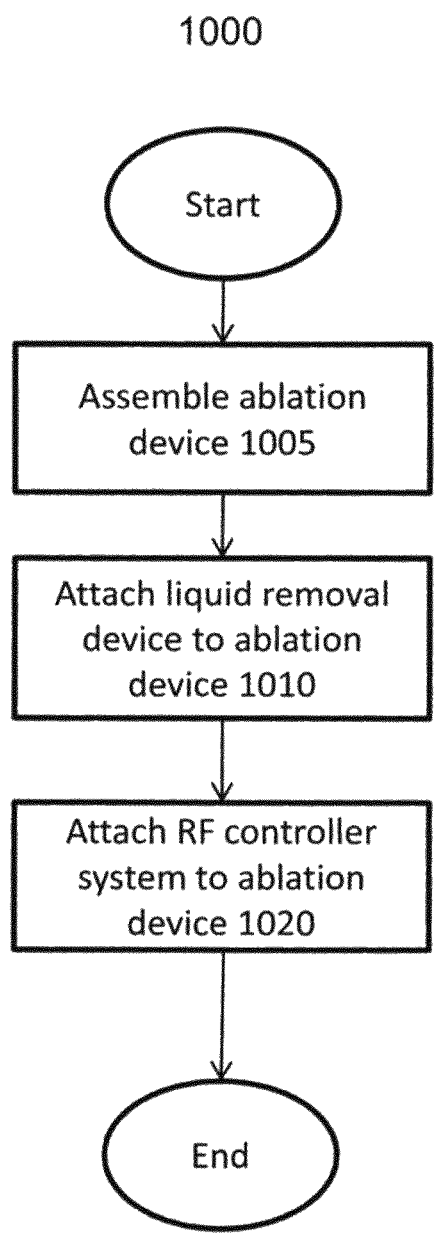
FIG. 10 shows a flowchart of a method of assembling the system components of an embodiment of a hollow body ablation apparatus.

FIG. 10 shows a flow chart of an embodiment of method 1000 in which a hollow body ablation apparatus (see 100 in FIG. 1A, for example) is configured.

In step 1005 the ablation device (see 101 in FIG. 1) is assembled. An embodiment of step 1005 is discussed in conjunction with FIG. 11.

In step 1010, a fluid removal device is attached to the ablation device (see 101 in FIG. 1). The fluid removal device can include a tube that can be snaked up through the handle and/or through the device to leave an opening within or next to the device. The tube can be attached to a reservoir and/or pump.

In step 1020 a controller is attached to the ablation device. The controller can also be attached to an electrical outlet and can control the amount of power the electrodes deliver to the tissue (by controlling the voltage applied to the electrodes) and/or the algorithm to be used. Thus, attaching the controller may include attaching the controller to the wires that are attached to the electrodes through a connector. The connector can be a wire with a plug having at least 6 pins, one pin for each electrode on head 110. Optionally, there may be an additional two or more pins, and a controller may be attached to the additional pins. Using the additional pins, the controller may also be used for recording information about the ablation, such as the power, and duration of time of each mode applied.

In an embodiment, each of the steps of method 1000 is a distinct step. In another embodiment, although depicted as distinct steps in FIG. 10, step 1002-1020 may not be distinct steps. In other embodiments, method 1000 may not have all of the above steps and/or may have other steps in addition to or instead of those listed above. The steps of method 1000 may be performed in another order. Subsets of the steps listed above as part of method 1000 may be used to form their own method.

Figure 11:
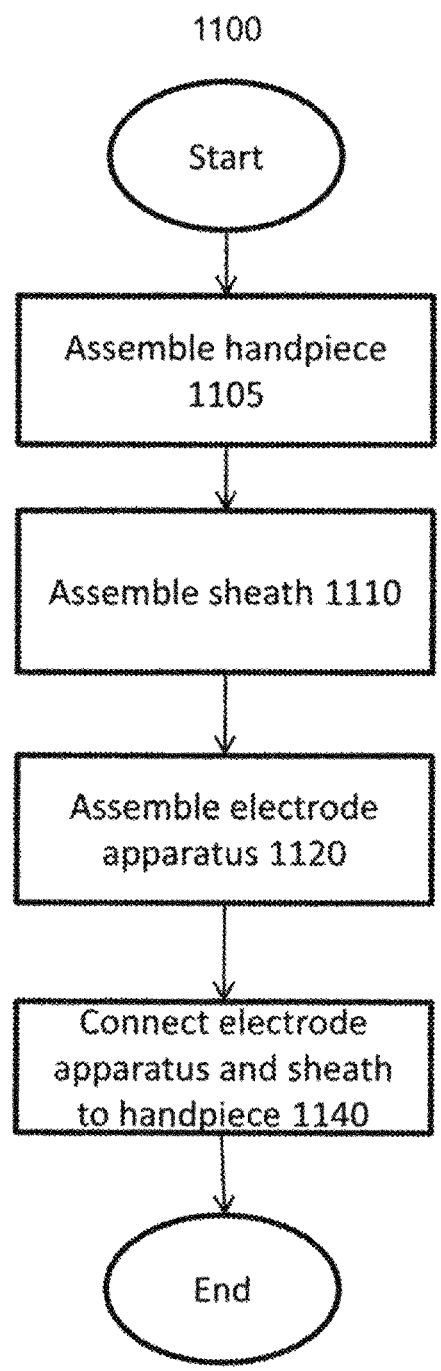
FIG. 11 shows a flowchart of a method of assembling the system components of the hollow body ablation device.

FIG. 11 shows a flow chart of an embodiment of method 1100 in which an ablation device (see 101 in FIG. 1A, for example) is configured. Method 1100 is an embodiment of step 1005 in FIG. 10.

In step 1105 a handpiece is assembled to include knobs for adjustment of the length and width of the device. The knobs can be attached to the central push/pull wire 438 to control the collapsing of the electrode apparatus into the sheath. In some embodiments, within the handpiece the knobs are attached to levers which are attached to push and pull wires and moving the knobs moves the push and pull wires as needed to change the width and length of the device. The knobs can move the levers by sliding the levers along a groove (e.g., in a side to side direction to change the width and/or in a back to front direction to change the length). In some embodiment, the knobs can be attached to a lever that is attached to a push or pull wire that moves the sheath up or down as desired for insertion of the device.

Within the handpiece are wires connecting electrodes to the power source and/or controller. In some embodiments, there are the same number of wires as electrodes. The wires can be connected to the controller via a power cord and plug. Also included within the handpiece is an aspirator tube to allow removal of fluid during the procedure.

In step 1110 a sheath is assembled by attaching the sheath to the handpiece and to a width and/or length adjustment knob on the handpiece. The adjustment knob can be attached to a push or pull wire that pushes or pulls the sheath over the device or back from the device depending on the way the knob is turned or moved.

In step 1120 the head (e.g., the electrode apparatus) is assembled to be the approximate shape of the hollow body organ (e.g., triangularly shaped, a parallelogram or oval). The head has electrodes on the base and the sides of the device. Each side of the device is attached so that the sheath can be moved to cover the electrodes. The electrodes are chosen to allow movement into and out of the sheath. The electrodes are chosen to allow movement of the device from a triangular shape (or parallelogram) to two parallel sides covered by the sheath when collapsed. The electrodes can include moveable electrodes and rigid electrodes. The electrodes can include D-shaped electrodes to allow the device to be collapsible. The electrodes can be separated by insulators to keep the electrodes from touching.

In step 1140 the electrode apparatus, sheath and handpiece are attached so that a user can manipulate the device to collapse and cover the electrode apparatus (e.g., with the sheath) so that when inserted the device can fit through a small aperture. This step also allows the user to manipulate the length and width of the device to fit the size of the hollow body organ.

In an embodiment, each of the steps of method 1100 is a distinct step. In another embodiment, although depicted as distinct steps in FIG. 11, step 1105-1140 may not be distinct steps. In other embodiments, method 1100 may not have all of the above steps and/or may have other steps in addition to or instead of those listed above. The steps of method 1100 may be performed in another order. Subsets of the steps listed above as part of method 1100 may be used to form their own method.

EXAMPLES

In the following examples, embodiments of the ablation devices were used to treat a test specimen (a beef steak) and the width, length and depth of treating was measured. Beef steak was used to approximate the hollow body organ—"a meat cavity." Using the methods and devices herein in which radio frequency electrodes were arranged in a pattern that made contact with the surface area of the beef steak, energizing the electrodes resulted in treatment of a much larger area than was specifically contacted by the electrodes. When used in a hollow body organ, this would result in a complete ablation of the lining of the body cavity, even though the electrodes only make contact with the surface area of the organ in proximity to the perimeter. This has numerous advantages over the prior art in which devices to perform complete ablation of a hollow body cavity required that radio frequency electrodes cover all or substantially all of the surface area to be ablated, rather than just a portion of the surface area in close proximity to the perimeter of the organ.

Example 1

Test Treatment of a Beef Steak with the Ablation Device Shown in FIG. 1

Example 1 describes the results from a test for the endometrial ablation device shown in FIG. 1A. The tests assumed a uterus size of 4.5 cm wide by 6.5 cm long. Thus, the device was configured to have a 4.5 cm long base and 6.5 cm long sides. All tests were performed using two slices of beef in a "meat cavity".

Figure 12:
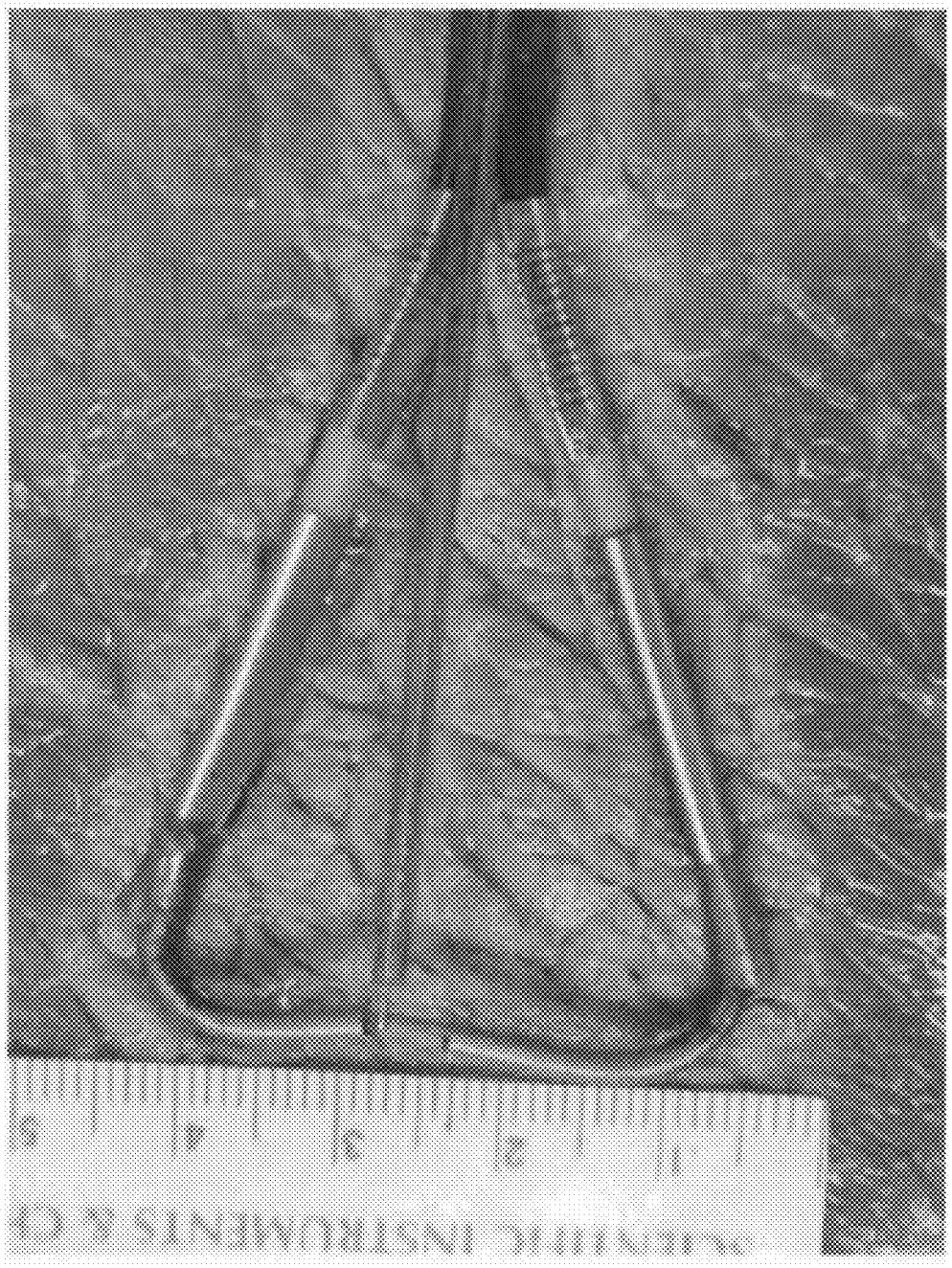
FIG. 12 shows a front elevation view of a method of testing a hollow body ablation apparatus—post-treatment.
Figure 13:
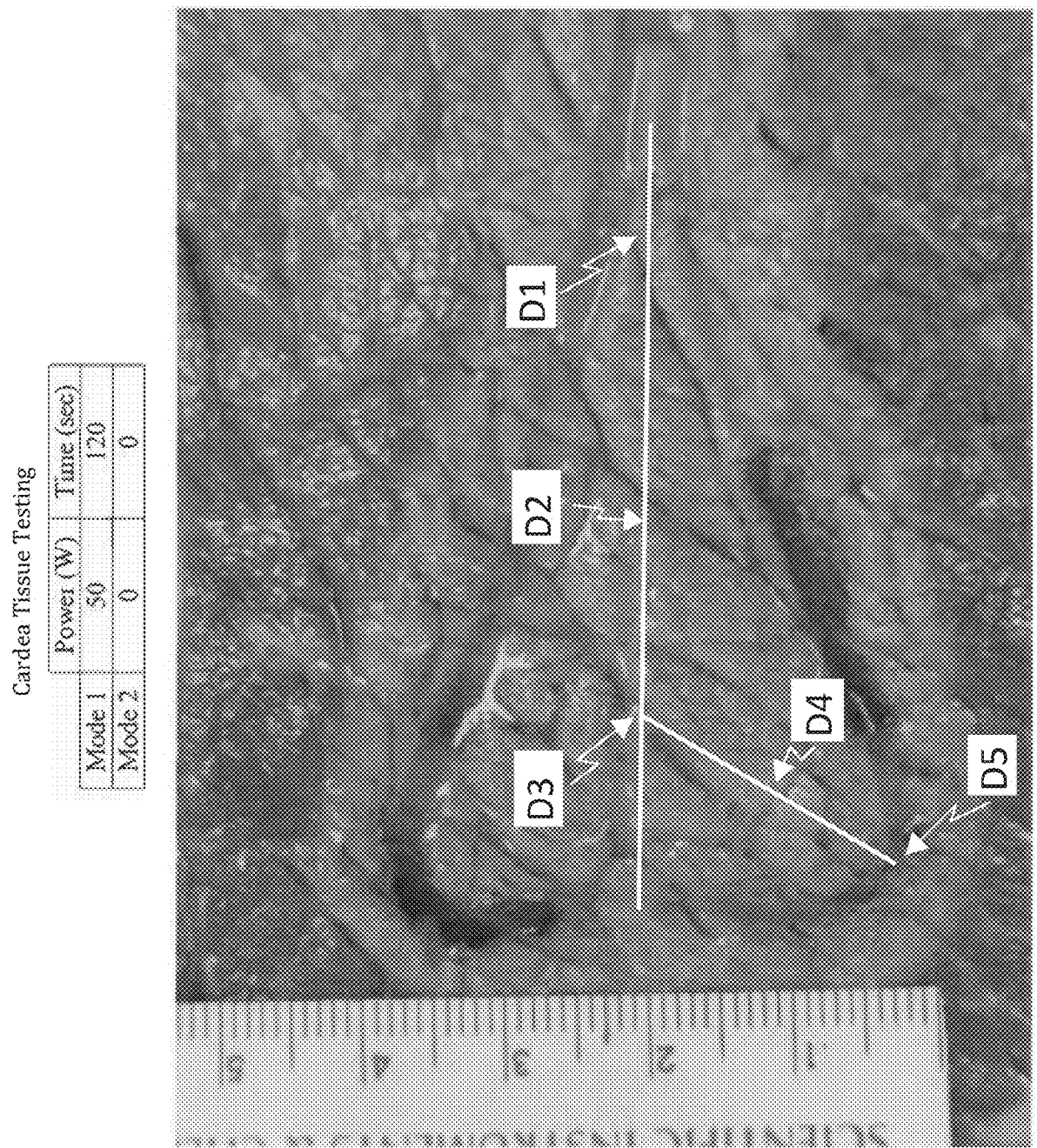
FIG. 13 shows a front elevation view of a method of testing a hollow body ablation apparatus—post-treatment.
Figure 14:
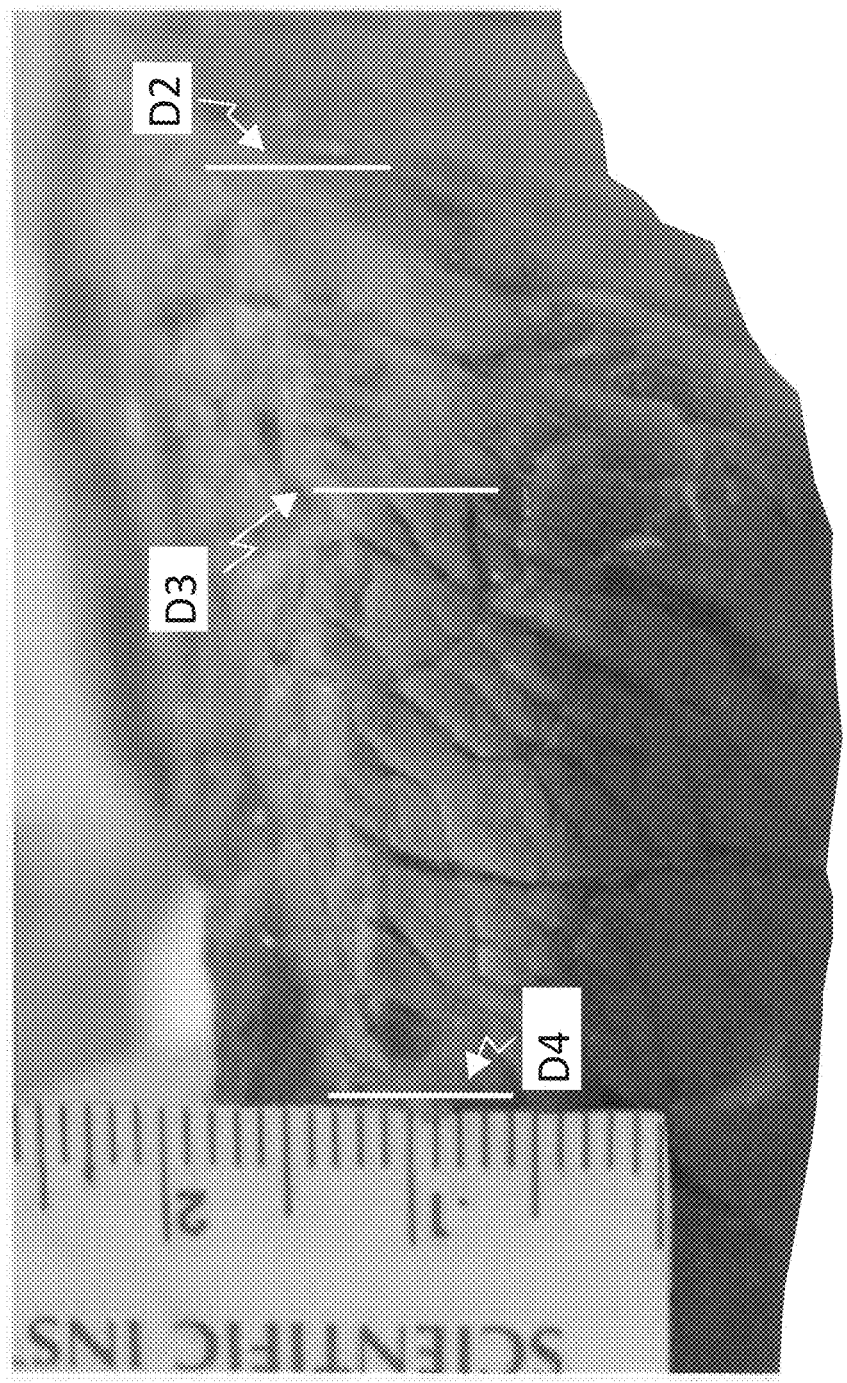
FIGS. 14 and 15 show side elevations of the ablated test material.
Figure 15:
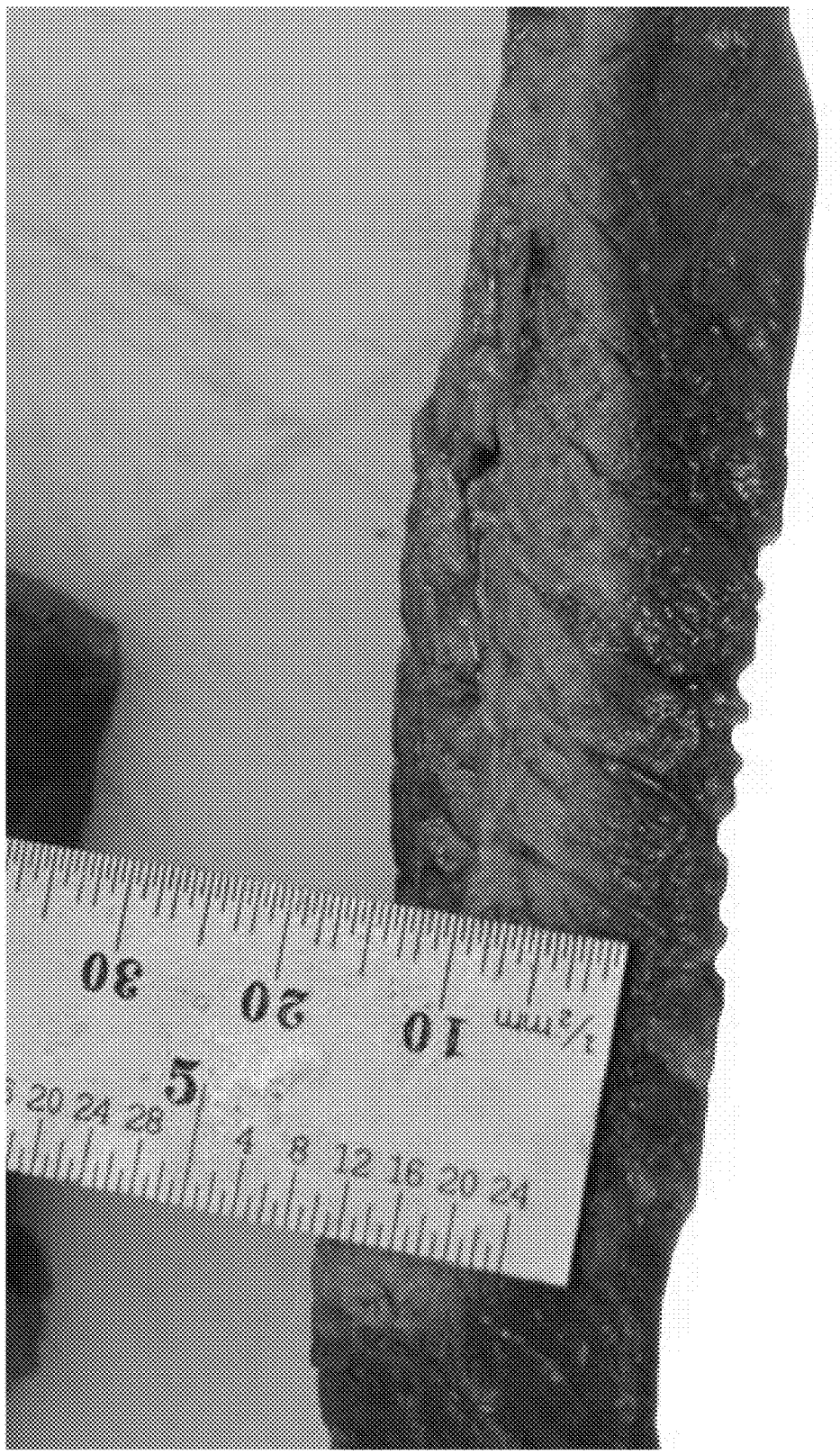

As shown in FIGS. 12 and 13, the device was configured with six electrode segments as follows: The distal electrodes (on the base) were 0.077" diameter, stainless steel extension springs. The middle electrodes were stainless steel D-tubing created from 3.75 mm OD tubing (9 GA). The D-length was 2.60 mm and the D-width was 4.55 mm. The proximal electrodes were stainless steel D-tubing (as above) with slots cut in the round portion of the D to allow for flexibility in only one plane. The goal of the test was to find the optimum power and time settings to effectively treat the tissue. So, a number of tests were performed varying the amount of power (watts), the amount of time (seconds) and using more than one mode as follows:

Test 1. FIG. 12 shows a front elevation view of the method of testing a hollow body ablation apparatus in which RF energy was applied at 50 W for 120 seconds for mode 1. In FIG. 13 the RF had not yet been applied to the electrodes, but the head of the device was fully opened. FIG. 12 shows a front elevation view of the method of testing a hollow body ablation apparatus—after applying mode 1 at 50 Watts for 120 seconds. FIG. 12 shows that the electrodes affected an area wider than the width of the electrodes. In fact, the whole area defined by the head of the device was affected including up to 10 mm outside of the electrodes. Thus, as judged by the widely affected area, the algorithm does more than just apply current.

FIG. 13 shows a front elevation view of a method of testing a hollow body ablation apparatus—post-treatment without the device. FIG. 13 shows that the treatment affected the area within the devices electrodes and also an area of between 3 and 10 mm outside of the area that the electrodes touched. The amount of heating was surprisingly even, although there was more heating directly under the electrodes.

The depth of the treatment was analyzed by cutting the steak through the centerline and sides of the affected area and measuring the depth. The steak was affected at a depth of about 4 to 10 mm at the centerline of the treatment as well as directly under the electrodes. FIG. 13 also shows test points D1-D5 at which the depth of ablation is measured. The test area is cut along the lines connecting points D1-D5 so that the depth of heating can be measured.

Other tests were as follows:

Test 2: Mode 1 was 40 watts for 150 seconds; Mode 2 was 30 watts for 30 seconds. This method showed an equal effectiveness to the first test.

Test 3: Mode 1 was 50 watts for 113 seconds. This method showed an equal effectiveness to the first test.

Test 4: Mode 1 was 40 watts for 150 seconds; Mode 2 was 30 watts for 30 seconds. This method showed an equal effectiveness to the first test.

The smaller overall surface area of the smaller round springs resulted in a higher energy density at similar powers. To get the desired results, settings of 40 W for 150 seconds and 30 W for 30 seconds was required. However, higher powers resulted in charring and therefore less effective treatment time.

Table 2 provides the results for 20 different treatments using different widths and lengths, and a variety of modes. In Tables 2A and 2B, FIGS. 16 and 17, depth is provided for electrodes D1-D6. The numbering of the electrodes is as shown in FIG. 1A2. However, in all cases, the depth of treatment as shown resulted in a good result. The test results were unexpectedly good in that the periphery (which is close to or in contact with the electrodes) is not charred, the entire cavity is heated (including the central area in the center of the opening of the head 110), and the depth of heating is shallow enough so as not to heat the myometrium or serosal layer of the uterus.

An Embodiment of Modes of Operation

Figure 18A:
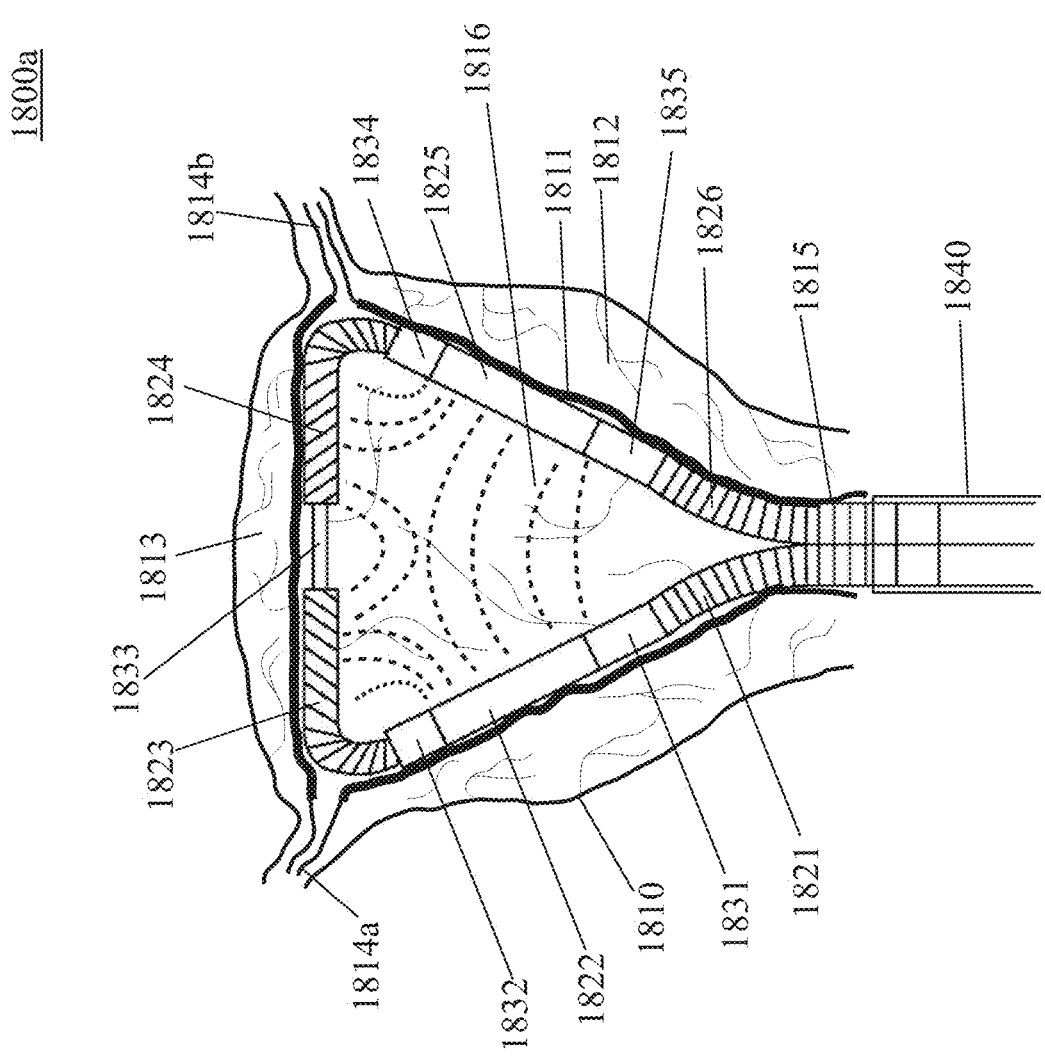
FIG. 18A shows a cross sectional anterior view of an embodiment of using a first mode of the hollow body ablation device for ablating uterine cavity of a patient.

FIG. 18A shows a cross sectional anterior view 1800*a* of an embodiment of using a first mode of the hollow body ablation device for ablating uterine cavity of a patient. FIG. 18A includes at least a uterus 1810, endometrium 1811, myometrium 1812, fundus 1813, fallopian tubes 1814*a-b*, cervical canal 1815, and posterior surface 1816. FIG. 18A also includes at least six electrodes 1821-1826, five insulators 1831-1835, and a sheath 1840. In other embodiments, FIG. 18A may not have all of the elements or features listed and/or may have other elements or features instead of or in addition to those listed.

FIG. 18A shows a cross sectional anterior view (when the patient is lying down) of uterus 1810 that includes a generally triangular cavity with a perimeter that may be outlined by a triangular head of the hollow body ablation apparatus. FIG. 18A is similar to FIG. 1D. However, although FIG. 1D shows the electric fields created by the hollow body ablation device, FIG. 1D does not expressly show how the hollow body ablation device fits into the uterus and application of the electric fields to the uterus, whereas FIG. 18A shows how the hollow body ablation device fits into the uterus and application of the electric fields of the first mode to the uterus. In at least one embodiment, the triangular head includes six electrodes, four on each side and two on the base of the head, which are in direct contact with the tissue in close proximity to the perimeter of the uterus 1810. The six electrodes are energized in different modes to form various combinations of pairs of electrodes having opposite charges, in which for each pair of electrodes, the electrodes are coupled to one another in that an electric field (e.g., an AC electric field) is established between the two electrodes of the pair. Adjacent electrodes are separated from one another by insulators for preventing shorting between the electrodes. In FIG. 18A, a first mode of operation energize four of the six electrodes to establish electric fields to cover the entire upper region of the tissue surface within the perimeter, so that the upper region of the tissue surface is ablated uniformly and entirely. The posterior view of the uterus of FIG. 18A is similar to the anterior view, and in at least one embodiment the tissue surface in the posterior view may be ablated in similar manner as in FIG. 18A.

Uterus 1810 is a major female reproductive sex organ that at one end opens through cervical canal 1815 into the vagina, and at the other end (close to fundus 1813) is connected to two fallopian tubes 1814*a-b* that further lead to ovaries. Endometrium 1811 is the innermost layer of the uterine cavity, which builds a lining that is periodically shed or reabsorbed if no pregnancy occurs. In at least one embodiment, shedding of the functional endometrial lining is responsible for menstrual bleeding, or sometimes heavy bleeding that may affect a woman's quality of life. One method to treat abnormal uterine bleeding or to reduce menstrual bleeding is to perform a surgical procedure to safely destruct (e.g., by burning away, freezing, etc) the lining of endometrium 1811 of the uterus 1810. In at least one embodiment, the hollow body ablation apparatus 100 may use a plurality of electrodes to perform the endometrial ablation. Myometrium 1812 is a layer beneath the endometrium 1811, including mostly smooth muscles. In at least one embodiment, endometrial ablation does not heat or destruct the myometrium 1812. Fundus 1813 is the top portion of the uterus 1810, opposite to the cervical canal 1815. FIG. 18A shows a posterior surface 1816 of the uterus 1810 within the perimeter outlined by the head of the ablation apparatus, while the uterus 1810 also includes an anterior surface (not shown in FIG. 18A) sharing the perimeter of the uterus 1810 and facing the posterior surface 1816. In at least one embodiment, the electrodes on the head ablates both the posterior surface 1816 and the anterior surface of the uterus 1810.

In at least one embodiment, six electrodes 1821-1826 are the same as the six electrodes numbered 1-6 as discussed in conjunction with FIG. 1D. Electrode 161 (FIG. 1A) may be an embodiment of one of the electrodes 1821 and 1826. Electrodes 162 (FIG. 1A) may be an embodiment of one of the electrodes 1822 and 1825. Electrodes 163 (FIG. 1A) may be an embodiment of one of the electrodes 1823 and 1824. In at least one embodiment, insulators 1831 and 1835 may be the same as insulator 120 (FIG. 1A), while insulators 1832 and 1834 may be the same as insulator 121 (FIG. 1A). Insulator 1833 may be an embodiment of the insulator 122. In at least one embodiment, sheath 1840 is an embodiment of the sheath 130.

In at least one embodiment, the first mode for energizing electrodes 1822-1825 for ablating the upper region of the tissue surface is an embodiment of mode 1 as discussed in conjunction with FIG. 1D. In the first mode, electrodes 1822-1825 are energized to form electrode bipolar coupling pairs in a bipolar mode for establishing electric fields to cover the entire upper region of the tissue within the perimeter. The first mode may activate electrodes 1822-1825 in a way that electrodes 1822 and 1824 have a first polarity of charge while electrodes 1823 and 1825 have a second polarity of charge, and electrodes 1823 and 1825 have a first polarity of charge while electrodes 1822 and 1824 have a second polarity of charge. As the AC current applied to electrodes 1822-1825, which electrodes (electrodes 1822 and 1824 or electrodes 1823 and 1825) is positive and which pair is negative alternates. As a result, electric fields may be established between the coupled pairs of electrodes 1822 and 1825, 1822 and 1823, 1823 and 1824, as well as 1824 and 1825, as shown in dashed lines in FIG. 18A. In at least one embodiment, the combinations of the coupled pairs of electrodes allow electric fields to cover the entire upper region of the tissue surface within the perimeter of the ablation device of FIG. 18A, having electrodes 1822-1825. In this embodiment, the upper region may be ablated uniformly even though the electrodes 1822-1825 only make contact with the perimeter of the tissue, without the necessity of moving electrodes or adding any electrode to be in contact with the tissue in the middle of the region. In at least one embodiment, the electric fields that cover the entire region of tissue within the perimeter cause the fluid within and/or on the surface of the tissue (e.g., endometrium of the uterus) to heat up, and the hot fluids, in-turn, heat the tissue that carries the fluids. The heating of the tissue by heating the fluids carries by the tissue results in a more uniform ablation of the entire region than were the tissue heated directly. The determination of the voltage and duration of time that the voltage is applied, for at least one embodiment, was discussed in conjunction with FIG. 1D.

In at least one embodiment, the electrodes 1821-1826 are configured to outline the perimeter of a region of tissue to be ablated, and the entirety of the region gets ablated uniformly even without any electrode in the middle or in contact with the region of tissue within the perimeter. In this embodiment, aligning electrodes 1821-1826 only on the perimeter of the head when deployed requires fewer electrodes than were there also electrodes in the interior area outlined by the perimeter. As a result of having fewer electrodes, the diameter of the collapsed head (which is the head while the head is in the sheath and before the width of the head is widened) can be smaller than were there also electrodes in the interior area outlined by the perimeter. Since the diameter of the collapsed head is smaller, inserting the collapsed head in the desired cavity is less invasive than were the collapsed head larger, the insertion of the collapsed head into an organ or cavity causes less discomfort to the patient than were the collapse head larger. In other embodiment, electrodes may be arranged throughout the middle of the head (e.g., on a line bisecting the triangular head).

In at least one embodiments, mechanical structures may be included for supporting the head and/or adjusting the shape and/or size for fitting different dimensions. For example, two side push/pull wires (or other mechanical structures) may be attached to electrodes 1822 and 1825 or two corners of the triangular shaped head for pushing the head open to fit the perimeter of the cavity (e.g., triangular cavity of the uterus).

Figure 18B:
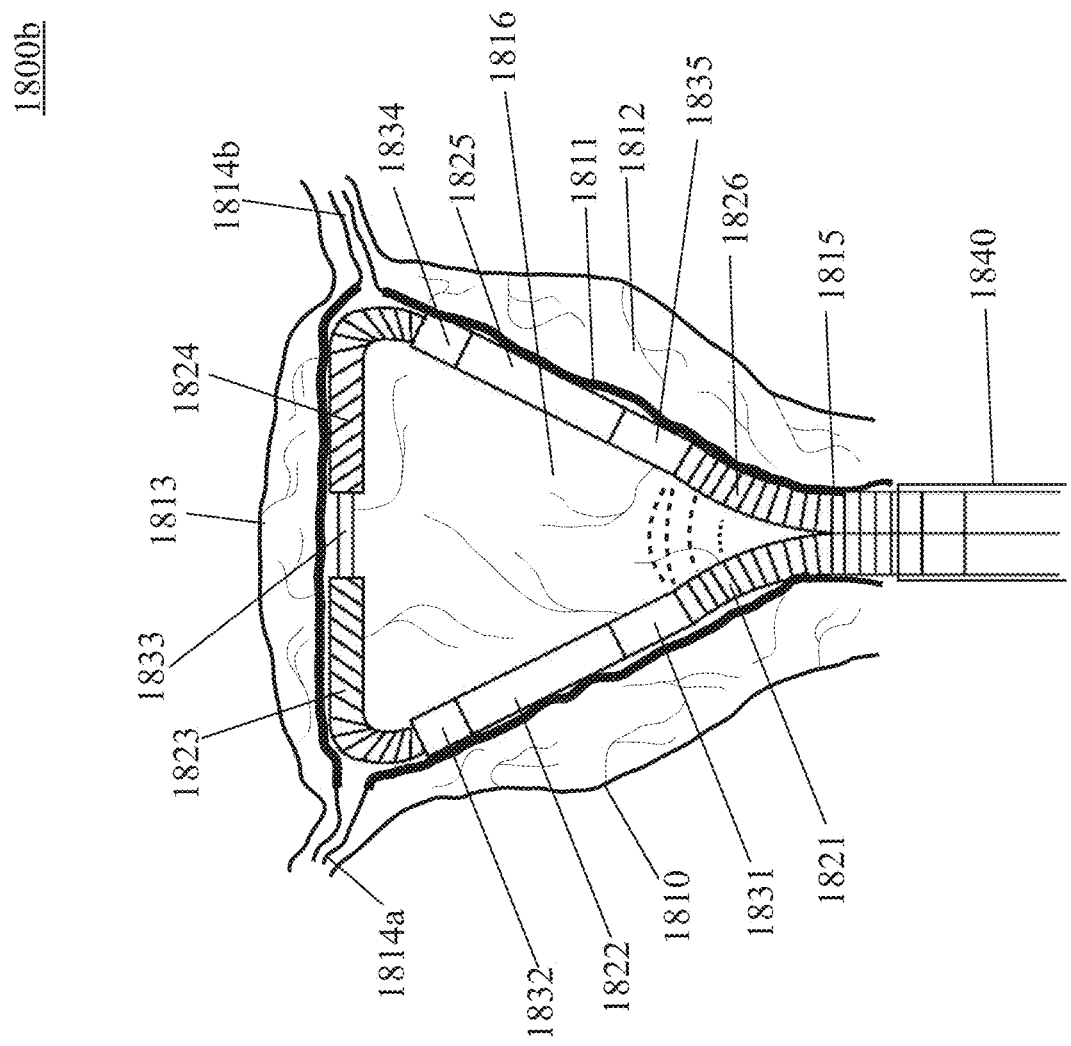
FIG. 18B shows a cross sectional anterior view of an embodiment of using a second mode of the hollow body ablation device for ablating the uterine cavity.

FIG. 18B shows a cross sectional anterior view 1800*b* of an embodiment of using a second mode of the hollow body ablation device for ablating the uterine cavity. FIG. 18B includes at least uterus 1810, endometrium 1811, myometrium 1812, fundus 1813, fallopian tubes 1814*a-b*, cervical canal 1815, posterior surface 1816, electrodes 1821-1826, insulators 1831-1835, and sheath 1840, which were discussed in conjunction with FIG. 18A. In other embodiments, the view of FIG. 18B may not have all of the elements or features listed and/or may have other elements or features instead of or in addition to those listed.

FIG. 18B shows a second mode for energizing electrodes 1821 and 1826 for ablating a lower region of the tissue surface. The second mode may be an embodiment of the mode 2, which was discussed in conjunction with FIG. 1D. FIG. 18B (like FIG. 18A) is also similar to FIG. 1D. However, FIG. 1B shows the application of the electric fields of the second mode to the uterus while the hollow body ablation device is in the uterus (whereas FIG. 1D does not show the uterus). In the second mode, electrodes 1821 and 1826 are energized to form an electrode bipolar coupling pair in a bipolar mode for establishing electric fields to cover the entire lower region of the tissue within the perimeter. In at least one embodiment, one of electrodes 1821 and 1826 is positively charged and the other is negatively charged. The second mode (similar to the first mode) applies an alternating voltage to electrodes 1821 and 1826, such that which of electrodes 1821 and 1826 is positively charged and which is negatively charged alternates.

In at least one embodiment, one of the first and second modes is terminated before the other is activated and vice versa, thereby reducing the likelihood of electric fields being established between the electrodes used in the first mode (electrodes 1822-1825) and the electrodes used in the second mode (electrodes 1821 and 1826). In at least one embodiment, the first mode and second mode include different voltages and durations of time of application for a uniform ablation of the entire area within the perimeter (e.g., both the upper region and lower region), which were discussed in conjunction with FIG. 1D. In one embodiment, mode 1 and mode 2 may start simultaneously.

In alternative embodiments, electrodes 1821 and 1826 may be replaced with multiple pairs of electrodes, and electrodes 1822-1825 may be replaced with another number of electrodes. In other embodiments, the uterine cavity may be divided into more than two regions, and more than two modes may be applied to ablate more than two regions, or some of the regions selectively.

Figure 19:
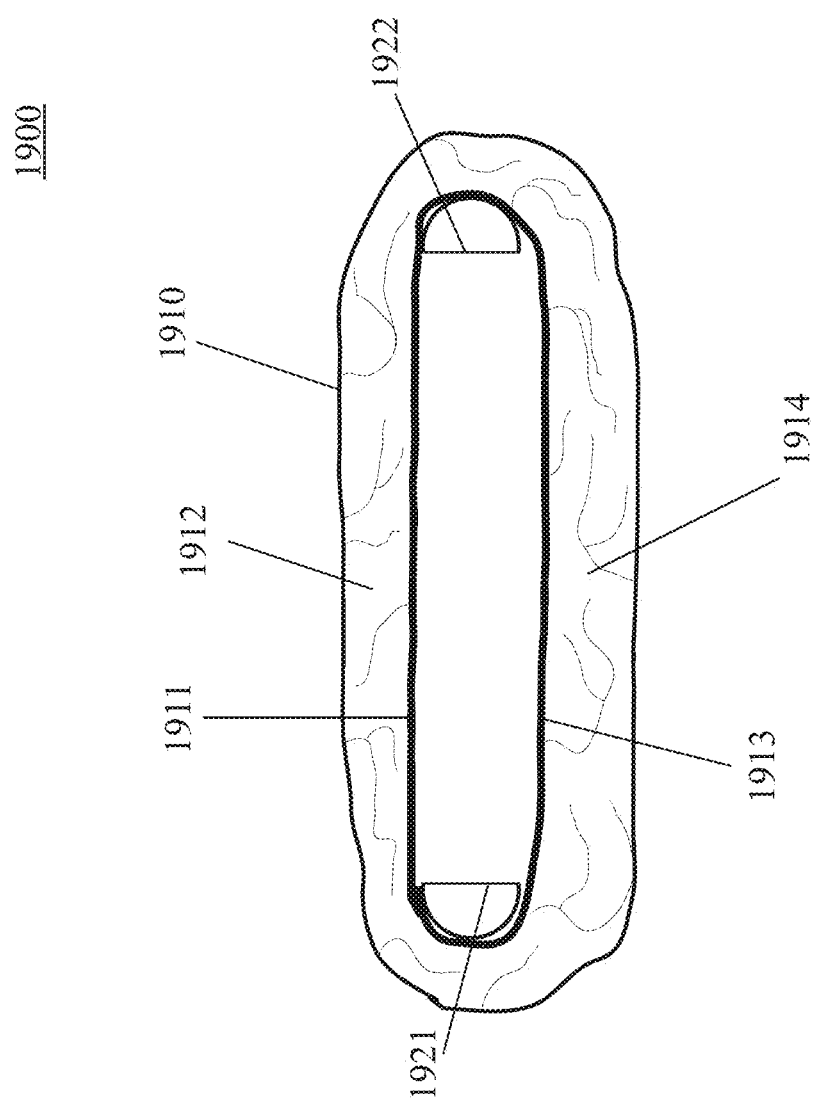
FIG. 19 shows a cross sectional view of the hollow body ablation device for ablating both anterior and posterior surfaces of the uterine cavity.

FIG. 19 shows a cross sectional view 1900 of the hollow body ablation device for ablating both anterior and posterior surfaces of the uterine cavity. FIG. 19 includes at least a uterus 1910, anterior endometrial surface 1911, anterior portion of myometrium 1912, posterior endometrial surface 1913, posterior portion of myometrium 1914, and electrodes 1921 and 1922. In other embodiments, FIG. 19 may not have all of the elements or features listed and/or may have other elements or features instead of or in addition to those listed.

FIG. 19 shows a cross sectional view looking into the cervical canal 1815 using the bipolar modes of the electrodes to ablate the uterine cavity as discussed in conjunction with FIGS. 18A and 18B. FIG. 19 shows that the uterus 1910 includes at least an anterior side with anterior endometrial surface 1911 and anterior portion of myometrium 1912, and a posterior side with posterior endometrial surface 1913 and posterior portion of myometrium 1914. The anterior endometrial surface 1911 and posterior endometrial surface 1913 have the same perimeter that is the perimeter of the uterus 1910. In at least one embodiment, the uterus in FIG. 19 is the uterus in FIGS. 18A and 18B. In at least one embodiment, the anterior endometrial surface and a posterior endometrial surface of FIG. 19 are part of the endometrium 1811 of FIGS. 18A and 18B, while the anterior portion of myometrium and a posterior portion of myometrium of FIG. 19 are the myometrium 1812 of FIGS. 18A and 18B. FIG. 19 shows an alternative view of at least one embodiment of FIGS. 18A and 18B, from the side of the cervical canal 1815 toward the fundus 1813. In at least one embodiment, electrodes 1921 and 1922 may be a cross section of an embodiment of the electrodes 1822 and 1825, respectively, which were discussed in conjunction with FIGS. 18A and 18B. Similarly, the cross sectional view of FIG. 19 may be an alternative view of FIGS. 18A and 18B in the area that is close to the cervical canal 1815, and electrodes 1921 and 1922 may be cross sections of embodiments of the electrodes 1821 and 1826. In at least one embodiment, the six electrodes of the head of FIG. 18, outline the perimeter of the uterus 1910 of FIG. 19. In an embodiment, the six electrodes of FIGS. 18A and 18B, include the electrodes 1921 and 1922 with "D" cross sections, one on each side of the head, with round sides of the "D" shaped electrodes 1921 and 1922 in contact with the perimeter of the uterus 1910 and the flat sides of the "D" shaped electrodes 1921 and 1922 facing each other. In at least one embodiment, the bipolar modes of operation (e.g., an alternation of mode 1 and mode 2 of FIG. 1D) cause electric fields to be established to cover both the anterior endometrial surface 1911 and posterior endometrial surface 1913, entirely and uniformly. In the embodiment of electrodes 1921 and 1922 in which electrodes 1921 and 1922 are cross sections of embodiments of the electrodes 1822 and 1825, the first mode (as discussed in FIG. 18A) energize the electrodes 1921 and 1922. In the embodiment of electrodes 1921 and 1922 in which electrodes 1921 and 1922 are cross sections of embodiments of the electrodes 1821 and 1826, the second mode (as discussed in FIG. 18B) energize the electrodes 1921 and 1922. As a result, both the anterior endometrial surface 1911 and posterior endometrial surface 1913 of the uterus 1910 are ablated, which share the perimeter of the uterus 1910 outlined by and in contact with the electrodes of the ablation apparatus.

In at least one embodiment, the electrodes of the ablation apparatus ablate endometrial surfaces (1911 and 1913) but not myometrial portions on both anterior and posterior sides (1912 and 1914) of the uterus 1910. In at least one embodiment, electric fields are capable of ablating the entire regions of the anterior and posterior surfaces (1911 and 1913) of the uterus even when no electrode is in direct contact with the middle areas of the anterior and posterior surfaces of the uterus. In at least one embodiment, the hollow body ablation apparatus may ablate two surfaces of a body cavity when the electrodes outline the perimeter of both two surfaces, which surfaces may be either separated or contacting one another.

In at least one embodiment, electrodes 1921 and 1922 include "D" shaped cross sections for maximizing the circumference and therefore the areas of the electrodes that are in contact with the tissue. The electric charges are spread out over a larger area on the rounded sides of the electrodes 1921 and 1922, and are therefore less concentrated and less likely to char the tissue (e.g., the perimeter of the uterus). When collapse, the two "D" shaped electrodes allow for efficient packing of right and left halves of the head, thus reducing the overall cross sectional dimensions of the head when folded prior to insertion through or retraction from a natural orifice or an incision.

Figure 20A:
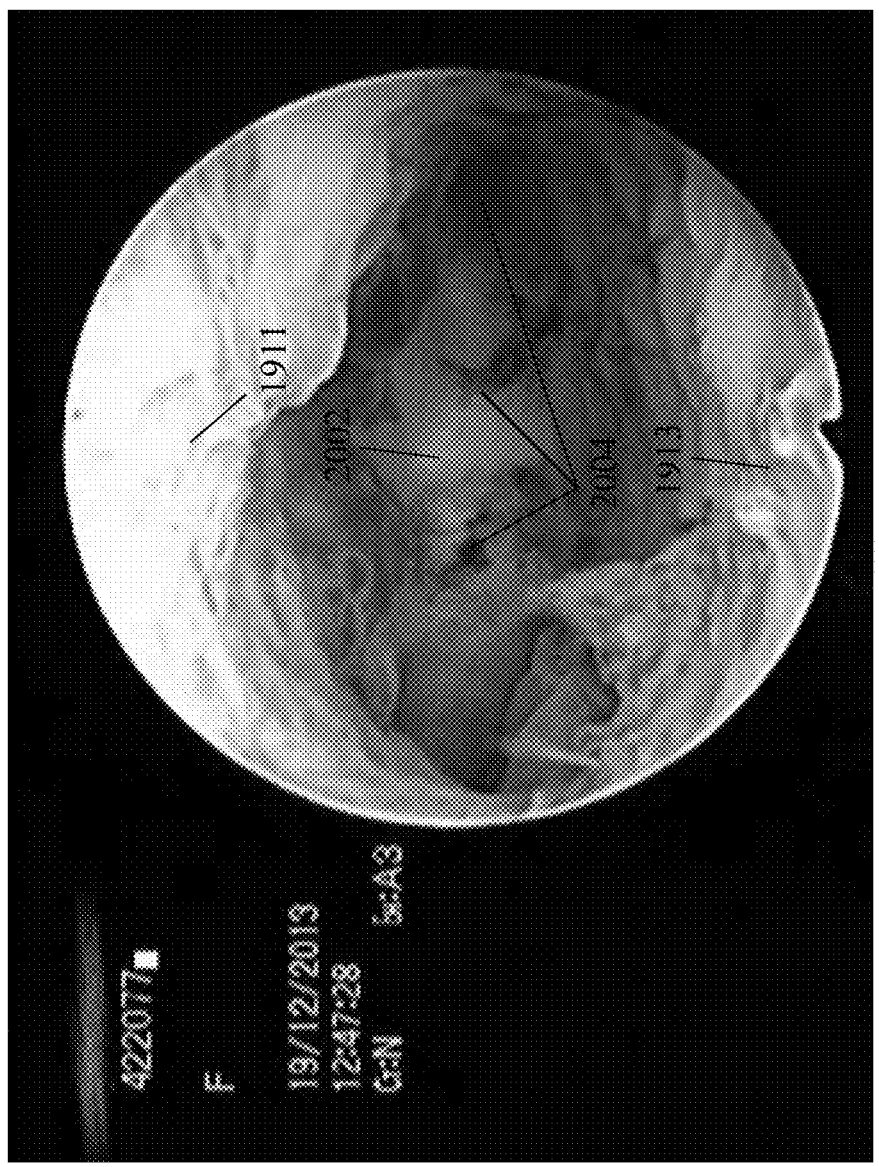
FIG. 20A shows a snap shot of a uterine cavity using a video camera in a hysteroscope before treatment using the hollow body ablation device.

FIG. 20A shows a snap shot 2000a of a uterine cavity using a video camera in a hysteroscope before treatment using the hollow body ablation device. FIG. 20A includes at least anterior endometrial surface 1911 and posterior endometrial surface 1913, which were discussed in conjunction with FIGS. 18A, 18B, and 19. FIG. 20A also includes at least fundus endometrial surface 2002 and blood 2004. In other views, FIG. 20A may not necessarily show all of the elements or features listed and/or may have other elements or features instead of or in addition to those listed. In addition, hollow body ablation device may be used in other types, shapes, and/or sizes of uteri or other body cavities.

In FIG. 20A, the anterior endometrial surface 1911 and posterior endometrial surface 1913 appear purplish in color due to the color of blood vessels within the endometrium that shed blood into the uterine cavity. Fundus endometrial surface 2002 is the endometrial surface close to the fundus. Blood 2002 is released from blood vessels within endometrium of the uterus.

Figure 20B:
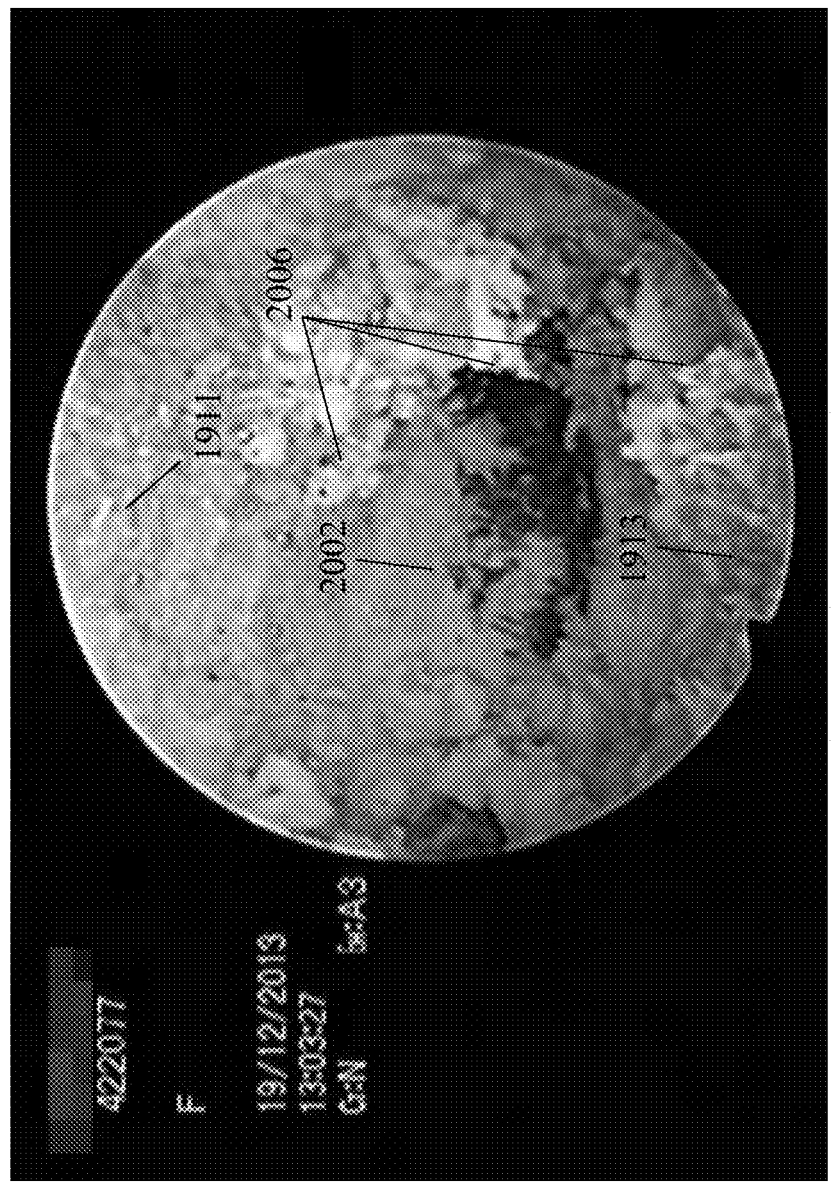
FIG. 20B shows a snap shot of a uterine cavity using a video camera in a hysteroscope after treatment using the hollow body ablation device.

FIG. 20B shows a snap shot 2000b of a uterine cavity using a video camera in a hysteroscope after treatment using the hollow body ablation device. FIG. 20B includes at least anterior endometrial surface 1911 and posterior endometrial surface 1913, which were discussed in conjunction with FIG. 19. FIG. 20B also includes fundus endometrial surface 2002, which was discussed in conjunction with FIG. 20A. FIG. 20B further includes at least ablated tissue 2006. In other views, FIG. 20B may not necessarily show all of the elements or features listed and/or may have other elements or features instead of or in addition to those listed.

In FIG. 20B, the anterior endometrial surface 1911 and posterior endometrial surface 1913 are in grayish color, indicating that the endometrium of the uterus has been uniformly ablated.

Ablated tissue 2006 is in grayish color indicating that the tissue has been ablated.

Figure 21A:
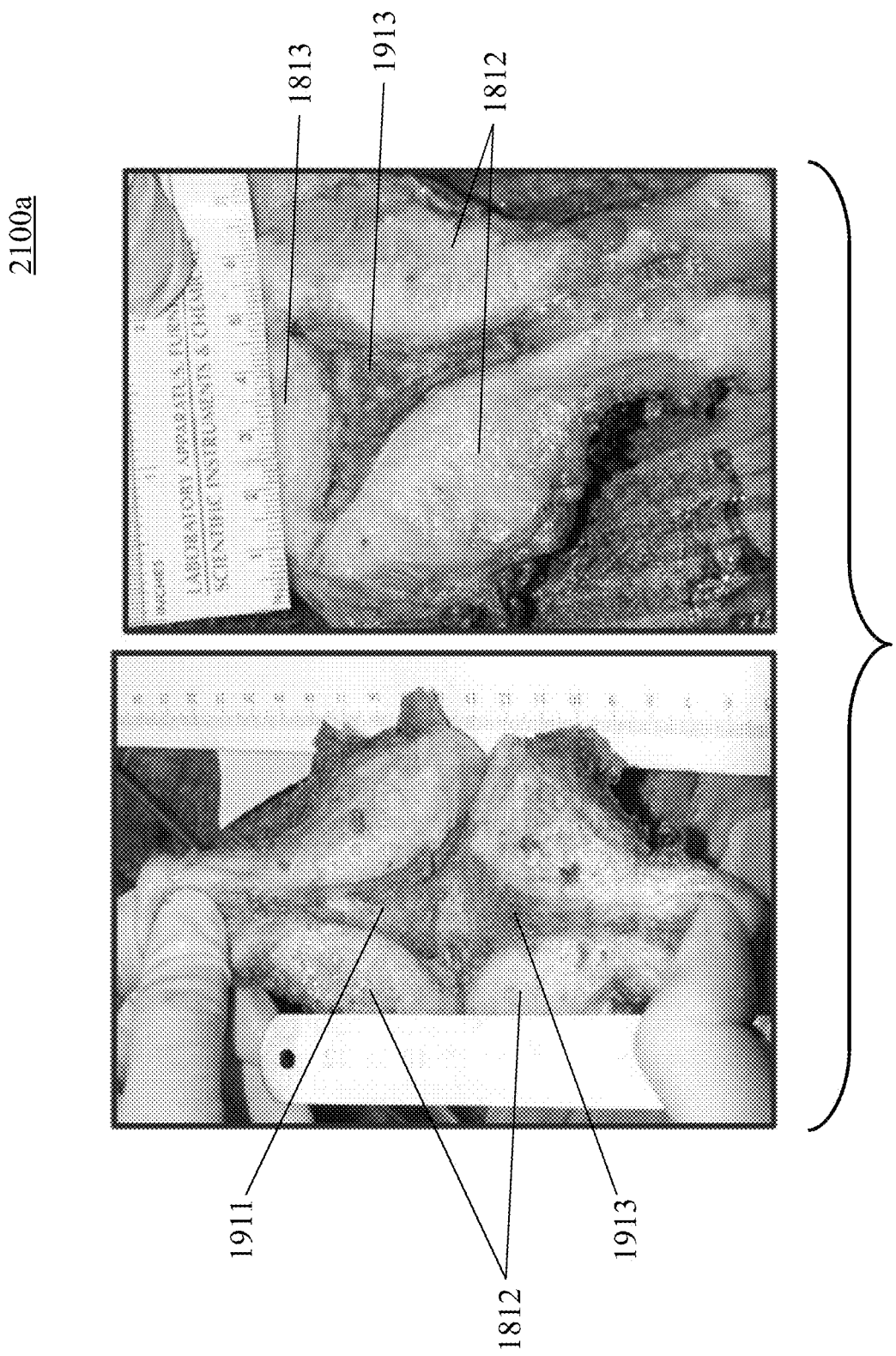
FIG. 21A shows images of two bivalved human uterine specimens after treatment using the hollow body ablation device.

FIG. 21A shows images 2100a of two bivalved human uterine specimen after treatment using the hollow body ablation device. FIG. 2A includes at least myometrium 1812, anterior endometrial surface 1911, and posterior endometrial surface 1913 of the uterine specimen on the left, and myometrium 1812, fundus 1813, and posterior endometrial surface 1913 of the uterine specimen on the right. In other views, FIG. 21A may not necessarily show all of the elements or features listed and/or may have other elements or features instead of or in addition to those listed.

Regarding FIG. 21A, five uteri were obtained immediately after hysterectomy from five patients whose ages vary from 42 to 48 and the causes for hysterectomy include adenomyosis, endometrial hyperplasia, Cervical intraepithelial neoplasia (CIN), etc. After hysterectomy, the sizes of uterine cavities were measured and then a single treatment of RF ablation was applied to each uteri using the hollow body ablation device. Each uterine specimen was treated using an RF energy setting based on the size of the uterine cavity (e.g., according to Tables 2A and 2B in FIGS. 16 and 17). In general, the ablation time was about 2 minutes. FIG. 21A shows that the anterior endometrial surface 1911, and posterior endometrial surface 1913 of the specimen on the left is uniformly ablated, while the myometrium 1812 is not affected. The image on the right of FIG. 21A also confirms that the entire area across the posterior endometrial surface 1913 is uniformly ablated with generally no charring on the perimeter of the uterine cavity.

Figure 21B:
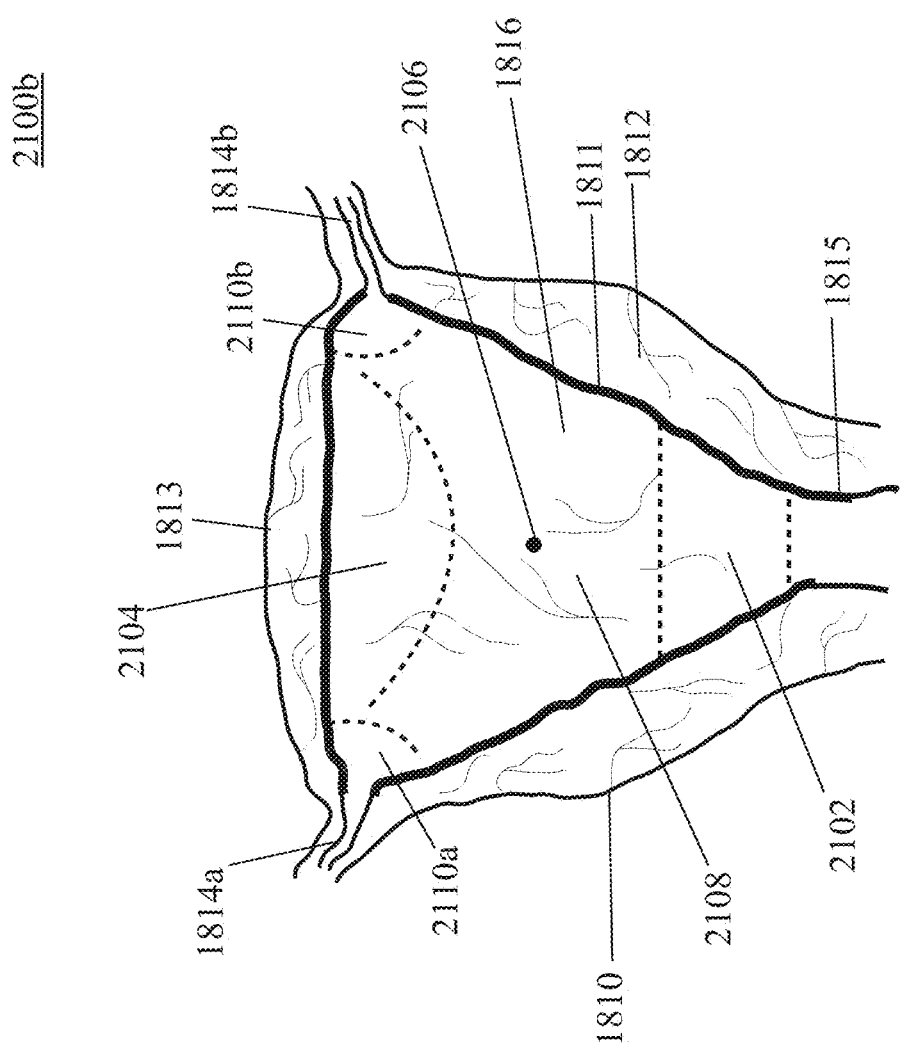
FIG. 21B shows a cross sectional anterior view of an embodiment of segmentation of a uterine cavity of a patient.

FIG. 21B shows a cross sectional anterior view 2100b of an embodiment of segmentation of a uterine cavity of a patient. FIG. 21B includes at least uterus 1810, endometrium 1811, myometrium 1812, fundus 1813, fallopian tubes 1814a-b, cervical canal 1815, and posterior surface 1816, which were discussed in conjunction with FIG. 18A. FIG. 21B also includes at least proximal segment 2102, upper segment 2104, middle point 2106, middle to cornea segment 2108, and segments near cornea 2110a-b. In other embodiments, FIG. 21B may not have all of the elements or features listed and/or may have other elements or features instead of or in addition to those listed.

In FIG. 21B, the posterior surface 1816 is artificially divided into different segments in order to facilitate assessing the effects of ablation in different segments using the hollow body ablation device.

Proximal segment 2102 is a segment of the posterior surface 1816 that is close to the cervical canal 1815. Upper segment 2104 is a segment of the posterior surface 1816 that is close to the fundus 1813. Middle point 2106 is a point approximately in the middle of the posterior surface 1816. Middle to cornea segment 2108 is a segment of the posterior surface 1816 that is near the middle point 2106 and extending to meet the proximal segment 2102, upper segment 2104, and two segments that are close to cornea. Segments near cornea 2110a-b are two segments of the posterior surface 1816 that are close to the cornea. In at least one embodiment, the anterior surface of the uterus 1810 also includes segments that are similar to proximal segment 2102, upper segment 2104, middle point 2106, middle to cornea segment 2108, and segments near cornea 2110a-b.

FIG. 21C includes a table 2100c showing the depth of necrosis in different segments of the five uteri after treatment using the hollow body ablation device. Case numbers 1-5 of FIG. 21C correspond to the five uteri obtained immediately after hysterectomy, as discussed, in conjunction with FIG. 21A. In at least one embodiment, tissue in different segments of the uteri are dissected and stained using Hematoxylin and eosin (H&E) and/or nitroblue tetrazolium (NBT) for distinguishing unablated tissue from necrotic tissue (as a result of the ablation) thus the depth of necrosis with respect to the endometrial surface of the uteri can be measured. Table 2100c shows the depth in millimeters (mm) of necrosis using H&E staining and/or NBT staining. In at least one embodiment, the depth of necrosis of uteri using H&E staining is 6.44±1.53 mm, and the depth using NBT staining is 6.77±1.50 mm. The results of H&E staining and NBT staining both show that the necrosis caused by ablation using the hollow body ablation device is approximately uniform across different segments, and the endometrium is ablated while the myometrium is generally not affected.

ALTERNATIVES AND EXTENSIONS

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:
1. A hollow body ablation apparatus, comprising;
a head having-at-least
a plurality of electrodes, at least one insulator, the head including at least an elongated member having sides and a base, Wherein when the hollow body ablation apparatus is deployed, the sides and base outline a perimeter of a region of a tissue to be ablated, which is a region of the tissue to be ablated that is outlined by the perimeter, the perimeter defined by the sides and base;
a controller in electrical communication with the plurality of electrodes controlling modes of energizing the plurality of electrodes; and
wherein at least one of the modes of energizing the plurality of electrodes is a bipolar mode of operation for controlling polarities of the plurality of electrodes to form one or more pairs of electrodes, each electrode of the one or more pairs of electrodes having an opposite polarity from one another during at least part of the bipolar mode, the opposite polarity of the one or more pairs of electrodes causing electric fields to be established to cover an entirety of the region of the tissue to be ablated that is outlined by the perimeter;
wherein the electric fields are capable of ablating the region of the tissue to be ablated that is outlined by the perimeter, without ablating the myometrium, wherein no electrode is in direct contact with the region of the tissue to be ablated that is outlined by the perimeter, and no other parts of the head are within the region of the tissue to be ablated that is outlined by the perimeter when the hollow body ablation apparatus is deployed.

2. The hollow body ablation apparatus of claim 1, wherein the sides and the base form a triangular shape when in a deployed configuration, wherein a first set of the plurality of electrodes are located on the base and a second set of the plurality of electrodes are located on two sides of the triangular shape.

3. The hollow body ablation apparatus of claim 2, wherein, when activated, the bipolar mode of operation causes the controller to control the polarity of each electrode first set of the plurality of electrodes and the polarity of each electrode of the second set of the plurality of electrodes, wherein the first set of the plurality of electrodes have an opposite polarity from one another and the second set of plurality of electrodes have, an opposite polarity from one another, and wherein one electrode of the first set of the plurality of electrodes and one electrode of the second set of the plurality of electrodes that are close to each other have an opposite polarity from one another.

4. The hollow body ablation apparatus of claim 2, the plurality of electrodes fur her including a third set of the plurality of electrodes located on sections of the two sides that are further from the base, wherein the second set of the plurality of electrodes are located on sections of the two sides that are closer to the base; wherein during the bipolar mode, the third set of the plurality of electrodes are activated, by the controller, separately, with different power settings, from the first set of the plurality of electrodes and second set of the plurality of electrodes.

5. The hollow body ablation apparatus of claim 4, the controller having a first mode and a second mode, wherein, when activated, the first mode causes the controller to energize the first set of the plurality of electrodes and the second set of the plurality of electrodes by at least applying a first voltage for a first duration of time, and when activated, the second mode causes the controller to then energize the third set of the plurality of electrodes by at least applying a second voltage for a second duration of time, wherein the first voltage and second voltage are different, the first duration of the time and the second duration of time am different, and the plurality of electrodes in the third set having opposite electric charges when energized.

6. The hollow body ablation apparatus of claim 1, wherein at least one electrode of the plurality of electrodes is flexible.

7. The hollow body ablation apparatus of claim 1, wherein each of the sides and base include at least a rigid section that provides support for the sides of the head, facilitating holding the head in a predetermined shape when deployed head is deployed.

8. The hollow body ablation apparatus of claim 1, when in at least one electrode of the plurality of electrodes is rigid, facilitating holding the head in a predetermined shape when deployed head is deployed.

9. The hollow body ablation apparatus of claim 1, further comprising
    at least a pull wire within the sides and base of the head for adjusting a width of the head by adjusting the base of the head, to fit a minimum dimension of an organ.

10. The hollow body ablation apparatus of claim 1, wherein at least two electrodes of the plurality of electrodes are D-type electrodes, each of the D-type electrodes including at least a tubular electrode with a "D" shape cross section having a rounded side and a flat side, wherein the flat side of a first D-type electrode of the at least two D-type electrodes faces the flat side of a second D-type electrode of the at least two D-type electrodes, so that when the head is collapsed the flat side of the first D-type electrode is adjacent to and faces the flat sides of the second D-type electrode and a combination of the rounded side of the first D-type electrode and the rounded side of the second D-type electrode form an exterior surface of a cylindrical tube.

11. The hollow body ablation apparatus of claim 1, further comprising a sheath in which the head collapses, the sheath having an outer diameter, wherein the outer diameter of the sheath is between about 4 and 6.5 mm.

12. The hollow body ablation apparatus of claim 1, wherein each pair of the one or more pairs of electrodes can be activated by at least applying an AC or radiofrequency (RF) energy delivery mode.

13. The hollow body ablation apparatus of claim 1, the plurality of electrodes being arranged on the sides and the base in a single layer.

14. A hollow body ablation apparatus comprising:
    a head having-at-least
        a plurality of electrodes, at least one insulator, the head including at least art elongated member having sides and a base, wherein when the hollow body ablation apparatus is deployed, the sides and base outline a perimeter of a region of a tissue to be ablated, which is a region of the tissue to be ablated that is outlined by the perimeter, the perimeter defined by the sides and the base;
    a controller in electrical communication with the plurality of electrodes controlling modes of energizing the plurality of electrodes; and
    wherein the at least one of the modes of energizing the plurality electrodes is a bipolar mode of operation for controlling polarities a bipolar, mode of operation for controlling polarities of the plurality of electrodes to form one or more pairs of electrodes, each electrode of the one or more pairs of electrodes having an opposite polarity from one another during at least part of the bipolar mode, the opposite polarities of the one or more pairs of electrodes causing electric fields to be established to cover at least an entirety of the region of the tissue to be ablated that is outlined by the perimeter;
    wherein the electric fields are capable of ablating the region of the tissue to be ablated that is outlined bate perimeter, wherein no electrode is in direct contact with the region of the tissue the tissue be ablated that is outlined by the perimeter, and no other parts of the head are within the region of the tissue to be ablated that is outlined by the perimeter when the hollow body ablation apparatus is deployed;
    wherein the region of the tissue to be ablated that is outlined by the perimeter includes at least two surfaces of a hollow cavity that face one another, that are each outlined by the perimeter; wherein the causing of the electric fields to be established to cover at least the tutu entirety of the region of the tissue to be ablated that is outlined by the perimeter includes at least, during the bipolar mode, the electric fields causing an entirety of the two surfaces, to be ablated, and where, when the head is deployed in hollow cavity, no electrode is in direct contact with the two surfaces, within the perimeter, and no other parts of th head are within the perimeter, wherein the electrodes that ablate a first surface of the two surfaces also ablate a second surface of the two surfaces.

15. The hollow body ablation apparatus of claim 14, wherein the electric fields that cause of the entirety of the at least two surfaces of the hollow cavity that are outlined by the perimeter to he ablated are capable of causing the entirety of the at least two surfaces of the hollow cavity that are outlined by the perimeter be ablated even if the at least two surfaces of the hollow cavity that are outlined by the perimeter are not in contact with each other.

16. A hollow body ablation apparatus comprising:
a head having-at-least
a plurality of electrodes, at least one insulator, the head including at least an elongated member having sides and a base, wherein when the hollow body ablation apparatus is deployed, the sides and base outline a perimeter of a region or a tissue to be ablated, which is a region of the tissue to be ablated that is outlined by the perimeter, the perimeter defined by the sides and the base;
a controller in electrical communication with the plurality of electrodes controlling modes of energizing the plurality of electrodes; and
wherein at least one of the modes of energizing the plurality of electrodes is a bipolar mode of operation for controlling polarities of the plurality of electrodes to form one or more pairs of electrodes, each electrode of the one or more pairs of electrodes having an opposite polarity from one another during at least part of the bipolar mode, the opposite polarity of the one or more pairs of electrodes causing electric fields to be established to cover an entirety of the region of the tissue to be ablated;
wherein the electric fields are capable of ablating the region of the tissue to be ablated that is outlined by the perimeter, wherein no electrode is in direct contact with the region of the tissue to be ablated that is outlined by the perimeter, and no other parts of the head are within the region of the tissue to ablated when the hollow body ablation apparatus is deployed;
wherein the head has an adjustable width,
the plurality of electrodes including at least
a first set of electrodes, the first set of electrodes are flexable, and
a second set of electrodes;
the head further including at least two insulator sleeves between the first set of electrodes and the second set of electrodes; wherein
a first insulator sleeve of the at least two sleeves is between a first electrode of the first set of electrodes and a first electrode of the second set of electrodes, the first electrode of the first set of electrodes is retractable into the first electrode of the second set electrodes with the first insulator sleeve between the first electrode of the first set of electrodes and the first electrode of the second set of electrodes, the first insulator sleeve insulates the first electrode of the first set electrodes from the first elect de of the second set of electrodes, and
a second insulator sleeve of the at least two insulator sleeves is between a second electrode of the first if electrodes and a second electrode of the second set of electrodes, the second electrode of the first set of electrodes is retractable into the second electrode of the second set of electrodes with the second insulator sleeve between second electrode of the first set of electrodes and the second electrode of the second set of electrodes, the second insulator sleeve insulates the second electrode of the firm set of electrodes from the second electrode of the second set of electrodes,
wherein the first set of electrodes slideably engage the second set of electrodes within the at least two insulator sleeves such that the head accommodates multiple widths of the head, the head being adjustable to the multiple widths by adjusting a degree to which the first set of electrodes are retracted within the at least two insulator sleeves.

17. A hollow body ablation apparatus, comprising:
a head having at least six electrodes, at least one insulator, the head comprising an elongated member having sides and a base, wherein the sides and base outline a perimeter of a region of a tissue to be ablated, which is region of the tissue to be ablated that is outlined by the perimeter, the head including
a first set of electrodes including at least a first pair of the at least six electrodes, the first set of electrodes being located on the base;
a second set of electrodes including at least a second pair of the at least six electrodes, the second set of electrodes being located on sections of the sides that are closer to the base than a third set of electrodes;
the third set of electrodes including at least a third pair of the at least six electrodes, the third set of electrodes being located on sections of the sides that are further from the base than the second set of electrodes;
a controller in electrical communication with the at least six electrodes, the controller having at least two modes of energizing the at least six electrodes, when activated, the modes causing electric fields to be established for ablating an entinity of the region of the tissue to be ablated that is outlined by the perimeter;
the at least two modes of energizing the plurality of electrodes include a first mode and a second mode, wherein when activated, the first mode of the controller, causes the controller to energize the first set of electrodes and the second set of electrodes, during at least a portion of the first mode, the at least first pair of electrodes of the first set of electrodes having opposite electric charges from one another, and during at least a portion of the first mode, the first mode causes the controller to cause the at least second pair of electrodes of the second set of electrodes to have opposite electric charges from one another, wherein during at least a portion of the first mode, the first mode causes the controller to cause one of the first set of electrodes and one of the second set of electrodes that are close to each other to have opposite electric charges from one another; and
wherein when activated, the second mode of the controller causes the controller to energize the third set of electrodes, during at least a portion of the second mode, the at least third pair of electrodes of the third set of electrodes having opposite electric charges from one another.

18. The hollow body ablation apparatus of claim 17, wherein the region of the tissue ablated by the head is one of two surfaces of a hollow cavity, wherein the electric fields are capable of ablating an entirety of the two surfaces of the hollow cavity within the perimeter where no electrode is in direct contact with the two surfaces within the perimeter, and wherein the entirety of the region of the tissue to he ablated that is outlined is the entirety of the two surfaces of the hollow cavity within the perimeter where no electrode is in direct contact with the two surfaces within the perimeter.

19. A hollow body ablation apparatus, comprising:
a head having a plurality of electrodes, at least one insulator, the head including at least an elongated member having sides and a base, wherein the sides and base outline a perimeter of a region of a tissue to be ablated; which is a region of the tissue to be ablated that is outlined by the perimeter, the perimeter defined by the sides and the base;

a controller in electrical communication with the plurality of electrodes controlling modes of energizing each electrode;

wherein the modes of energizing the plurality of electrodes includes-at-least bipolar modes of operation for controlling polarities of each electrode to coma various combinations of bipolar coupling pairs, the bipolar coupling pairs having, opposite electric charges wring at least part of the bipolar modes; and wherein, when activated, the controller controls a formation of the bipolar coupling pairs to establish electric fields to cover an entirety of the region of the tissue to be ablated that is outlined by the perimeter, wherein when the controller is activated the electric fields cause the entirety of the region of the tissue to be ablated that is outlined by the perimeter, to be uniformly ablated where no electrode is in direct contact with the region of the tissue to be ablated that is outlined by the perimeter, no components of the head are located within the perimeter when the head is deployed, without charring the hollow body.

20. A hollow body ablation apparatus, comprising:
a head having-at-least
a plurality of electrodes, at least one insulator, the head including at least an elongated member having sides and a base, wherein when the hollow body ablation apparatus is deployed, the sides and base outline a perimeter of a region of a tissue to be ablated, which is a region of the tissue to be ablated that is outlined by the perimeter, the perimeter defined by the sides and base;

a controller in electrical communication with the plurality of electrodes controlling modes of energizing the plurality of electrodes; and wherein at least one of the modes of energizing the plurality of electrodes includes a bipolar mode of operation for automatically controlling polarities of the plurality of electrodes to form one or more pairs of electrodes, each electrode of the one or more pairs of electrodes having opposite polarity from one another during at least part of the bipolar mode, the opposite polarities of the one or more pairs of electrodes causing electric fields to be established to cover an entirety of the region of the tissue to be ablated;

wherein the bipolar mode of operation, when implemented, is capable of automatically ablating the region of the tissue to be ablated hat is outlined by the perimeter, without charring tissue that is closest to the electrodes, as a result of the electric fields established by the controller; wherein no electrode, as direct contact with the region of the tissue to be ablated that is outlined by the perimeter.

21. The hollow body ablation apparatus of claim 20, the controller being configured to avoid charring of the tissue.

22. A method comprising ablating by the hollow body ablation of claim 20, so that the region within the circumference of the electrodes is ablated uniformly without charring tissue in contact with the electrodes.

23. The hollow body ablation apparatus of claim 20, the controller including at least
a microprocessor and
a signal generator controlled by the microprocessor.

24. The hollow body ablation apparatus of claim 20, the plurality of electrodes being arranged on the sides and the base in a single layer, and no parts of the head are within the perimeter.

25. The hollow body ablation apparatus of chum 20, the controller, when activated, detecting a width of the head and a length of the head.

26. The hollow body ablation apparatus of claim 25, the controller including a display, and when activated, the controller displays on the display a first value representing the width at the head, which was detected, and a second value representing the length of the head, which was detected.

27. The hollow body ablation apparatus of claim 25, the controller when activated, adjusting parameters of the modes of energizing based on the width detected and the length detected, so that when the mode is implemented the controller automatically causes the electric fields to be established that will ablate the entirety al the region of the tissue to be ablated that is outlined by the perimeter without charring tissue closest to the plurality of electrodes.

28. A hollow body ablation apparatus comprising:
a head-having-at-least
a plurality of electrodes, at least one insulator, the head including at least an elongated member having sides and a base, wherein when the hollow body ablation apparatus is deployed, the sides and base outline a perimeter of a region of a tissue to be ablated, which is a region of the tissue to be ablated that is outlined by the perimeter, the perimeter defined the sides and base;

a controller in electrical communication with the plurality of electrodes controlling modes of energizing the plurality of electrodes; and wherein at least one of the modes of energizing the plurality of electrodes includes a bipolar mode of operation for automatically controlling polarities of the plurality of electrodes to from one or more pairs of electrode, each electrode of the one or more pairs of electrodes having opposite polarity from one another during at least part of the bipolar mode, the opposite polarities of the one or more pairs of electrodes causing electric fields to be established to cover can an entirety of the region of the tissue to be ablated;

wherein the bipolar mode of operation, when implemented, the bipolar mode of operation is capable of automatically a ablating the region of the tissue to be ablated that is outlined by the perimeter, in locations where no electrode is in direct contact with the region of the tissue to be ablated that is outlined by the perimeter;

the bipolar mode of the controller including a first predefined mode and a second predefined mode, wherein, when activated, the first predefined mode causes the controller to automatically energize a first set of the plurality of electrodes by at least applying a first electric field of a first amount of power for a first duration of time of application therein generating the first electric field in a first region within the region within the perimeter, and when activated, the second mode causes the controller to automatically energize a second set of the plurality of electrodes by at least applying a second electric field of a second amount of power for a second duration of time therein generating the second electric field in a second region within the region within the perimeter that does not overlap the first region, the electric fields established by the controller include the first electric field and the second electric field;

wherein the first amount of power and the second amount of power are different, and the first duration of time and the second duration of time are different, wherein the first amount of power and the first duration of time and the second amount of power and second duration of time are chosen so that the first region and second region will be ablated to improve uniformity of the ablation as compared to were the same amount of power and same duration of time applied to both the first region and the second region.

* * * * *